United States Patent
Di Fabio et al.

(10) Patent No.: US 12,404,284 B2
(45) Date of Patent: Sep. 2, 2025

(54) SPIROCYCLIC INHIBITORS OF HEPATITIS B VIRUS

(71) Applicants: Ospedale San Raffaele S.r.l., Milan (IT); Istituto Nazionale Genetica Molecolare—INGM, Milan (IT)

(72) Inventors: Romano Di Fabio, Pomezia (IT); Vincenzo Summa, Pomezia (IT); Leda Ivanova Bencheva, Milan (IT); Raffaele De Francesco, Milan (IT); Lorena Donnici, Milan (IT); Luca Guidotti, Milan (IT); Matteo Iannacone, Milan (IT); Adolfo Prandi, Milan (IT); Marilenia De Matteo, Milan (IT); Pietro Randazzo, Milan (IT)

(73) Assignees: Ospedale San Raffaele S.r.l., Milan (IT); Istituto Nazionale Genetica Molecolare—INGM, Milan (IT)

( * ) Notice: Subject to any disclaimer, the term of this patent is extended or adjusted under 35 U.S.C. 154(b) by 617 days.

(21) Appl. No.: 17/798,784

(22) PCT Filed: Feb. 9, 2021

(86) PCT No.: PCT/EP2021/053099
§ 371 (c)(1),
(2) Date: Aug. 10, 2022

(87) PCT Pub. No.: WO2021/160617
PCT Pub. Date: Aug. 19, 2021

(65) Prior Publication Data
US 2023/0151027 A1    May 18, 2023

(30) Foreign Application Priority Data

Feb. 11, 2020 (EP) .................................... 20156716
Oct. 14, 2020 (EP) .................................... 20201798

(51) Int. Cl.
*C07D 515/14* (2006.01)

(52) U.S. Cl.
CPC ................................. *C07D 515/14* (2013.01)

(58) Field of Classification Search
CPC .................................................. C07D 515/14
See application file for complete search history.

(56) References Cited

FOREIGN PATENT DOCUMENTS

WO    2017/001655 A1    1/2017

OTHER PUBLICATIONS

ISA/EP, "PCT International Search Report and Written Opinion" issued in connection with international application No. PCT/EP2021/053099, which were mailed on Apr. 13, 2021 (15 pages).

*Primary Examiner* — Joseph K McKane
*Assistant Examiner* — Jalisa Holmes Ferguson
(74) *Attorney, Agent, or Firm* — Lucas & Mercanti, LLP

(57) ABSTRACT

The present invention relates to compounds that are inhibitors of hepatitis B virus (HBV). Compounds of this invention are useful alone or in combination with other agents for treating, ameliorating, preventing or curing HBV infection and related conditions. The present invention also relates to pharmaceutical compositions containing the compounds.

17 Claims, No Drawings
Specification includes a Sequence Listing.

SPIROCYCLIC INHIBITORS OF HEPATITIS B VIRUS

CROSS-REFERENCE TO RELATED APPLICATIONS

This application is a 371 of PCT/EP2021/053099, filed Feb. 9, 2021, which claims the benefit of European Patent Application Nos. 20156716.1, filed Feb. 11, 2020, and 20201798.4, filed Oct. 14, 2020.

REFERENCE TO A SEQUENCE LISTING SUBMITTED ELECTRONICALLY VIA EFS-WEB

The content of the electronically submitted sequence listing, file name: 128-1263_SeqListing.text; size: 4 KB; and data of creation: Aug. 8, 2022, filed herewith, is incorporated herein by reference in its entirety.

FIELD OF THE INVENTION

The present invention relates to compounds that are inhibitors of hepatitis B virus (HBV).

Compounds of this invention are useful alone or in combination with other agents for treating, ameliorating, preventing or curing HBV infection and related conditions. The present invention also relates to pharmaceutical compositions containing said compounds.

BACKGROUND OF THE INVENTION

The Hepatitis B virus (HBV) is an enveloped, partially double-stranded DNA (dsDNA) virus of the hepadnaviridae family that is spread by contact with infected blood and body fluids and causes acute and chronic necroinflammatory liver diseases of varying severity (Guidotti L G, Chisari F V. Annu Rev Pathol. 2006; 1:23-61). The HBV lipid envelope contains 3 in-frame viral envelope proteins (large, middle and small), each of which possesses the hepatitis B virus surface antigen (HBsAg) determinant (Seeger C, Mason W S. Virology. 2015 May; 479-480:672-86). This envelope encloses a protein shell, or capsid, that is composed of 240 monomers of the core protein and each monomer possesses the hepatitis B virus core antigen (HBcAg or Cp) determinant. The capsid in turn encloses a partially double-stranded, relaxed circular DNA (rcDNA) form of the viral genome as well as a molecule of the viral polymerase. Upon entry into susceptible cells (i.e. the hepatocytes) via the interaction of the large envelope protein with specific receptors on the hepatocellular membrane, the capsid is released into the cytoplasm and transported at the nuclear membrane. The rcDNA is then released into the nucleus and repaired by cellular polymerases into an episomal "minichromosome", termed covalently closed circular DNA (cccDNA), which represents the viral transcriptional template. The minus strand of the viral DNA encodes 3.5, 2.4, 2.1 and 0.7 kb mRNA species that are translated into structural (envelope and core) and nonstructural (polymerase, precore and X) proteins of the virus. Following transport into the cytoplasm, one of the 3.5 kb RNAs (termed pregenomic RNA) is selectively packaged into a nascent capsid by interacting with the core and polymerase proteins that have been translated from their respective mRNAs. Within these capsids, the viral polymerase reverse transcribes the pregenomic RNA into a single (−) strand DNA molecule that serves as template for the viral polymerase-mediated DNA (+) strand synthesis and the cohesive structure of the linear DNA intermediates converts them into a relaxed circular double stranded molecule. A fraction of these HBV DNA-containing "mature" capsids are transported back to the nucleus where second strand synthesis is completed and the ends of both strands are ligated, leading to amplification of the pool of cccDNA. Another fraction of the capsids binds to viral envelope proteins that have been independently translated and translocated to membranes of endoplasmic reticulum (ER)-like structures. Following binding, the enveloped capsids bud into the lumen of the ER and exit the cell as infectious virions to initiate new cycles of infection.

Thus, the HBV core protein and the related capsids are essential components and regulators of the HBV life cycle. The full-length core protein Cp183, or its N-terminal domain Cp149, predominantly assembles into a T=4 icosahedral capsids. Due to its critical roles in capsid assembly, pregenomic RNA packaging, and cccDNA maintenance, it is not surprising that the HBV core protein and the related capsids have been widely recognized as attractive antiviral targets (Durantel D, Zoulim F; J Hepatol. 2016 April; 64(1 Suppl):S117-S131).

According to World Health Organization (WHO) statistics, HBV infection is one of the major medical scourges of our time. As a sexually transmitted disease that is also transferred by intravenous drug abuse and from mother to infant at birth, over one third of the world's population has been infected by HBV at some point in their lives (Burns G S, Thompson A J; Cold Spring Harb Perspect Med. 2014 Oct. 30; 4(12)). While most of these people have successfully cleared the virus, more than 250 million people remain persistently infected and almost 900,000 of these individuals die annually from the complications of chronic infection (i.e. cirrhosis and/or hepatocellular carcinoma). HBV infection is highly endemic in sub-Saharan Africa, the Pacific, and particularly Asia. Regions with high rates of chronic HBV infection also include the Middle East, the Indian subcontinent, areas of South and Central America, and the southern parts of Eastern and Central Europe. In recent years the number of chronic carriers has increased steadily in the western world as well, mostly because of the influx of immigrants from endemic areas. Additionally, HBV acts as a helper virus to hepatitis delta virus (HDV) and it should be noted that the more than 15 million people co-infected with HBV and HDV have an increased risk of rapid progression to cirrhosis and hepatic decompensation (Hughes, S. A. et al. Lancet 2011, 378, 73-85).

Well-tolerated vaccines that elicit neutralizing antibodies to HBsAg efficiently prevent de novo HBV infection, but have no therapeutic potential for the millions of people that are already persistently infected (Zoulim, Durantel D; Cold Spring Harb Perspect Med. 2015 Apr. 1; 5(4)). Therapy for these individuals mainly relies on direct acting antiviral (DAA) drugs (e.g. tenofovir, lamivudine, adefovir, entecavir or telbivudine) that suppress virus production but do not eradicate HBV from the liver, requiring lifelong treatment. Cohorts of patients still receive a therapy based on pegylated interferon-α (PEG-IFN-α), which has the advantages of limited treatment duration and higher rates of HBsAg seroconversion but the relevant disadvantage of greater adverse effects. As such, the number of patients receiving PEG-IFN-α is progressively decreasing.

Different chemical classes of inhibitors targeting the encapsidation process of HBV (also termed capsid assembly modulators or CAMs) are under development, and they include heteroaryldihydropyrimidines (HAPs) and sulfamoylbenzamides (SBAs). For instance, Novira Therapeutics recently utilized a humanized mouse model of HBV infection to show that a combination of CAM and PEG-IFN-α has higher antiviral activity than that previously observed with DAAs. NVR3-778, the first member of this class of CAM, in Phase 1b proof-of-concept clinical studies showed both significant reduction in HBV DNA and serum HBV RNA. This compound was recently discontinued. The compound JNJ-56136379 (or JNJ-379), developed by Janssen, has recently demonstrated potent antiviral activity and is now in Phase 2 clinical trial. WO2017/001655A1, published on Jan. 5, 2017, relates to cyclized sulfamoylarylamide derivatives having structure:

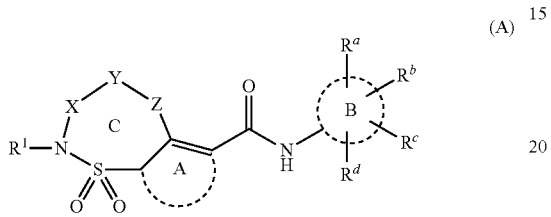

(A)

The compounds disclosed in WO2017/001655A1 include 3,4-dihydro-2H,7H-pyrrolo[3,4-b][1,4,5]oxathiazepine 1,1-dioxide derivatives substituted at the 6-position by N-phenyl-carboxamides. Some derivatives disclosed therein have a spirofused oxetane, tetrahydrofuran or pyrroline ring. WO2017/001655A1 does not disclose or suggest compounds wherein the spirofused ring is further functionalized with an amido or oxalamido group.

Amongst the problems which HBV direct antivirals may encounter are toxicity, mutagenicity, lack of selectivity, poor efficacy, poor bioavailability, low solubility and/or off-target activity, and until now there are no compounds in any of the structural classes identified above approved as drugs for the treatment of HBV patients.

There is a need for additional HBV inhibitors that may overcome at least one of these disadvantages or that have additional advantages such as increased potency, increased bioavailability or an increased safety window.

The present invention provides small molecule drugs obtained through chemical modification of the known sulfamoyl arylamides derivatives. In particular the compounds of the invention are characterized by a tricyclic core structure comprising a pyrrole ring, bearing an amide or oxalamide substituent on a specific position of the fused tricyclic core. The chemotype discovered in the present invention results in extremely potent HBV inhibitors with improved pharmacokinetic properties, good kinetic solubility, stability in mouse and human hepatocytes, low in vivo clearance and positive liver-to-plasma concentration. Given the liver's key role in metabolic regulation and the fact that it is the principal tissue affected by hepatitis B disease, designing HBV inhibitors with hepatoselective distribution profiles is an important strategy in developing safe drug candidates (Tu M. et al., Current Topics in Medicinal Chemistry, 2013, 13, 857-866).

DESCRIPTION OF THE INVENTION

The compounds of this invention are inhibitors of hepatitis B virus (HBV).

It is therefore an object of the present invention a compound of general formula (I):

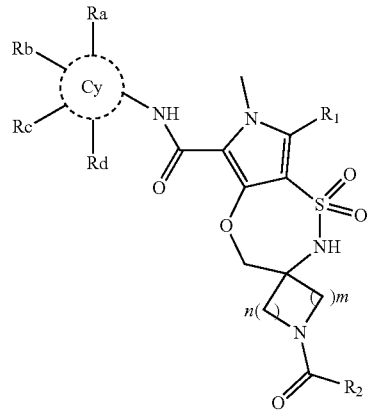

(I)

wherein:
Cy is aryl or heteroaryl;
each of m and n is independently 1 or 2;
$R_1$ is H, F, Br, Cl or $CH_3$;
$R_2$ is selected from the group consisting of:
5 or 6 membered heteroaryl ring optionally substituted with one or more substituents each independently selected from the group consisting of: OH, halogen, CN, $C_{1-6}$alkyl, hydroxy$C_{1-6}$alkyl, halo$C_{1-6}$alkyl, halo$C_{1-6}$alkoxy, $C_{1-6}$alkoxy and $NH_2$;
halo$C_{1-4}$alkyl; and
$C(=O)NR_3R_4$;
each of $R_3$ and $R_4$ is independently selected from the group consisting of:
hydrogen;
$C_{1-3}$alkyl;
halo$C_{1-4}$alkyl; and
$C_{3-5}$-cycloalkyl optionally substituted with one or more substituents each independently selected from the group consisting of: methyl, F, Cl, $CHF_2$ and $CF_3$;
or $R_3$ and $R_4$ form together with the nitrogen atom to which they are attached a cyclic amine selected from the group consisting of: aziridine, azetidine, pyrrolidine, piperidine, morpholine and thiomorpholine each of said cyclic amine being optionally substituted with one or more substituents each independently selected from the group consisting of: methyl, fluorine, $CHF_2$ and $CF_3$;
Ra, Rb, Rc and Rd are each independently selected from the group consisting of: hydrogen, halogen, methyl, CN, $CHF_2$ and $CF_3$;
or a pharmaceutically acceptable salt, solvate or stereoisomer thereof.

Embodiments disclosed hereinafter may be combined with each other in any possible way that would give rise to a stable compound. All such combinations are within the scope of the present invention.

In a preferred embodiment, $R_2$ is:
5 membered heteroaryl ring optionally substituted with one or more substituents each independently selected from the group consisting of: OH, halogen, CN, methyl and trifluoromethyl; or
$C(=O)NR_3R_4$ wherein $R_3$ is H and $R_4$ is selected from the group consisting of: $C_{1-3}$alkyl, halo$C_{1-4}$alkyl and $C_{3-5}$-cycloalkyl optionally substituted with one or more substituents each independently selected from the group consisting of: methyl, fluorine and $CF_3$;

or $R_3$ and $R_4$ form together with the nitrogen atom to which they are attached a cyclic amine selected from the group consisting of: aziridine, azetidine, pyrrolidine and piperidine, each of said cyclic amine being optionally substituted with one or more substituents each independently selected from the group consisting of: methyl, fluorine and $CF_3$.

In a preferred embodiment, Ra, Rb, Rc and Rd are each independently selected from the group consisting of: hydrogen, Cl, F, methyl and $CHF_2$.

In another preferred embodiment, m is 1 and n is 2; or m is 1 and n is 1; or m is 2 and n is 2.

Preferably, m is 1 and n is 2.

In yet another preferred embodiment, $R_1$ is H or Cl. Preferably, m is 1, n is 2 and $R_1$ is H or Cl.

Preferably, m is 2 and n is 2 and $R_1$ is H or Cl. Preferably, m is 1 and n is 1 and $R_1$ is H or Cl.

In a further preferred embodiment, Cy is phenyl. Preferably, Cy is phenyl; any two of Ra-Rd are independently F, Cl or $CHF_2$; and the other two of Ra-Rd are H.

In still a further preferred embodiment,

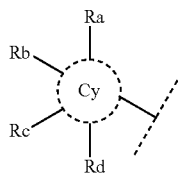

represents

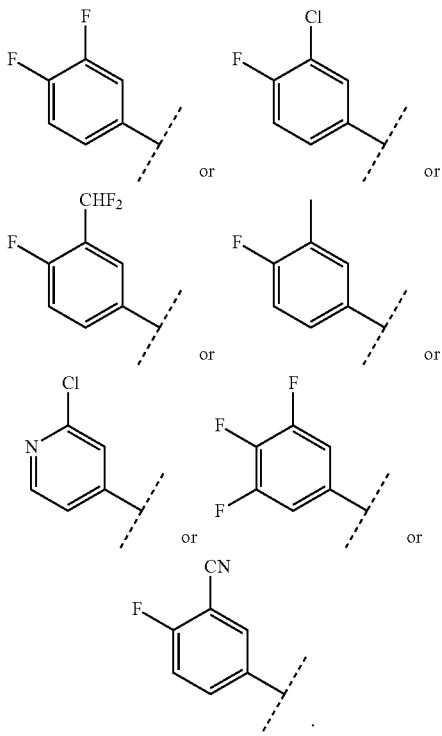

In yet another preferred embodiment, $R_2$ is:

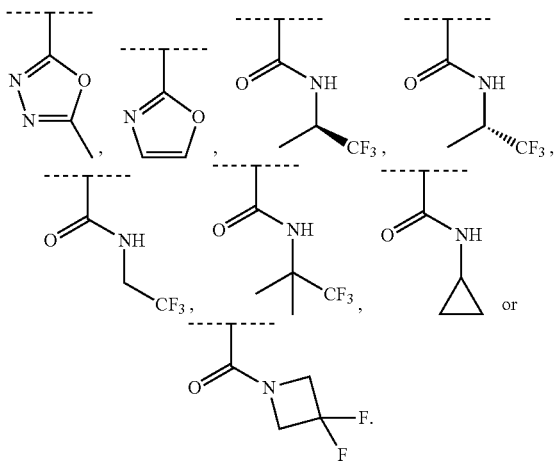

Preferably, the compound of the invention is selected from the group consisting of:

N-(3,4-difluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide;

N-(3,4-difluorophenyl)-7'-methyl-1-(5-methyl-1,3,4-oxadiazole-2-carbonyl)-2'H,4'H,7'H-spiro[pyrrolidine-3,3'-pyrrolo[3,4-b][1,4,5]oxathiazepine]-6'-carboxamide 1',1'-dioxide;

8'-chloro-N-(3,4-difluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide;

(R)—N-(3-chloro-4-fluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide;

(S)—N-(3-chloro-4-fluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide;

(R)—N-(3-(difluoromethyl)-4-fluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide;

(R)—N-(3-chloro-4-fluorophenyl)-7'-methyl-1-(2-oxo-2-((1,1,1-trifluoropropan-2-yl)amino)acetyl)-2'H,4'H,7'H-spiro[piperidine-4,3'-pyrrolo[3,4-b][1,4,5]oxathiazepine]-6'-carboxamide 1',1'-dioxide;

(R)—N-(3-(difluoromethyl)-4-fluorophenyl)-7'-methyl-1-(2-oxo-2-((1,1,1-trifluoropropan-2-yl)amino)acetyl)-2'H,4'H,7'H-spiro[piperidine-4,3'-pyrrolo[3,4-b][1,4,5]oxathiazepine]-6'-carboxamide 1',1'-dioxide;

(R)—N-(3-chloro-4-fluorophenyl)-7'-methyl-1-(2-oxo-2-((1,1,1-trifluoropropan-2-yl)amino)acetyl)-2'H,4'H,7'H-spiro[azetidine-3,3'-pyrrolo[3,4-b][1,4,5]oxathiazepine]-6'-carboxamide 1',1'-dioxide;

(R)—N-(3-(difluoromethyl)-4-fluorophenyl)-7'-methyl-1-(2-oxo-2-((1,1,1-trifluoropropan-2-yl)amino)acetyl)-2'H,4'H,7'H-spiro[azetidine-3,3'-pyrrolo[3,4-b][1,4,5]oxathiazepine]-6'-carboxamide 1',1'-dioxide;

(S)—N-(3-(difluoromethyl)-4-fluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide;

(S)—N-(3-chloro-4-fluorophenyl)-7'-methyl-1-(2-oxo-2-((1,1,1-trifluoropropan-2-yl)amino)acetyl)-2'H,4'H,7'H-spiro[piperidine-4,3'-pyrrolo[3,4-b][1,4,5]oxathiazepine]-6'-carboxamide 1',1'-dioxide;

N-(3-chloro-4-fluorophenyl)-7'-methyl-1-(2-oxo-2-((2,2,2-trifluoroethyl)amino)acetyl)-2'H,4'H,7'H-spiro[piperidine-4,3'-pyrrolo[3,4-b][1,4,5]oxathiazepine]-6'-carboxamide 1',1'-dioxide;

(S)—N-(3-(difluoromethyl)-4-fluorophenyl)-7'-methyl-1-(2-oxo-2-((1,1,1-trifluoropropan-2-yl)amino)acetyl)-2'H,4'H,7'H-spiro[piperidine-4,3'-pyrrolo[3,4-b][1,4,5]oxathiazepine]-6'-carboxamide 1',1'-dioxide;

N-(3-(difluoromethyl)-4-fluorophenyl)-7'-methyl-1-(2-oxo-2-((1,1,1-trifluoro-2-methylpropan-2-yl)amino)acetyl)-2'H,4'H,7'H-spiro[piperidine-4,3'-pyrrolo[3,4-b][1,4,5]oxathiazepine]-6'-carboxamide 1',1'-dioxide;

(S)—N-(3-chloro-4-fluorophenyl)-7'-methyl-1-(2-oxo-2-((1,1,1-trifluoropropan-2-yl)amino)acetyl)-2'H,4'H,7'H-spiro[azetidine-3,3'-pyrrolo[3,4-b][1,4,5]oxathiazepine]-6'-carboxamide 1',1'-dioxide;

N-(3-chloro-4-fluorophenyl)-1-(2-(3,3-difluoroazetidin-1-yl)-2-oxoacetyl)-7'-methyl-2'H,4'H,7'H-spiro[azetidine-3,3'-pyrrolo[3,4-b][1,4,5]oxathiazepine]-6'-carboxamide 1',1'-dioxide;

(S)—N-(3-(difluoromethyl)-4-fluorophenyl)-7'-methyl-1-(2-oxo-2-((1,1,1-trifluoropropan-2-yl)amino)acetyl)-2'H,4'H,7'H-spiro[azetidine-3,3'-pyrrolo[3,4-b][1,4,5]oxathiazepine]-6'-carboxamide 1',1'-dioxide;

1-(2-(cyclopropylamino)-2-oxoacetyl)-N-(3-(difluoromethyl)-4-fluorophenyl)-7'-methyl-2'H,4'H,7'H-spiro[azetidine-3,3'-pyrrolo[3,4-b][1,4,5]oxathiazepine]-6'-carboxamide 1',1'-dioxide;

(R)—N-(3-chloro-4-fluorophenyl)-7'-methyl-1-(2-oxo-2-((2,2,2-trifluoroethyl)amino)acetyl)-2'H,4'H,7'H-spiro[pyrrolidine-3,3'-pyrrolo[3,4-b][1,4,5]oxathiazepine]-6'-carboxamide 1',1'-dioxide;

(R)—N-(3-chloro-4-fluorophenyl)-7'-methyl-1-(2-oxo-2-((1,1,1-trifluoro-2-methylpropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide;

(R)—N-(3-chloro-4-fluorophenyl)-7'-methyl-1-(2-oxo-2-(((S)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide;

(R)—N-(3-(difluoromethyl)-4-fluorophenyl)-7'-methyl-1-(2-oxo-2-(((S)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide;

(R)—N-(3-(difluoromethyl)-4-fluorophenyl)-7'-methyl-1-(2-oxo-2-((1,1,1-trifluoro-2-methylpropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide;

(S)—N-(3-chloro-4-fluorophenyl)-7'-methyl-1-(2-oxo-2-((2,2,2-trifluoroethyl)amino)acetyl)-2'H,4'H,7'H-spiro[pyrrolidine-3,3'-pyrrolo[3,4-b][1,4,5]oxathiazepine]-6'-carboxamide 1',1'-dioxide;

(S)—N-(3-chloro-4-fluorophenyl)-7'-methyl-1-(2-oxo-2-((1,1,1-trifluoro-2-methylpropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide;

(S)—N-(3-(difluoromethyl)-4-fluorophenyl)-7'-methyl-1-(2-oxo-2-((2,2,2-trifluoroethyl)amino)acetyl)-2'H,4'H,7'H-spiro[pyrrolidine-3,3'-pyrrolo[3,4-b][1,4,5]oxathiazepine]-6'-carboxamide 1',1'-dioxide;

(S)—N-(3-(difluoromethyl)-4-fluorophenyl)-7'-methyl-1-(2-oxo-2-((1,1,1-trifluoro-2-methylpropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide;

(S)-8'-chloro-N-(3-(difluoromethyl)-4-fluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide;

(R)-8'-chloro-N-(3-chloro-4-fluorophenyl)-7'-methyl-1-(2-oxo-2-((1,1,1-trifluoropropan-2-yl)amino)acetyl)-2'H,4'H,7'H-spiro[piperidine-4,3'-pyrrolo[3,4-b][1,4,5]oxathiazepine]-6'-carboxamide 1',1'-dioxide;

(R)-8'-chloro-N-(3-chloro-4-fluorophenyl)-7'-methyl-1-(2-oxo-2-((1,1,1-trifluoropropan-2-yl)amino)acetyl)-2'H,4'H,7'H-spiro[azetidine-3,3'-pyrrolo[3,4-b][1,4,5]oxathiazepine]-6'-carboxamide 1',1'-dioxide;

(R)-8'-chloro-N-(3-(difluoromethyl)-4-fluorophenyl)-7'-methyl-1-(2-oxo-2-((1,1,1-trifluoropropan-2-yl)amino)acetyl)-2'H,4'H,7'H-spiro[azetidine-3,3'-pyrrolo[3,4-b][1,4,5]oxathiazepine]-6'-carboxamide 1',1'-dioxide;

(R)-8'-chloro-N-(3-chloro-4-fluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide;

(R)-8'-chloro-N-(3-(difluoromethyl)-4-fluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide;

(R)-8'-chloro-N-(3-(difluoromethyl)-4-fluorophenyl)-7'-methyl-1-(2-oxo-2-((1,1,1-trifluoropropan-2-yl)amino)acetyl)-2'H,4'H,7'H-spiro[piperidine-4,3'-pyrrolo[3,4-b][1,4,5]oxathiazepine]-6'-carboxamide 1',1'-dioxide;

N-(3,4-difluorophenyl)-7'-methyl-1-(2-oxo-2-(((S)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide; and 8'-chloro-N-(3,4-difluorophenyl)-7'-methyl-1-(2-oxo-2-(((S)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide or is a pharmaceutically acceptable salt, solvate or stereoisomer thereof.

Then, the present invention also provides a compound of Formula (I-A), (I-B), and/or (I-C):

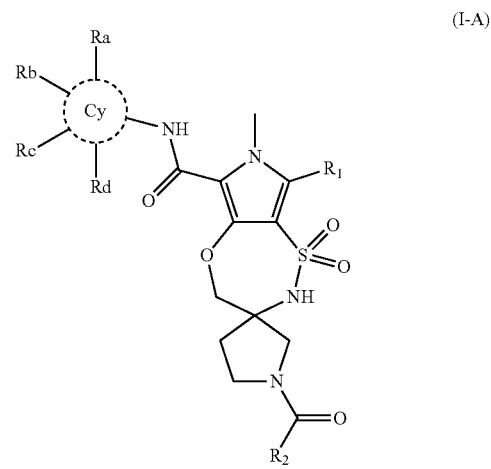

(I-A)

-continued (I-B)

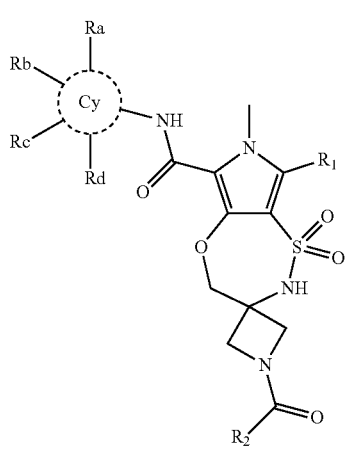

(I-C)

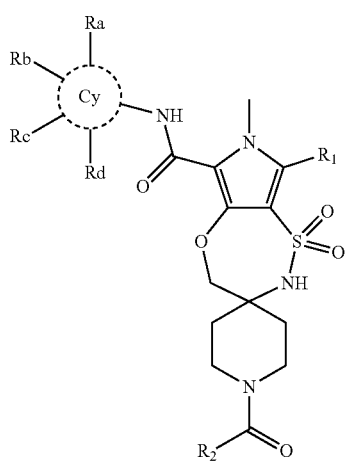

or a pharmaceutically acceptable salt, solvate or stereoisomer thereof, wherein all substituents are as defined above.

Preferably, in the compound of Formula (I-A), (I-B) or (I-C), $R_1$ is Cl or H and/or in the compound of formula (I-A), (I-B) or (I-C), $R_2$ is —C(=O)NR$_3$R$_4$.

Preferably, the compound of the invention has the Formula (I-AA), (I-AB) or (I-AC):

(I-AA)

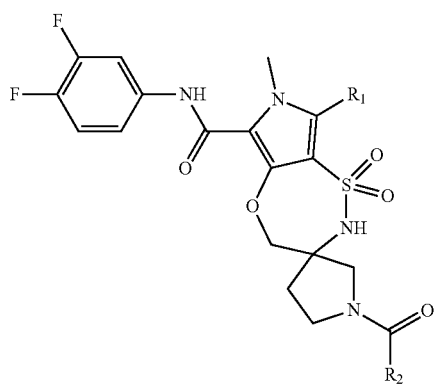

(I-AB)

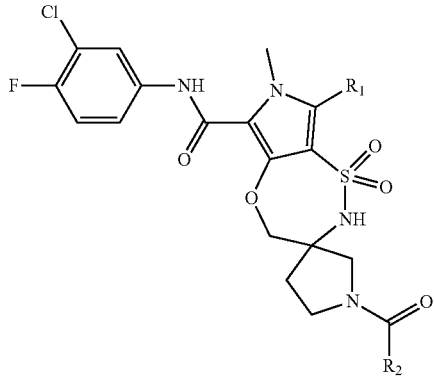

(I-AC)

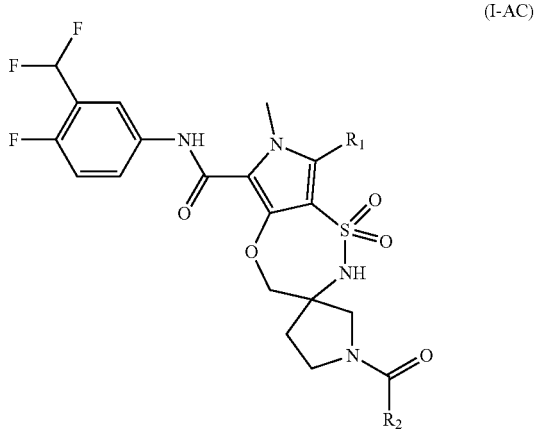

wherein $R_1$ is H or Cl;

$R_2$ is:
5 or 6 membered heteroaryl ring optionally substituted with one or more substituents each independently selected from the group consisting of: OH, halogen, CN, methyl, trifluormethyl; or

C(=O)NR$_3$R$_4$;

each of $R_3$ and $R_4$ is independently selected from the group consisting of:
hydrogen;
methyl;
haloC$_{1-4}$alkyl; and
C$_{3-5}$-cycloalkyl optionally substituted with one or more substituents each independently selected from the group consisting of: methyl, fluorine and CF$_3$;

or $R_3$ and $R_4$ form together with the nitrogen atom to which they are attached a cyclic amine selected from the group consisting of: aziridine, azetidine, pyrrolidine and piperidine, each of said cyclic amine being optionally substituted with one or more substituents independently selected from the group consisting of: methyl, fluorine and CF$_3$;

or a pharmaceutically acceptable salt, solvate or stereoisomer thereof.

Further combinations of any of the embodiments are also envisioned to be in the scope of the present invention.

In a preferred aspect, the compound, pharmaceutically acceptable salt, solvate or stereoisomer as defined above is for medical use. Preferably, the compound, pharmaceutically acceptable salt, solvate or stereoisomer as defined above is for use in the treatment and/or prevention of an HBV infection and/or a condition related to an HBV infection. Preferably, said condition related to an HBV infection is selected from the group consisting of: chronic hepatitis B, HBV/HDV co-infection, HBV/HCV co-infection, HBV/HIV co-infection, inflammation, necrosis, cirrhosis, hepatocellular carcinoma, hepatic decompensation and hepatic injury from an HBV infection.

Even more preferably, the compound, pharmaceutically acceptable salt, solvate or stereoisomer as defined above is for use in treating, eradicating, reducing, slowing or inhibiting an HBV infection in an individual in need thereof, and/or in reducing the viral load associated with an HBV infection in an individual in need thereof, and/or in reducing reoccurrence of an HBV infection in an individual in need thereof, and/or in inducing remission of hepatic injury from an HBV infection in an individual in need thereof, and/or in prophylactically treating an HBV infection in an individual afflicted with a latent HBV infection.

Preferred compounds exhibit an HBV inhibition greater than 50% at the test concentration (ranging from 1.0 micromolar to 0.1 micromolar) and/or an $EC_{50}$, as defined hereinafter, lower than 0.5 micromolar. HBV inhibition indicates inhibition of HBV expression and/or replication. The inhibition activity of the compounds of the invention can be measured as described hereinafter or with any other technique known in the art.

Preferably, the compound, pharmaceutically acceptable salt, solvate or stereoisomer as defined above is for use in combination with at least one further therapeutic agent. Preferably, said use in combination comprises the administration of at least one further therapeutic agent.

It is also an object of the invention a pharmaceutical composition comprising the compound, pharmaceutically acceptable salt, solvate or stereoisomer as defined above, alone or in combination with at least one further therapeutic agent, and at least one pharmaceutically acceptable excipient.

Preferably, the at least one further therapeutic agent is an anti-HBV agent or HBV antiviral. More preferably, the at least one further therapeutic agent, anti-HBV agent or HBV antiviral is selected from the group consisting of: a therapeutic vaccine; an RNA interference therapeutic/antisense oligonucleotide; an immunomodulator; a STING agonist; a RIG-I modulator; a NKT modulator; an IL agonist; an interleukin or another immune acting protein; a therapeutic and prophylactic vaccine; an immune checkpoint modulator/inhibitor; an HBV entry inhibitor; a cccDNA modulator; an inhibitor of HBV protein expression; an agent targeting HBV RNA; a capsid assembly inhibitor/modulator; a core or X protein targeting agent; a nucleotide analogue; a nucleoside analogue; an interferon or a modified interferon; an HBV antiviral of distinct or unknown mechanism; a cyclophilin inhibitor; a sAg release inhibitor; a HBV polymerase inhibitor; a dinucleotide; a SMAC inhibitor; a HDV targeting agent; a viral maturation inhibitor; a reverse transcriptase inhibitor and an HBV RNA destabilizer or another small-molecule inhibitor of HBV protein expression; or a combination thereof.

Preferably, the therapeutic vaccine is selected from: HBsAG-HBIG, HB-Vac, ABX203, NASVAC, GS-4774, GX-110 (also known as HB-110E), CVI-HBV-002, RG7944 (also known as INO-1800), TG-1050, FP-02 (Hepsyn-B), AIC649, VGX-6200, KW-2, TomegaVax-HBV, ISA-204, NU-500, INX-102-00557, HBV MVA and PepTcell.

Preferably, the RNA interference therapeutic is a siRNA, a ddRNA or a shRNA. Preferably, the RNA interference therapeutic is selected from: TKM-HBV (also known as ARB-1467), ARB-1740, ARC-520, ARC-521, BB-HB-331, REP-2139, ALN-HBV, ALN-PDL, LUNAR-HBV, GS3228836 and GS3389404.

Preferably, the immunomodulator is a TLR agonist. Preferably the TLR agonist is a TLR7, TLR8 or TLR9 agonist. Preferably, the TLR7, TLR8 or TLR9 agonist is selected from: RG7795 (also known as RO-6864018), GS-9620, SM360320 (9-benzyl-8-hydroxy-2-(2-methoxy-ethoxy)adenine), AZD 8848 (methyl [3-({[3-(6-amino-2-butoxy-8-oxo-7,8-dihydro-9H-pyrin-9-yl)propyl][3-(4-morpholinyl)propyl]amino}methyl)phenyl]acetate) and ARB-1598.

Preferably, the RIG-I modulator is SB-9200. Preferably, the IL agonist or other immune acting protein is INO-9112 or recombinant IL12. Preferably, the immune checkpoint modulator/inhibitor is BMS-936558 (Opdivo (nivolumab)) or KEYTRUDA® (pembrolizumab). Preferably, the HBV entry inhibitor is Myrcludex B, IVIG-Tonrol or GC-1102.

Preferably, the cccDNA modulator is selected from: a direct cccDNA inhibitor, an inhibitor of cccDNA formation or maintenance, a cccDNA epigenetic modifier and an inhibitor of cccDNA transcription.

Preferably, the capsid assembly inhibitor/modulator, core or X protein targeting agent, direct cccDNA inhibitor, inhibitor of cccDNA formation or maintenance, or cccDNA epigenetic modifier is selected from: BAY 41-4109, NVR 3-778, GLS-4, NZ-4 (also known as W28F), Y101, ARB-423, ARB-199, ARB-596, AB-506, JNJ-56136379, ASMB-101 (also known as AB-V102), ASMB-103, CHR-101, CC-31326, AT-130 and RO7049389.

Preferably, the interferon or modified interferon is selected from: interferon alpha (IFN-α), pegylated interferon alpha (PEG-IFN-α), interferon alpha-2a, recombinant interferon alpha-2a, peginterferon alpha-2a (Pegasys), interferon alpha-2b (Intron A), recombinant interferon alpha-2b, interferon alpha-2b XL, peginterferon alpha-2b, glycosylated interferon alpha-2b, interferon alpha-2c, recombinant interferon alpha-2c, interferon beta, interferon beta-1a, peginterferon beta-1a, interferon delta, interferon lambda (IFN-λ), peginterferon lambda-1, interferon omega, interferon tau, interferon gamma (IFN-γ), interferon alfacon-1, interferon alpha-n1, interferon alpha-n3, albinterferon alpha-2b, BLX-883, DA-3021, PI 101 (also known as AOP2014), PEG-infergen, Belerofon, INTEFEN-IFN, albumin/interferon alpha 2a fusion protein, rHSA-IFN alpha 2a, rHSA-IFN alpha 2b, PEG-IFN-SA and interferon alpha biobetter. Particularly preferred are: peginterferon alpha-2a, peginterferon alpha-2b, glycosylated interferon alpha-2b, peginterferon beta-1a, and peginterferon lambda-1. More particularly preferred is peginterferon alpha-2a.

Preferably, the HBV antiviral of distinct or unknown mechanism is selected from: AT-61 ((E)-N-(1-chloro-3-oxo-1-phenyl-3-(piperidin-1-yl)prop-1-en-2-yl)benzamide), AT130 ((E)-N-(1-bromo-1-(2-methoxyphenyl)-3-oxo-3-(piperidin-1-yl)prop-1-en-2-yl)-4-nitrobenzamide), analogues thereof, REP-9AC (REP-2055), REP-9AC' (REP-2139), REP-2165 and HBV-0259.

Preferably, the cyclophilin inhibitor is selected from: OCB-030 (also known as NVP-018), SCY-635, SCY-575 and CPI-431-32.

Preferably, said HBV polymerase inhibitor is selected from: entecavir (Baraclude, Entavir), lamivudine (3TC, Zeffix, Heptovir, Epivir, and Epivir-HBV), telbivudine (Tyzeka, Sebivo), clevudine, besifovir, adefovir (hepsera), tenofovir. Preferably, tenofovir is in a salt form.

Preferably, tenofovir is in a salt form selected from: tenofovir disoproxil fumarate (Viread), tenofovir alafenamide fumarate (TAF), tenofovir disoproxil orotate (also known as DA-2802), tenofovir disopropxil aspartate (also known as CKD-390), AGX-1009, and CMX157.

Preferably, the dinucleotide is SB9200. Preferably, the SMAC inhibitor is Birinapant. Preferably, the HDV targeting agent is Lonafarnib.

Preferably, the HBV RNA destabilizer or other small-molecule inhibitor of HBV protein expression is RG7834 or AB-452.

Preferably, the at least one further therapeutic agent is an agent useful in the treatment and prevetion of hepatitis B. Preferably, the at least one further therapeutic agent is an anti-HDV agent, an anti-HCV agent and/or an anti-HIV agent.

Preferably, the at least one further therapeutic agent is selected from the group consisting of: HBV polymerase inhibitor, interferon, viral entry inhibitor, BAY 41-4109, reverse transcriptase inhibitor, a TLR-agonist, AT-61 ((E)-N-(1-chloro-3-oxo-1-phenyl-3-(piperidin-1-yl)prop-1-en-2-yl)benzamide), AT-130 ((E)-N-(1-bromo-1-(2-methoxyphenyl)-3-oxo-3-(piperidin-1-yl)prop-1-en-2-yl)-4-nitrobenzamide), and a combination thereof, wherein the HBV polymerase inhibitor is preferably at least one of Lamivudine, Entecavir, Tenofovir, Adefovir, Telbivudine, Clevudine; and wherein the TLR agonist is preferably selected from the group consisting of SM360320 (9-benzyl-8-hydroxy-2-(2-methoxy-ethoxy)adenine), AZD 8848 (methyl [3-({[3-(6-amino-2-butoxy-8-oxo-7,8-dihydro-9H-purin-9-yl)propyl][3-(4-morpholinyl)propyl]amino}methyl)phenyl] acetate) and a combination thereof.

Preferably, the compound of the invention is for use in combination with one, two or more further therapeutic agent(s) as defined above.

Preferably, the pharmaceutical composition of the invention comprises one, two or more further therapeutic agent(s) as defined above.

In a preferred embodiment, said pharmaceutical composition is for use in the treatment and/or prevention of an HBV infection and/or a condition related to an HBV infection, said condition related to an HBV infection being preferably selected from the group consisting of: chronic hepatitis B, HBV/HDV co-infection, HBV/HCV co-infection, HBV/HIV co-infection, inflammation, necrosis, cirrhosis, hepatocellular carcinoma, hepatic decompensation and hepatic injury from an HBV infection. Preferably, said pharmaceutical composition is for use in treating, eradicating, reducing, slowing or inhibiting an HBV infection in an individual in need thereof, and/or in reducing the viral load associated with an HBV infection in an individual in need thereof, and/or in reducing reoccurrence of an HBV infection in an individual in need thereof, and/or in inducing remission of hepatic injury from an HBV infection in an individual in need thereof, and/or in prophylactically treating an HBV infection in an individual afflicted with a latent HBV infection.

In an embodiment, the invention provides a kit comprising at least one pharmaceutically acceptable vial or container containing one or more doses of a compound of the invention or of a pharmaceutical composition of the invention and optionally a) instructions for use thereof in mammals and/or b) an infusion bag or container containing a pharmaceutically acceptable diluent.

It is a further object of the invention a method treating, ameliorating or preventing an HBV infection and related conditions, including chronic hepatitis B, HBV/HDV co-infection, HBV/HCV co-infection, HBV/HIV co-infection, inflammation, necrosis, cirrhosis, hepatocellular carcinoma, hepatic decompensation and hepatic injury from an HBV infection comprising administering to a subject a therapeutically effective amount of the compound as defined above.

It is a further object of the invention a process for the synthesis of the compound, pharmaceutically acceptable salt, solvate or stereoisomer as defined above, for instance according to the synthetic Schemes included in the Examples. In particular, the present invention provides a process for the synthesis of the compound, pharmaceutically acceptable salt, solvate or stereoisomer as defined above, said process comprising at least one of the following steps:

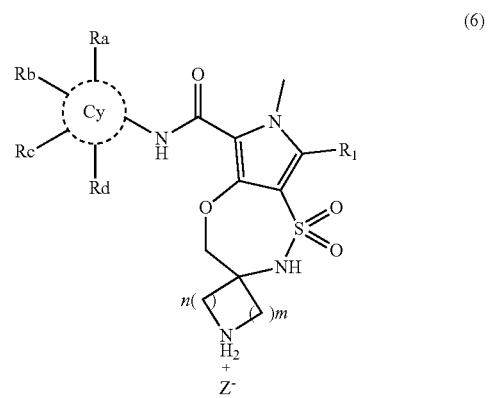

(6)

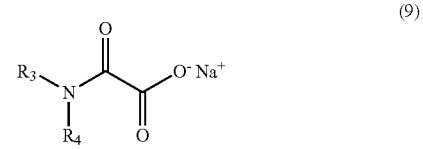

(9)

reacting a compound of formula (6) with an agent selected from the group consisting of: a compound of formula (9), an acid of formula $R_2COOH$ and an acyl chloride of formula $R_2COCl$;

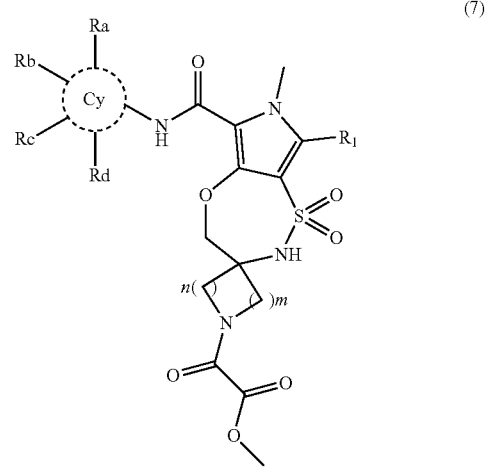

(7)

-continued (8)

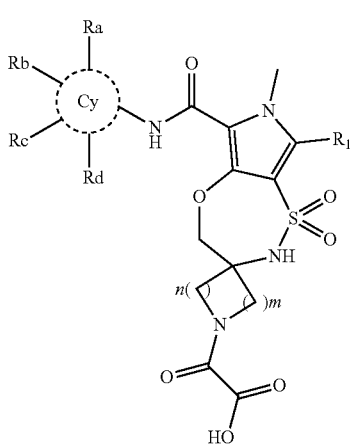

reacting a compound of formula (7) or (8) with an amine of formula NHR$_3$R$_4$;

said process optionally further comprising at least one of the following steps:

reacting a compound of formula (6) with methyl 2-chloro-2-oxoacetate to obtain a compound of formula (7);

hydrolyzing a compound of formula (7) in the presence of a base to obtain a compound of formula (8).

Reacting a compound of formula (6) with a compound of formula (9) may be performed under standard conditions, for instance in a polar solvent (e.g. DMF or EtOH) and/or in the presence of an organic base (e.g. DIPEA or DBU) and/or at RT.

Reacting a compound of formula (6) with an acid of formula R$_2$COOH may be performed under standard coupling conditions (see for example Chem. Soc. Rev., 2009, 38, 606-631).

Reacting a compound of formula (6) with an acyl chloride of formula R$_2$COCl may be performed under standard conditions, for instance in a polar aprotic solvent (e.g. MeCN) and/or in the presence of an organic base (e.g. TEA) and/or at a temperature from 0° C. to room temperature.

Reacting a compound of formula (7) or (8) with an amine of formula NHR$_3$R$_4$ may be performed under standard conditions, for instance under amide coupling conditions or by stirring the reagents at high temperature in a solvent like THF.

Compounds of formula (6), (7) or (8) may be prepared as described in the synthetic Schemes of the Examples.

In particular, reacting a compound of formula (6) with methyl 2-chloro-2-oxoacetate to obtain a compound of formula (7) may be performed under standard conditions, for instance in a polar aprotic solvent (e.g. MeCN) and/or in the presence of an organic base (e.g. DIPEA) and/or from 0° C. to RT.

Also in particular, hydrolyzing a compound of formula (7) in the presence of a base to obtain a compound of formula (8) may be performed under standard conditions, for instance by treatment with a base such as sodium hydroxide in a polar aprotic solvent (e.g. THF) and/or from 0° C. to RT.

It is a further object of the invention a pharmaceutical composition comprising an effective amount of one or more compounds as defined above or a pharmaceutically acceptable prodrug thereof, alone or in combination with other active compounds, and at least one pharmaceutically acceptable excipient.

The present invention includes within its scope prodrugs of the compounds of Formula (I), Formula (I-A), Formula (I-AA) above. In general, such prodrugs will be functional derivatives of the compounds of Formula (I), Formula (I-A) or Formula (I-AA) which are readily convertible in vivo into the required compound of Formula (I), Formula (I-A) or Formula (I-AA). Conventional procedures for the selection and preparation of suitable prodrug derivatives are described, for example, in "Design of Prodrugs", ed. H. Bundgaard, Elsevier, 1985.

A prodrug may be a pharmacologically inactive derivative of a biologically active substance (the "parent drug" or "parent molecule") that requires transformation within the body in order to release the active drug, and that has improved delivery properties over the parent drug molecule. The transformation in vivo may be, for example, as the result of some metabolic process, such as chemical or enzymatic hydrolysis of a carboxylic, phosphoric or sulphate ester, or reduction or oxidation of a susceptible functionality.

The invention also includes all suitable isotopic variations of a compound of the disclosure. Examples of isotopes that can be incorporated into compounds of the disclosure include isotopes such as $^2$H, $^3$H, $^{13}$C, $^{14}$C, $^{15}$N, $^{17}$O, $^{18}$O, $^{18}$F and $^{36}$Cl. Certain isotopic variations of the disclosure, for example, those in which a radioactive isotope such as $^3$H or $^{14}$C is incorporated, are useful in drug and/or substrate tissue distribution studies. Further, substitution with isotopes such as deuterium $^2$H, may afford certain therapeutic advantages resulting from greater metabolic stability.

Isotopic variations of the compounds of the disclosure can generally be prepared by conventional procedures such as by the illustrative methods or by the preparations described in the examples hereafter using appropriate isotopic variations of suitable reagents.

The present invention includes within its scope solvates of the compounds of Formula (I), Formula (I-A) or Formula (I-AA) or of the relative salts, for example, hydrates, alcoholates and the like.

In addition, the compounds disclosed herein may exist as tautomers and all tautomeric forms are intended to be encompassed by the scope of the invention, even though only one tautomeric structure is depicted.

The compounds of the present invention may have asymmetric centers, chiral axes, and chiral planes (as described in: E. L. Eliel and S. H. Wilen, *Stereochemistry of Carbon Compounds*, John Wiley & Sons, New York, 1994, pages 1119-1190), and occur as racemates, racemic mixtures, and as individual diastereomers, with all possible isomers and mixtures thereof, including optical isomers, all such stereoisomers being included in the present invention.

Pure stereoisomeric forms of the compounds and intermediates of this invention may be obtained by the application of art-known procedures and are intended to be encompassed by the scope of the invention. In particular, "pure stereoisomeric form" or "stereoisomerically pure" indicate a compound having stereoisomeric excess of at least 80%, preferably of at least 85%. For instance, enantiomers may be separated from each other by the selective crystallization of their diastereomeric salts or by chromatographic techniques using chiral stationary phases. Pure stereochemically isomeric forms may also be derived from the corresponding pure stereochemically isomeric forms of the appropriate starting materials, provided that the reaction occurs stereospecifically. The term "enantiomerically pure" shall be interpreted in a similar way, having regard to the enantiomeric ratio.

When any variable (e.g. $R_1$ and $R_2$, etc.) occurs more than one time in any constituent, its definition on each occurrence is independent at every other occurrence. Also, combinations of substituents and variables are permissible only if such combinations result in stable compounds. Lines drawn into the ring systems from substituents represent that the indicated bond may be attached to any of the substitutable ring atoms. If the ring system is polycyclic, it is intended that the bond be attached to any of the suitable carbon atoms on the proximal ring only.

It is understood that substituents and substitution patterns on the compounds of the instant invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results. The phrase "optionally substituted" should be taken to be equivalent to the phrase "unsubstituted or substituted with one or more substituents" and in such cases the preferred embodiment will have from zero to three substituents. More particularly, there are zero to two substituents.

The expression "one or more substituents" refers in particular to 1, 2, 3, 4 or more substituents, in particular to 1, 2, 3 or 4 substituents, more in particular 1, 2 or 3 substituents.

As used herein, "alkyl" is intended to include both branched and straight-chain saturated aliphatic hydrocarbon groups having the specified number of carbon atoms. For example, "$C_{1-6}$alkyl" is defined to include groups having 1, 2, 3, 4, 5 or 6 carbons in a linear or branched arrangement and specifically includes methyl, ethyl, n-propyl, i-propyl, n-butyl, t-butyl, i-butyl, pentyl, hexyl, and so on. Preferably, "$C_{1-6}$alkyl" refer to "$C_{1-4}$alkyl" or "$C_{1-3}$alkyl". More preferably, "$C_{1-6}$alkyl" or "$C_{1-3}$alkyl" refer to methyl.

As used herein, "alkoxy" represents an alkyl group of indicated number of carbon atoms attached through an oxygen bridge. "Alkoxy" therefore encompasses the definitions of alkyl above.

Preferably, alkoxy refers to a linear or branched $C_{1-6}$ alkoxy group, $C_{1-4}$ alkoxy group $C_{1-6}$alkoxy group, or $C_{1-2}$ alkoxy group. Examples of suitable alkoxy groups include, but are not limited to, methoxy, ethoxy, n-propoxy, i-propoxy, n-butoxy, s-butoxy or t-butoxy. Preferred alkoxy groups include methoxy, ethoxy and t-butoxy.

As used herein, the terms "halo$C_{1-6}$alkyl" and "halo$C_{1-6}$alkoxy" mean a $C_{1-6}$alkyl or $C_{1-6}$alkoxy group in which one or more (in particular, 1 to 3) hydrogen atoms have been replaced by halogen atoms, especially fluorine or chlorine atoms. Halo$C_{1-6}$alkoxy group is preferably a linear or branched halo$C_{1-4}$alkoxy group, more preferably a halo$C_{1-6}$ alkoxy group, still more preferably a halo$C_{1-2}$alkoxy group, for example $OCF_3$, $OCHF_2$, $OCH_2F$, $OCH_2CH_2F$, $OCH_2CHF_2$ or $OCH_2CF_3$, and most especially $OCF_3$ or $OCHF_2$. Halo$C_{1-6}$alkyl group is preferably a linear or branched halo$C_{1-4}$alkyl group, more preferably a halo$C_{1-3}$ alkyl group, still preferably a halo$C_{1-2}$alkyl group, for example, $CF_3$, $CHF_2$, $CH_2F$, $CH_2CH_2F$, $CH_2CHF_2$, $CH_2CF_3$ or $CH(CH_3)CF_3$. Still preferably, any one of halo$C_{1-6}$alkyl, halo$C_{1-4}$alkyl group, halo$C_{1-3}$alkyl group refers to: $CF_3$, $CHF_2$, $CH(CH_3)CF_3$, $CH_2CF_3$ or $(CH_3)_2CF_3$.

As used herein, the term "hydroxy$C_{1-6}$alkyl" means a $C_{1-6}$alkyl group in which one or more (in particular, 1 to 3) hydrogen atoms have been replaced by hydroxy groups. Illustrative examples include, but are not limited to $CH_2OH$, $CH_2CH_2OH$, $CH(CH_3)OH$ and $CHOHCH_2OH$.

As used herein, the term "aryl" means a monocyclic or polycyclic aromatic ring comprising carbon atoms and hydrogen atoms. If indicated, such aromatic ring may include one or more heteroatoms, then also referred to as "heteroaryl". Illustrative examples of heteroaryl groups according to the invention include 5 or 6 membered heteroaryl such as thiophene, oxazole, oxadiazole, thiazole, thiadiazole, imidazole, pyrazole, pyrimidine, pyrazine and pyridine. A preferred aryl according to the present invention is phenyl. A preferred heteroaryl according to the present invention is pyridyl. Further preferred 5 membered heteroaryl rings are oxadiazole and oxazole. Said oxadiazole is preferably substituted with one methyl group.

As used herein, the term "$C_{3-5}$cycloalkyl" means saturated cyclic hydrocarbon (cycloalkyl) with 3, 4 or 5 carbon atoms and is generic to cyclopropyl, cyclobutyl or cyclopentyl. Said saturated ring optionally contains one or more heteroatoms (also referred to as "heterocyclyl" or "heterocyclic ring" or "heterocycloalkyl"), such that at least one carbon atom is replaced by a heteroatom selected from N, O and S, in particular from N and O. Preferably, said $C_{3-5}$cycloalkyl is cyclopropyl.

As used herein, the term "halogen" refers to fluorine, chlorine, bromine and iodine, of which fluorine, chlorine and bromine are preferred. In particular, fluorine and chlorine are preferred for the halogen in position Ra, Rb, Rc or Rd. Also in particular, chlorine is preferred for the halogen in position $R_1$. Still in particular, fluorine is preferred for the halogen which is the substituent of the $C_{3-5}$-cycloalkyl or of the cyclic amine.

The term "heteroatom" refers to an atom other than carbon or hydrogen in a ring structure or a saturated backbone as defined herein. Typical heteroatoms include N(H), O, S.

Included in the instant invention is the free base of compounds of Formula (I), (I-A), (I-AA) as well as the pharmaceutically acceptable salts and stereoisomers thereof. Some of the specific compounds exemplified herein are the protonated salts of amine compounds. Compounds of Formula (I), (I-A), (I-AA) containing one or more N atoms may be protonated on any one, some or all of the N atoms. The term "free base" refers to the amine compounds in non-salt form. The encompassed pharmaceutically acceptable salts not only include the salts exemplified for the specific compounds described herein, but also all the typical pharmaceutically acceptable salts of the free form of compounds of Formula (I), (I-A), (I-AA). The free form of the specific salt compounds described may be isolated using techniques known in the art. For example, the free form may be regenerated by treating the salt with a suitable dilute aqueous base solution such as dilute aqueous NaOH, potassium carbonate, ammonia and sodium bicarbonate. The free forms may differ from their respective salt forms somewhat in certain physical properties, such as solubility in polar solvents, but the acid and base salts are otherwise pharmaceutically equivalent to their respective free forms for purposes of the invention.

The pharmaceutically acceptable salts of the instant compounds can be synthesized from the compounds of this invention which contain a basic or acidic moiety by conventional chemical methods. Generally, the salts of the basic compounds are prepared either by ion exchange chromatography or by reacting the free base with stoichiometric amounts or with an excess of the desired salt-forming inorganic or organic acid in a suitable solvent or various combinations of solvents. Similarly, the salts of the acidic compounds are formed by reactions with the appropriate inorganic or organic base. In a preferred embodiment, the compounds of the invention have at least one acidic proton and the corresponding sodium or potassium salt can be formed, for example, by reaction with the appropriate base.

Thus, pharmaceutically acceptable salts of the compounds of this invention include the conventional non-toxic salts of the compounds of this invention as formed by reacting a basic instant compound with an inorganic or organic acid or an acid compound with an inorganic or organic base. For example, conventional non-toxic salts include those derived from inorganic acids such as hydrochloric, hydrobromic, sulfuric, sulfamic, phosphoric, nitric and the like, as well as salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxy-benzoic, fumaric, toluenesulfonic, methanesulfonic, ethane disulfonic, oxalic, isethionic, trifluoroacetic and the like. Conventional non-toxic salts further include those derived from an inorganic base, such as potassium, sodium hydroxide, magnesium or calcium hydroxide, as well as salts prepared from organic bases, such as ethylene diamine, lysine, tromethamine, meglumine and the like. Preferably, a pharmaceutically acceptable salt of this invention contains one equivalent of a compound of Formula (I), Formula (I-A) or Formula (I-AA) and 1, 2 or 3 equivalent of an inorganic or organic acid or base. More particularly, pharmaceutically acceptable salts of this invention are the tartrate, trifluoroacetate or the chloride salts.

When the compound of the present invention is acidic, suitable "pharmaceutically acceptable salts" refers to salts prepared from pharmaceutically acceptable non-toxic bases including inorganic bases and organic bases. Salts derived from inorganic bases include aluminum, ammonium, calcium, copper, ferric, ferrous, lithium, magnesium, manganic salts, manganous, potassium, sodium, zinc and the like. Particularly preferred are the ammonium, calcium, magnesium, potassium and sodium salts. Salts derived from pharmaceutically acceptable organic non-toxic bases include salts of primary, secondary and tertiary amines, substituted amines including naturally occurring substituted amines, cyclic amines and basic ion exchange resins, such as arginine, betaine caffeine, choline, $N,N^1$-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine tripropylamine, tromethamine and the like.

The preparation of the pharmaceutically acceptable salts described above and other typical pharmaceutically acceptable salts is more fully described by Berg et al., "Pharmaceutical Salts," *J. Pharm. Sci.*, 1977:66:1-19.

It will also be noted that the compounds of the present invention are potentially internal salts or zwitterions, since under physiological conditions a deprotonated acidic moiety in the compound, such as a carboxyl group, may be anionic, and this electronic charge might then be balanced off internally against the cationic charge of a protonated or alkylated basic moiety, such as a quaternary nitrogen atom.

The compounds of the present invention find use in a variety of applications for human and animal health. The compounds of the present invention are inhibitors of hepatitis B virus (HBV).

In the context of the present invention, HBV may be any known isoltate, genotype, strain, etc. of HBV. In particular, the hepatitis B virus has been classified into eight main genotypes (designated A-H), and two additional genotypes (I and J) were tentatively proposed. HBV genotypes have been further separated into several subgenotypes that differ by 4.0 to 7.5% in the whole nucleotide sequence. HBV genotypes differ substantially in many virological and probably some clinical parameters; however, the precise role of HBV genotypes in the evolution of the infection remains controversial. Due to geographical distribution, only two or three HBV genotypes co-circulate in most regions of the world, thereby limiting genotype comparisons.

The compounds of the present invention are inhibitors of hepatitis B virus (HBV) useful for the treatment and/or prevention of an HBV infection. In particular the compounds of the present invention are inhibitors of hepatitis B virus (HBV) core (HBc) protein useful for the treatment and/or prevention of an HBV infection.

The compounds, compositions and methods provided herein are particularly deemed useful for treating, ameliorating or preventing an HBV infection and related conditions, including chronic hepatitis B, HBV/HDV co-infection, HBV/HCV co-infection, HBV/HIV co-infection, inflammation, necrosis, cirrhosis, hepatocellular carcinoma, hepatic decompensation and hepatic injury from an HBV infection.

In the present invention, the expression "HBV infection" comprises any and all conditions deriving from infection with HBV, including but not limited to hepatitis B, preferably chronic hepatitis B, HBV/HDV co-infection, HBV/HCV coinfection, HBV/HIV coinfection.

HBV infection leads to a wide spectrum of hepatic complications, all of these are intended as conditions related to an HBV infection. As used herein, "condition related to an HBV infection" is preferably selected from the group consisting of: hepatitis B, chronic hepatitis B, HBV/HDV co-infection, HBV/HCV co-infection, HBV/HIV co-infection, inflammation, necrosis, cirrhosis, hepatocellular carcinoma, hepatic decompensation and hepatic injury from an HBV infection.

Expressions like "treating, eradicating, reducing, slowing or inhibiting an HBV infection" are used to indicate the application or administration of a therapeutic agent, i.e., a compound of the invention (alone or in combination with another pharmaceutical agent), to a patient or application or administration of a therapeutic agent to an isolated tissue or cell line from a patient (e.g., for diagnosis or ex vivo applications), who has an HBV infection, a symptom of an HBV infection or the potential to develop an HBV infection, with the purpose to cure, heal, alleviate, relieve, alter, remedy, ameliorate, improve or affect an HBV infection, the symptoms of an HBV infection, or the potential to develop an HBV infection. Such treatments may be specifically tailored or modified, based on knowledge obtained from the field of pharmacogenomics.

Efficacy of treatment may be determined using quantification of viral load or other evidence of infection, such as through measurement of HBeAg, HBsAg, HBV DNA levels, ALT activity levels, serum HBV levels, and the like, thereby allowing adjustment of treatment dose, treatment frequency, and treatment length.

HBeAg stands for hepatitis B e-antigen. This antigen is a protein from the hepatitis B virus that circulates in infected blood when the virus is actively replicating.

ALT stands for Alanine Transaminase and is an enzyme involved in the transfer of an amino group from the amino-acid alanine to alpha-ketoglutaric acid to produce glutamate and pyruvate. ALT is located primarily in liver and kidney, with lesser amounts in heart and skeletal muscle. ALT is commonly measured clinically as part of liver function tests.

The compounds of the invention can reduce viral load in an individual suffering from an HBV infection. In a non limiting embodiment, the compounds of the invention result in viral load reduction during therapy in an individual in need thereof from a minimum of one- or two-log decrease to a maximum of about eight-log decrease.

As used herein, the expression "remission of hepatic injury from an HBV infection" means that the chronic necroinflammatory liver disease has been halted by the fact that the viral antigens have disappeared from the organ (and the immune system no longer attacks the liver cells).

As used herein, the term "prophylactically treating" means no disorder or disease development if none had occurred, or no further disorder or disease development if there had already been development of the disorder or disease. Also considered is the ability of one to prevent some or all of the symptoms associated with the disorder or disease. An example of prophylactic treatment might also indicate the necessity of reducing the risk of infecting a liver graft (in case of liver transplant in chronically infected patients) or infecting newborns (in case of chronically infected mothers that pass the virus at time of delivery).

As used herein, "reducing reoccurrence of an HBV infection" indicates that patients may have reactivation of HBV replication and exacerbation of a condition related to an HBV infection, e.g. hepatitis, after years of quiescence. These patients may still be at risk of developing a condition related to an HBV infection, e.g. hepatocellular carcinoma development. Antiviral therapy is also recommended as prophylaxis for patients who are HBsAg-positive as well as patients who are HBsAg-negative and hepatitis B core antibody-positive who require treatment with immunosuppressive therapies that are predicted to have a moderate to high risk of HBV reactivation.

The compounds of this invention may be administered to mammals, preferably humans, either alone or in combination with pharmaceutically acceptable carriers, excipients or diluents, in a pharmaceutical composition, according to standard pharmaceutical practice. In one embodiment, the compounds of this invention may be administered to animals. The compounds can be administered orally or parenterally, including the intravenous, intramuscular, intraperitoneal, subcutaneous, rectal and topical routes of administration.

The invention also provides pharmaceutical compositions comprising one or more compounds of this invention and a pharmaceutically acceptable carrier. The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate butyrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethyleneoxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example *arachis* oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or *arachis* oil, or a mineral oil, for example liquid paraffin or mixtures of these. Suitable emulsifying agents may be naturally occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate.

The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulstion.

The injectable solutions or microemulsions may be introduced into a patient's blood stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, for example as a solution in 1,3-butanediol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound(s) of the invention are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

The compounds of the invention may be presented in a liposome or other micro particulate or other nanoparticle designed to target the compound. Acceptable liposomes can be neutral, negatively, or positively charged, the charge being a function of the charge of the liposome components and pH of the liposome solution. Liposomes can be normally prepared using a mixture of phospholipids and cholesterol. Suitable phospholipids include phosphatidylcholine, phosphatidylethanolamine, phosphatidic acid, phosphotidylglycerol, phosphatidylinositol.

Polyethylene glycol can be added to improve the blood circulation time of liposomes. Acceptable nanoparticles include albumin nanoparticles and gold nanoparticles.

When a compound according to this invention is administered into a human subject, the daily dosage will normally be determined by the prescribing physician with the dosage generally varying according to the age, weight, sex and response of the individual patient, as well as the severity of the patient's symptoms.

In one exemplary application, a suitable amount of compound is administered to a mammal undergoing anti HBV treatment. Administration generally occurs in an amount between about: 0.01 mg/kg of body weight to about 100 mg/kg of body weight per day, preferably between about 0.01 mg/kg of body weight to about 60 mg/kg of body weight per day, preferably between about 0.1 mg/kg of body weight to about 50 mg/kg of body weight per day, preferably between about 0.5 mg/kg of body weight to about 40 mg/kg of body weight per day.

The instant compounds are also useful in combination with known therapeutic agents for simultaneous, separate or sequential administration.

In an embodiment, the compounds of the present invention may be used in combination with at least one or more additional therapeutic agents, in particular anti-HBV agents.

The indication that compounds of the invention are for use in the treatment and/or prevention of an HBV infection indicates that the compounds are efficacious for treating, eradicating, reducing, slowing or inhibiting an HBV infection.

The therapeutic agent is any agent commonly used in the treatment and/or prevention and/or amelioration of an HBV infection or a condition related to an HBV infection. The therapeutic agent is known in the art.

The term "anti-HBV agent", or more simply "HBV antiviral(s)" also includes compounds that are therapeutic nucleic acids, antibodies or proteins either in their natural form or chemically modified and/or stabilized. The hepatitis B virus (HBV) strain may be resistant to at least one anti-HBV agents, then also defined as "drug-resistant". The term therapeutic nucleic acid includes but is not limited to nucleotides and nucleosides, oligonucleotides, polynucleotides, of which non limiting examples are antisense oligonucleotides, miRNA, siRNA, shRNA, therapeutic vectors and DNA/RNA editing components.

The term anti-HBV agent also includes compounds capable of treating an HBV infection via immunomodulation, i.e. immunomodulators or immunomodulating compounds. Examples of immunomodulators are interferon-α (IFN-α), pegylated interferon-α or stimulants of the innate immune system such as Toll-like receptor 7 and/or 8 agonists and therapeutic or prophylactic vaccines. One embodiment of the present invention relates to combinations of a compound of Formula (I), (I-A), (I-AA) or any subgroup thereof, as specified herein, with an immunomodulating compound, more specifically a Toll-like receptor 7 and/or 8 agonist.

The additional HBV antiviral(s) can be selected for example, from therapeutic vaccines; RNA interference therapeutic/antisense oligonucleotides (e.g. siRNA, ddRNA, shRNA); immunomodulators (such as TLR agonists (e.g. TLR7, TLR8 or TLR9 agonists); STING agonists; RIG-I modulators; NKT modulators; IL agonists; Interleukin or other immune active proteins, therapeutic and prophylactic vaccines and immune checkpoint modulators; HBV entry inhibitors; cccDNA modulators (such as for example direct cccDNA inhibitors, inhibitors of cccDNA formation or maintenance, cccDNA epigenetic modifiers, inhibitors of cccDNA transcription); inhibitors of HBV protein expression; agents targeting HBV RNA; capsid assembly inhibitors/modulators; core or X protein targeting agents; nucleotide analogues; nucleoside analogues; interferons or modified interferons; HBV antivirals of distinct or unknown mechanism; cyclophilin inhibitors; sAg release inhibitors; HBV polymerase inhibitors; dinucleotides; SMAC inhibitors; HDV targeting agents; viral maturation inhibitors; reverse transcriptase inhibitors and HBV RNA destabilizers and other small-molecule inhibitors of HBV protein expression.

In particular, the combination of previously known anti-HBV agents, such as interferon-α (IFN-α), pegylated interferon-α, 3TC, tenofovir, lamivudine, entecavir, telbivudine, and adefovir or a combination thereof, and a compound of Formula (I), (I-A), (I-AA) or any subgroup thereof can be used as a medicine in a combination therapy. Additional examples of further therapeutic agents that may be combined with the compounds of the present invention include: Zidovudine, Didanosine, Zalcitabine, Stavudine, Abacavir, ddA Emtricitabine, Apricitabine, Atevirapine, ribavirin, acyclovir, valacyclovir, famciclovir, ganciclovir, valganciclovir, cidofovir, Efavirenz, Nevirapine, Delavirdine and Etravirine.

The term "administration" and variants thereof (e.g., "administering" a compound) in reference to a compound of the invention means introducing the compound or a prodrug of the compound into the system of the animal in need of treatment. When a compound of the invention or prodrug thereof is provided in combination with one or more other active agents (e.g., a cytotoxic agent, etc.), "administration" and its variants are each understood to include concurrent and sequential introduction of the compound or prodrug thereof and other agents.

In some embodiments, pulsed administration is more effective than continuous treatment because total pulsed doses are often lower than would be expected from continuous administration of the same composition. Each pulse dose can be reduced and the total amount of drug administered over the course of treatment is minimized. Individual pulses can be delivered to the patient continuously over a period of several hours, such as about 2, 4, 6, 8, 10, 12, 14 or 16 hours, or several days, such as 2, 3, 4, 5, 6 or 7 days.

As used herein, the term "composition" is intended to encompass a product comprising the specified ingredients in the specified amounts, as well as any product which results, directly or indirectly, from combination of the specified ingredients in the specified amounts.

The term "therapeutically effective amount" as used herein means that amount of active compound or pharmaceutical agent that elicits the biological or medicinal response in a tissue, system, animal or human that is being sought by a researcher, veterinarian, medical doctor or other clinician.

The present invention will be described by means of the following non-limiting examples and biological data.

Materials and Methods

Chemistry
General

Unless otherwise indicated, commercially available reagents and solvents (HPLC grade) were used without further purification.

Specifically, the following abbreviations may have been used in the descriptions of the experimental methods:

NMR: Nuclear Magnetic Resonance; $^1$H: proton; MHz: Megahertz; Hz: Hertz; HPLC: High Performance Liquid Chromatography; LC-MS: Liquid Chromatography Mass Chromatography Spectrum; s: second(s); min: minute(s); h or hr: hour(s); mg: milligram(s); g: gram(s); Ml: microliter(s); mL: millilitre(s); mmol: millimole(s); nm: nanometer(s) M: micromolar; M: molarity or molar concentration; Rt: retention time in minutes; anh: anhydrous; ss: saturated solution; aq: aqueous; sat.aq.: saturated aqueous solution; MW: microwave; Boc: tert-butyloxycarbonyl protecting group; DCM: dichloromethane; DIAD: Diisopropyl azodicarboxylate; DMF: dimethylformamide; DIPEA: N,N-diisopropylethylamine; DMSO: dimethylsulfoxide; EtOH: ethanol; EtOAc: ethyl acetate; IPA: isopropylamine; LiHMDS: Lithium bis(trimehtylsilyl)amide; MeOH: methanol; MeCN: Acetonitrile; PE: Petroleum Ether; PMB: p-methoxybenzyl protecting group; PyBop: Benzotriazole-1-yl-oxy-tris-pyrrolidino-phosphonium hexafluorophosphate; TFA: trifluoroacetic acid; eq.: equivalent(s); RT: room temperature; TBDMS: tert-butyldimethylsilyl; TEA: triethylamine; THF: tetrahydrofuran; pTSA: para-toluene sulfonic acid; TBTU: 2-(1H-Benzotriazole-1-yl)-1,1,3,3-tetramethylaminium tetrafluoroborate. Except where indicated otherwise, all temperatures are expressed in ° C. (degrees centigrade) or K (Kelvin).

The $^1$H-NMR spectra were acquired with an Avance II 300 MHz Bruker spectrometer. The chemical shifts are expressed in parts per million (ppm, δ units). The coupling constants are expressed in Hertz (Hz) and the splitting patterns are described as s (singlet), bs (broad signal), d (doublet), t (triplet), q (quartet), quint (quintet), m (multiplet).

The LC-MS analyses were performed by means of an UPLC Acquity Waters System equipped with the SQD spectrometer, single quadrupole mass detector, and a TUV detector, using column 1: ACQUITY UPLC BEH SHIELD, RPis (2.1×50 mm, id=1.7 µm); column2: ACQUITY UPLC HSS T3, RP$_{18}$ (2.1×50 mm, id=1.8 µm) and column3: ACQUITY UPLC BEH SHIELD, RP$_{18}$ (2.1×100 mm, id=1.7 µm). Column temperature 40° C. Sample temperature 25° C. Phase A was composed by water (HiPerSolv Chromanorm Water VWR for HPLC-MS)+0.05% Trifluoroacetic Acid; Phase B by CH$_3$CN (HiPerSolv Chromanorm Acetonitrile SuperGradient VWR, suitable for UPLC/UHPLC instruments)+0.05% Trifluoroacetic Acid; flow rate: 0.5 mL/min; UV detection (DIODE array) 200 nm; ESI+ and ESI− detection in the 100-1000 m/z range.

Method 1: column 1, run time: 3 minutes, run gradient: 5% B to 100% B in 2.80 min+100% B for 0.2 min, equilibration time: 0.8 min, ionization mode: ESI$^+$.

Method 2: column 2, run time: 4 minutes, run gradient: 0% B to 45% B in 3.5 min+45% B to 100% B in 0.05 min+100% B for 0.45 min, equilibration time: 0.8 min, ionization mode: ESI$^+$.

Method 3: column 3, run time: 6 minutes, run gradient: 5% B to 100% B in 5 min+100% B for 1 min, equilibration time: 2 min.

Method 4: column 3, run time: 6 minutes, run gradient: 5% B to 50% B in 5 min+50% B to 100% B in 0.2 min 100% B for 0.8 min, equilibration time: 2 min, ionization mode: ESI$^+$.

Method 5: column 1, run time: 3 minutes, run gradient: 5% B to 100% B in 2.80 min+100% B for 0.2 min, equilibration time: 0.8 min, ionization mode: ESI$^+$.

Method 6: column 2, run time: 4 minutes. run gradient: 0% B to 45% B in 3.5 min+45% B to 100% B in 0.05 min+100% B for 0.45 min. Equilibration time: 0.8 min, ionization mode: ESI$^+$.

Method 7: column 3, run time: 6 minutes, run gradient: 5% B to 100% B in 5 min+100% B for 1 min, equilibration time: 2 min, ionization mode: ESI$^+$.

Method 8: column 3, run time: 6 minutes, run gradient: 5% B to 50% B in 5 min+50% B to 100% B in 0.2 min 100% B for 0.8 min, Equilibration time: 2 min, ionization mode: ESI+.

Method 9: column 1. run time: 4 minutes, column 1, run time: 4 minutes, run gradient: 5% B to 100% B in 3.00 min+100% B for 1 min, equilibration time: 0.8 min, ionization mode: ESI+.

Method 10: column 1. run time: 4 minutes, run gradient: 5% B to 100% B in 3.00 min+100% B for 1 min, equilibration time: 0.8 min, Ionization Mode: ESI−.

Method 11: column 1, run time: 3 minutes, run gradient: 40% B to 100% B in 2.80 min+100% B for 0.2 min, equilibration time: 0.8 min. Ionization Mode: ESI+.

Method 12: column 3, run time: 6 minutes, run gradient: 25% B to 70% B in 5 min+100% B for 1 min, equilibration time: 2 min, Flow: 0.5 mL/min, ionization mode: ESI+.

Method 13: column 2, run time: 4 minutes, run gradient: 0% B to 60%$_B$ in 3.5 min+60% B to 100% B in 0.05 min+100% B for 0.45 min, equilibration time: 0.8 min, ionization mode: ESI+.

Method 14: column 2, run time: 4 minutes, run gradient: 0% B to 30% B in 3.5 min+30% B to 100% B in 0.05 min+100% B for 0.45 min, equilibration time: 0.8 min, ionization mode: ESI+.

Synthesis

According to a further aspect of the invention there is provided a process for the preparation of compounds of Formula (I) or salts thereof. The following schemes are examples of synthetic schemes that may be used to synthesise the compounds of the invention. In the following schemes reactive groups can be protected with protecting groups and deprotected according to well established techniques. In the following schemes and paragraphs $R_1$, $R_2$, $R_3$, $R_4$, Ra, Rb, Rc, Rd, Cy, n and m are as defined herein above in Formula (I).

It will be understood by those skilled in the art that certain compounds of the invention can be converted into other compounds of the invention according to standard chemical methods.

Compounds of the invention may be prepared according to the general routes indicated in the following Scheme 1 and Scheme 2:

Scheme 1

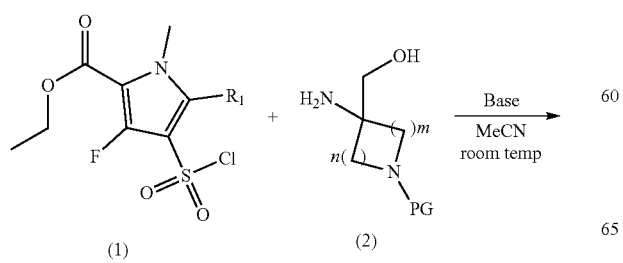

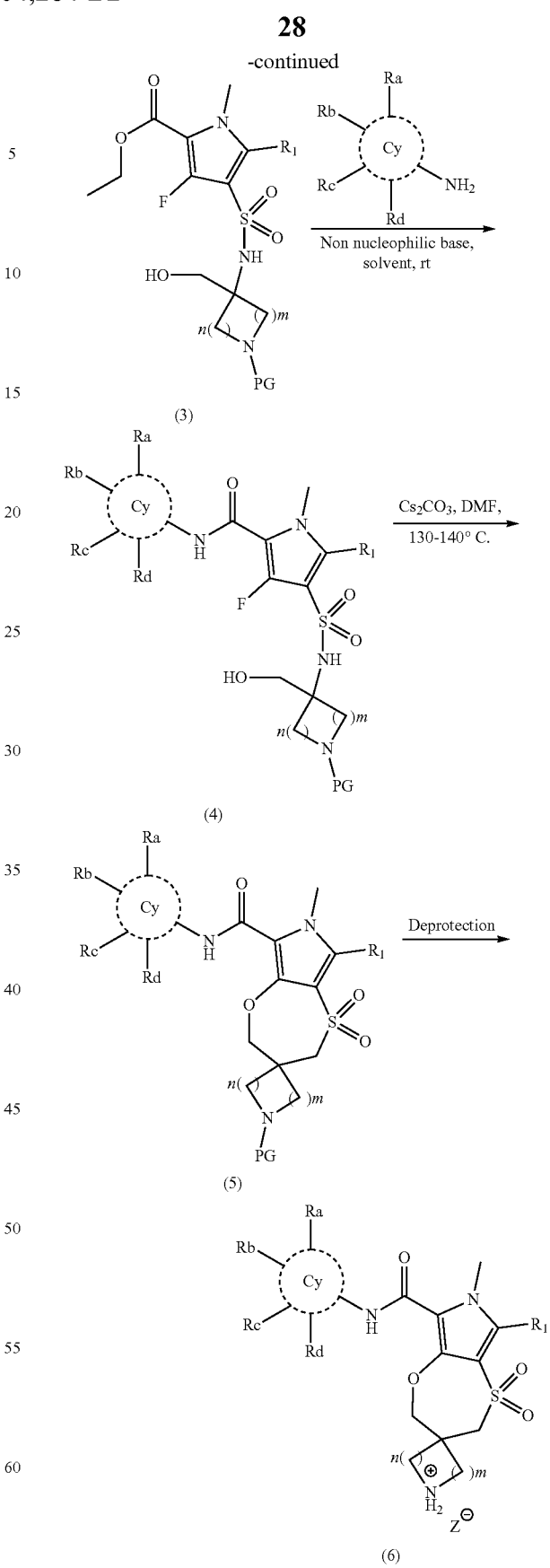

PG = Protecting Group (Boc, CBz, COOEt, . . . )
Z− = Cl−, Br−, CF$_3$COO−, pTolSO$_3$− . . .

Ethyl 4-(chlorosulfonyl)-3-fluoro-1-methyl-1H-pyrrole-2-carboxylate, indicated as compound (1) in Scheme 1 with $R_1$=H, was prepared according to the procedure described in WO2017/001655. According to Scheme 1, the primary amine derivative (2) bearing a nucleophilic —OH substituent is reacted with the compound (1) in the presence of the appropriate base to give the corresponding sulphonamide product (3). Reaction of (3) with an arylamine or heteroarylamine in the presence of a strong non-nucleophilic base, such as LiHMDS, in a solvent like tethrahydrofuran, converts the ethyl carboxylate into an arylamide derivative (4). A subsequent cyclization step through intramolecular nucleophilic attack of the OH on the fluorine gives the tricyclic core of compound (5). Depending on the specific hydrogenation for the p-methoxybenzyl group (PMB). Still worth of specific note is that the specific sequence of steps indicated in Scheme 1 can be changed to optimize the efficiency of the synthetic strategy.

Deprotection of the compound (5) indicated in Scheme 1 affords the advanced intermediate of general structure (6), wherein Z is a counterion such as Cl⁻, $CF_3COO^-$, $pTolylSO_3^-$ or the like, indicated in Scheme 1. Compounds of Formula (6) are reacted with $R_2$—COOH or derivatives thereof, such as the acyl chlorides or the esters, under the appropriate coupling conditions to obtain the compounds of Formula (I). In particular, compounds of Formula (I) wherein $R_2$ is —(C=O)$NR_3R_4$ are obtained as indicated in Scheme 2.

Scheme 2

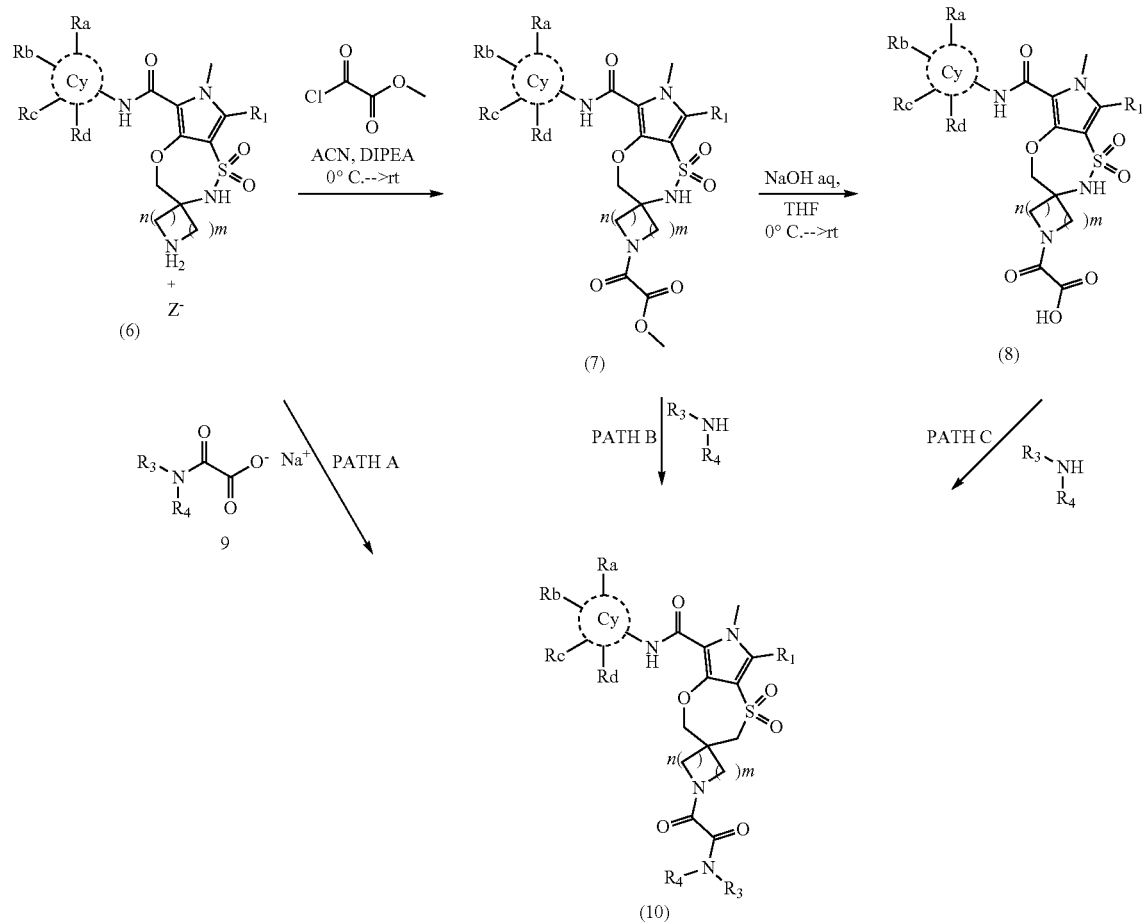

Protecting Group (PG, as indicated in Scheme 1) in compounds (5) the product can be further elaborated through deprotection and/or further functionalization steps. In particular, when the nitrogen is as the N-Boc derivative, the Boc can be removed by acidic treatment and the resulting NH can be further converted for example into an amide or oxalamide derivative or can be alkylated through, for example, reductive amination chemistry. In a particular embodiment of the invention, in a compound of general formula (5) the protected nitrogen is N-COOEt or N-PMB, wherein the Protecting Group can be cleaved through standard chemistry, such as trimethyl silyl iodide for the ethyl carbamate and A compound of Formula (I) wherein $R_1$ is H can be converted into a compound of Formula (I) wherein $R_1$ is halogen through standard halogenation methods (see for example Journal of Organic Chemistry (1981), 46(11), 2221-5).

The procedures in the schemes can be used for the synthesis of the compounds indicated below and can be used as well for the synthesis of the compounds as single diastereoisomers and/or enantiomers by choosing the starting materials with the appropriate stereochemical configuration.

Where not otherwise indicated, starting materials and/or intermediates were obtained from commercial sources or can be obtained through synthetic procedures known in the chemistry literature. The indication of the commercial source of certain compounds in the description of the experimental procedure, when provided, is only for easy reference to skilled chemist and should not be interpreted as the indication to use only that particular commercial compound.

In the following paragraphs, the Descriptions 1 to 28 illustrate the preparation of intermediates used to make compounds of the invention and salts thereof. The Examples illustrate the preparation of the compounds of the invention and salts thereof. Where the compounds have more than one chiral center, it is understood that they might exist as mixtures of diastereoisomers or as single isomers. Both racemic and chiral compounds are within the scope of the present invention.

The indicated procedures are provided merely for assistance to the skilled chemist. The starting material may not necessarily have been prepared from the batch of the Description or the Example referred to.

Description D1: rac-ethyl 4-(N-(1-(tert-butoxycarbonyl)-3-(hydroxymethyl)pyrrolidin-3-yl)sulfamoyl)-3-fluoro-1-methyl-1H-pyrrole-2-carboxylate (D1)

Compound D1 was prepared according to the Scheme below:

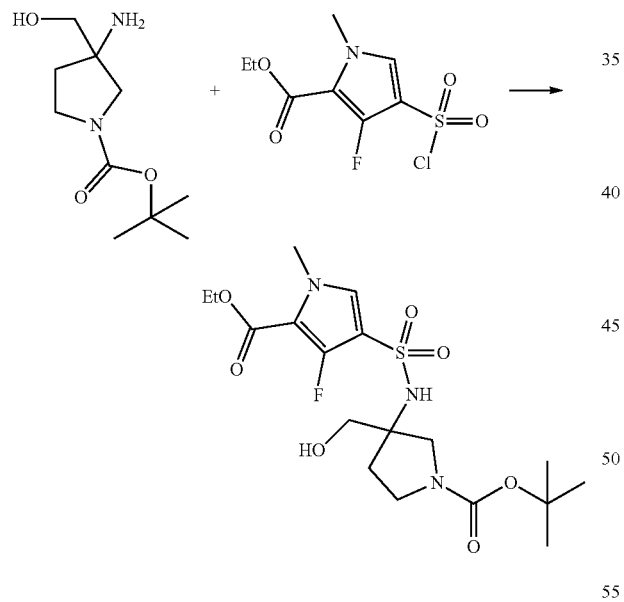

A solution of ethyl 4-(chlorosulfonyl)-3-fluoro-1-methyl-1H-pyrrole-2-carboxylate (100 mg, 0.37 mmol) and tert-butyl 3-amino-3-(hydroxymethyl)pyrrolidine-1-carboxylate (237078, Fluorochem, CAS: 889949-18-2; 80.2 mg, 0.37 mmol) in dry MeCN (2 mL) was treated with TEA (0.15 mL, 1.11 mmol). The reaction was stirred at RT for 30 min; then was concentrated under reduced pressure; diluted with EtOAc and washed with 5% citric acid solution and brine, dried over $Na_2SO_4$ (anh.), filtered and solvent removed under reduced pressure. The crude D1 (131 mg, 0.29 mmol, yield=78.6%) was used as such in the next synthetic step. Method 1: Rt=1.70 min; m/z=450.3 (M+H)$^+$.

Description D2: 6'-((3,4-difluorophenyl)carbamoyl)-7'-methyl-2'H,4'H,7'H-spiro[pyrrolidine-3,3'-pyrrolo[3,4-b][1,4,5]oxathiazepin]-1-ium 1',1'-dioxide chloride (D2)

Compound was prepared according to the Scheme below:

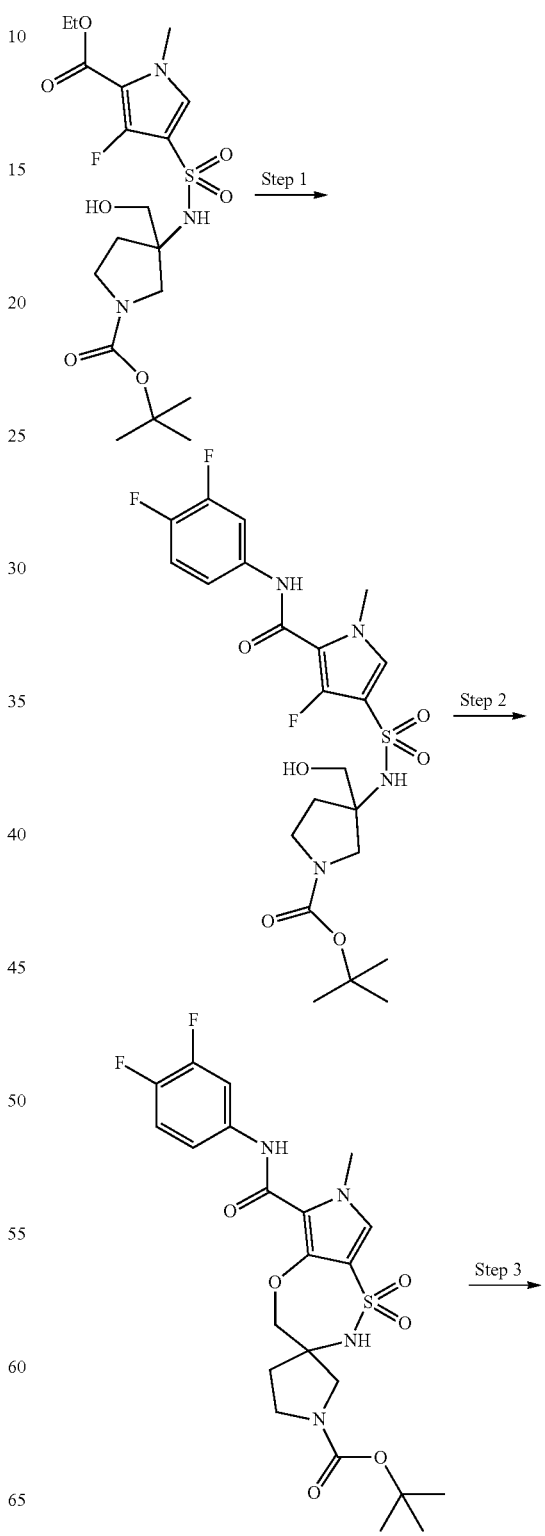

-continued

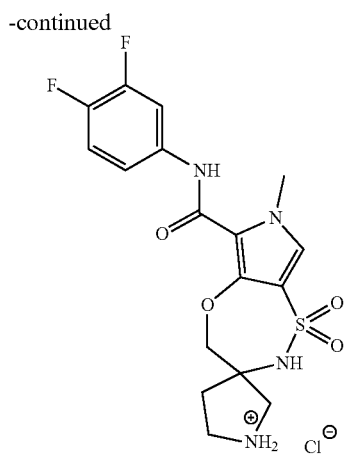

Step 1:
To a solution of D1 (130 mg, 0.29 mmol) and 3,4-difluoroaniline (001459, Fluorochem, CAS: 63-11-4; 30 μL, 0.304 mmol) in dry THF (3 mL), lithium bis(trimethylsilyl)amide (1 M in THF) (1.45 mL) was added dropwise at room temperature. After 60 min the reaction was quenched with water, diluted with DCM and washed with aq 5% citric acid and brine. The organic layer was dried over $Na_2SO_4$, filtered and concentrated under reduced pressure to afford tert-butyl 3-((5-((3,4-difluorophenyl)carbamoyl)-4-fluoro-1-methyl-1H-pyrrole)-3-sulfonamido)-3-(hydroxymethyl)pyrrolidine-1-carboxylate (154 mg, 0.289 mmol, quantitative yield) as a foam that was used without further purification. Method 1: Rt=1.98 min; m/z=533.4 (M+H)$^+$.

Step 2:
To a solution of compound from Step 1 (154 mg, 0.289 mmol) in DMF (2.9 mL) was added cesium carbonate (282.7 mg, 0.868 mmol), and the reaction mixture was stirred at 135° C. with oil bath for 1 h. Reaction was diluted with EtOAc and washed with water (×3). Organic layer was dried over $Na_2SO_4$ (anh.), filtered and concentrated under vacuo to yield tert-butyl 6'-((3,4-difluorophenyl)carbamoyl)-7'-methyl-2'H,4'H,7'H-spiro[pyrrolidine-3,3'-pyrrolo[3,4-b][1,4,5]oxathiazepine]-1-carboxylate 1',1'-dioxide (148 mg, 0.289 mmol, quantitative yield) as a solid. Method 1: Rt=2.19 min; m/z=513.2 (M+H)$^+$.

Step 3:
The compound from Step 2 (148 mg, 0.290 mmol) was dissolved in DCM (2 mL) and treated with a single portion of 1 M HCl in dioxane (0.29 mL, 0.290 mmol). After 1 h stirring at room temperature, solvent was removed giving D2 as hydrochloride salt (130 mg, quantitative yield) that was used in the next steps without any purification. Method 1: Rt=1.33 min; m/z=413.2 (M+H)$^+$.

Description D3: methyl (R)-2-oxo-2-((1,1,1-trifluoropropan-2-yl)amino)acetate (D3)

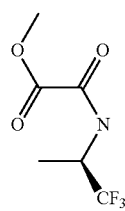

To an equimolar solution of (2R)-1,1,1-trifluoro-2-propanamine hydrochloride (U23940, AurumPharmacuticals, CAS: 177469-12-4; 500 mg, 3.34 mmol) and N-ethyl-N-isopropylpropan-2-amine (1.16 mL, 6.69 mmol) in DCM dry (3 mL, 0.047 mol), methyl 2-chloro-2-oxoacetate (0.31 mL, 3.34 mmol) was added dropwise at 0° C. and under nitrogen atmosphere. The reaction was stirred at 0° C. for 30 min, then was quenched with ice and water. The organic phase was washed with 1 N HCl (3×20 mL) and brine. The organic phase was dried over $Na_2SO_4$ (anh.), then was filtered and concentrated to yield D3 (567 mg, yield=85%) as a colorless solid, that was used in the next synthetic step as such. Method 1: Rt=1.12 min, m/z=200.1 (M+H)$^+$.

Description D4: Sodium (R)-2-oxo-2-((1,1,1-trifluoropropan-2-yl)amino)acetate (D4)

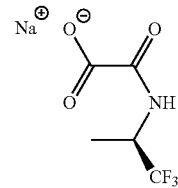

To a solution of D3 (567.mg, 2.85 mmol) in THF (2 mL, 0.025 mol), sodium hydroxide (113.89 mg, 2.85 mmol), previously dissolved in water (1 mL, 0.056 mol), was added at RT. The reaction was stirred at room temperature overnight, then was diluted with toluene (30 mL) and evaporated to dryness under reduced pressure. This procedure was repeated for 2 times to afford a white powder. The product was additionally dried under vacuum pump overnight to yield D4 (562 mg, yield=95%) as white powder. Method 13: Rt=1.25 min, m/z=130.1 (M+H)$^+$.

Description D5: tert-butyl (3R)-3-amino-3-(hydroxymethyl)pyrrolidine-1-carboxylate (D5)

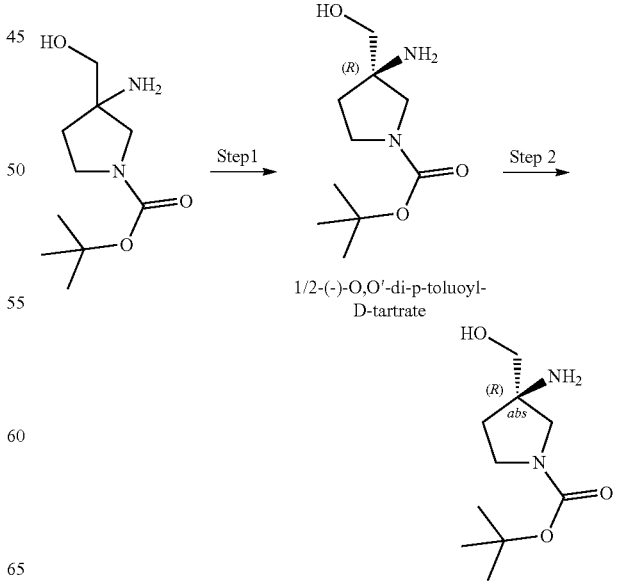

Step 1:

A mixture of tert-butyl 3-amino-3-(hydroxymethyl)pyrrolidine-1-carboxylate (Fluorochem, cat n° 237078, CAS: 889949-18-2) (500 mg, 2.31 mmol) and (−)-O,O'-di-p-toluoyl-D-tartrate (0.5 eq, 445 mg, 1.15 mmol) was suspended in IPA (2.5 mL, 0.033 mol) and the mixture was sonicated until mostly dissolved. The resultant suspension was heated at 65° C. for few minutes and sonicated again resulting in homogeneous mixture. The pale yellow solution was heated at 65° C. After 5 min, the mixture became a white suspension, and stirring was continued at 65-70° C. for 18 hrs. The suspension was allowed to cool to room temperature over 1 hr. The suspension was filtered, the solids were rinsed with small volume of isopropanol. The crude was dried under vacuum pump overnight to yield tert-butyl (3R)-3-amino-3-(hydroxymethyl)pyrrolidine-1-carboxylate-hemi-(−)-O,O'-di-p-toluoyl-D-tatrate (345 mg, 0.43 mmol, y=36.4%). $^1$H NMR (300 MHz, DMSO-$d_6$) δ ppm 1.39 (s, 9H) 1.62-1.79 (m, 1H) 1.79-2.03 (m, 1H) 2.35 (s, 3H) 3.03-3.51 (m, 6H) 5.57 (s, 1H) 6.83-8.03 (m, 1H) 7.28 (d, J=8.07 Hz, 2H) 7.80 (d, J=8.16 Hz, 1H).

Step 2:

tert-butyl (3R)-3-amino-3-(hydroxymethyl)pyrrolidine-1-carboxylate-hemi-(−)-O,O'-di-p-toluoyl-D-tartrate (350.mg, 0.43 mmol) was suspended in water (1 mL) and ethyl acetate (1 mL). The mixture was cooled in an ice bath and 6N HCl (0.14 mL, 0.840 mmol) was added dropwise. The resulting biphasic mixture was stirred at 0° C. for 1 hr. The layers were separated and the aqueous phase was washed with EtOAc (×1). The water layer was cooled to 0° C. and treated with 3M aq NaOH (0.28 mL, 0.840 mmol). The mixture was stirred at 0° C. for 1 hr. The resulting solution was extracted with MeTHF (5×10 mL) and concentrated under reduced pressure to give tert-butyl (3R)-3-amino-3-(hydroxymethyl)pyrrolidine-1-carboxylate (134 mg, 0.620 mmol) as a white solid. $^1$H NMR (300 MHz, CHLOROFORM-d) δ ppm 1.45 (s, 9H) 1.67-1.85 (m, 1H) 1.86-2.05 (m, 1H) 2.40 (br s, 2H) 3.14-3.59 (m, 6H).

Description D6: tert-butyl (3S)-3-amino-3-(hydroxymethyl)pyrrolidine-1-carboxylate (D6)

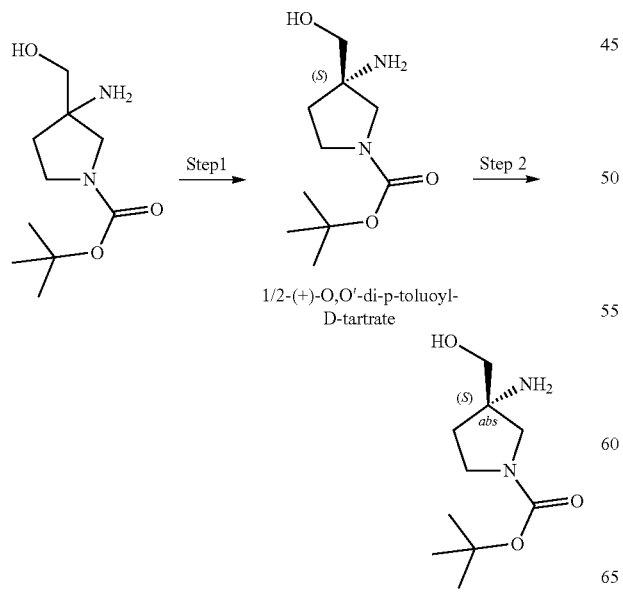

D6 was prepared as described for D5 starting from tert-butyl 3-amino-3-(hydroxymethyl)pyrrolidine-1-carboxylate (Fluorochem, cat no 237078, CAS: 889949-18-2) (500 mg, 2.31 mmol) and (+)-O,O'-di-p-toluoyl-D-tartrate (0.5 eq, 445 mg, 1.15 mmol). $^1$H NMR (300 MHz, CHLOROFORM-d) δ ppm 1.45 (s, 9H) 1.61-1.81 (m, 1H) 1.82-2.15 (m, 3H) 3.51 (m, 6H).

Description D7: ethyl (R)-4-(N-(1-(tert-butoxycarbonyl)-3-(hydroxymethyl)pyrrolidin-3-yl)sulfamoyl)-3-fluoro-1-methyl-1H-pyrrole-2-carboxylate (D7)

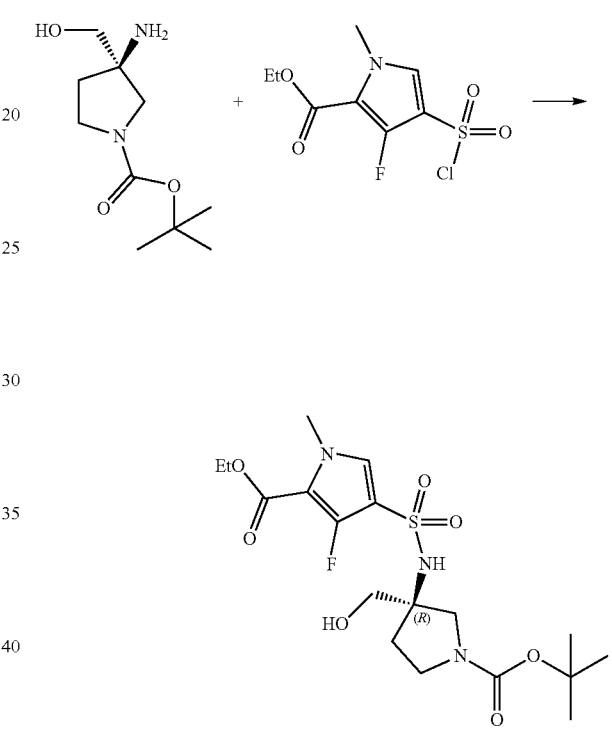

D7 was prepared as described for D1 starting from D5 instead of tert-butyl 3-amino-3-(hydroxymethyl)pyrrolidine-1-carboxylate. Method 1: Rt=1.70 min; m/z=450.3 (M+H)$^+$.

Description D8: ethyl (S)-4-(N-(1-(tert-butoxycarbonyl)-3-(hydroxymethyl)pyrrolidin-3-yl)sulfamoyl)-3-fluoro-1-methyl-1H-pyrrole-2-carboxylate (D8)

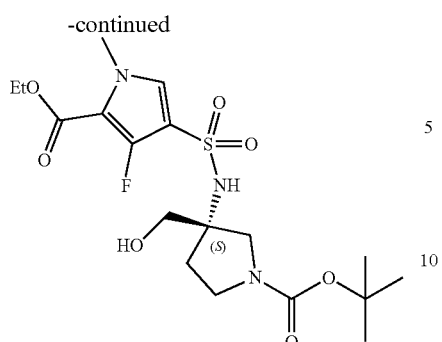

D8 was prepared as described for D1 starting from D6 instead of tert-butyl 3-amino-3-(hydroxymethyl)pyrrolidine-1-carboxylate. Method 1: Rt=1.70 min; m/z=450.3 (M+H)$^+$.

Description D9: tert-butyl 4-((5-(ethoxycarbonyl)-4-fluoro-1-methyl-1H-pyrrole)-3-sulfonamido)-4-(hydroxymethyl)piperidine-1-carboxylate (D9)

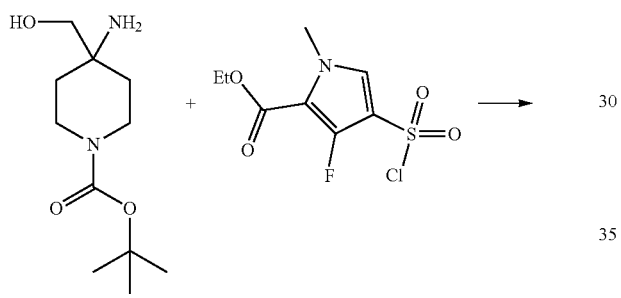

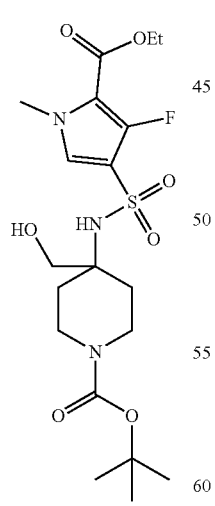

D9 was prepared as described for D1 starting from 1-Boc-4-amino-4-(hydroxymethyl)piperidine (Flurocohem, cat 469124, CAS: 203186-96-3) instead of tert-butyl 3-amino-3-(hydroxymethyl)pyrrolidine-1-carboxylate. Method 1: Rt=1.89 min; m/z=464.4 (M+H)$^+$.

Description D10: ethyl 4-(N-(1-(tert-butoxycarbonyl)-3-(hydroxymethyl)azetidin-3-yl)sulfamoyl)-3-fluoro-1-methyl-1H-pyrrole-2-carboxylate (D10)

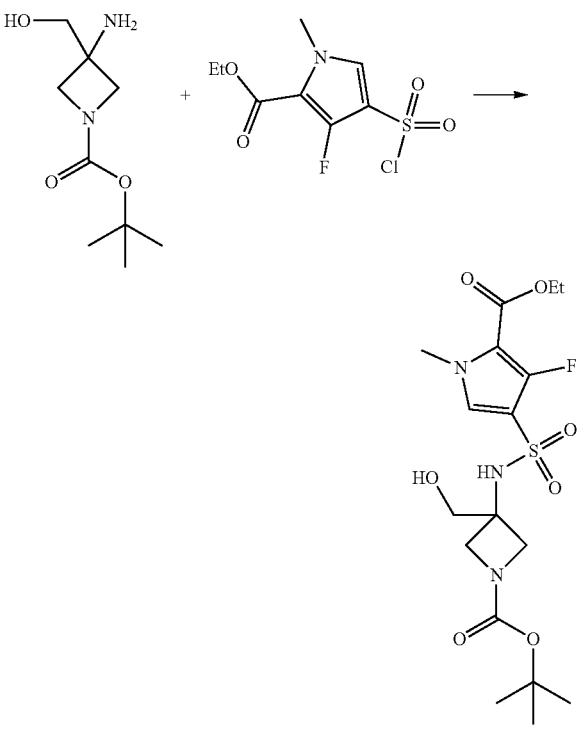

D10 was prepared as described for D1 starting from 1-Boc-3-amino-3-(hydroxymethyl)azetidine (Fluorochem, cat 502710, CAS: 1262411-27-7) instead of tert-butyl 3-amino-3-(hydroxymethyl)pyrrolidine-1-carboxylate. Method 1: Rt=1.83 min; m/z=436.4 (M+H)$^+$.

Description D11: (R)—N-(3-chloro-4-fluorophenyl)-7'-methyl-2'H,4'H,7'H-spiro[pyrrolidine-3,3'-pyrrolo[3,4-b][1,4,5]oxathiazepine]-6'-carboxamide 1',1'-dioxide hydrochloride (D11)

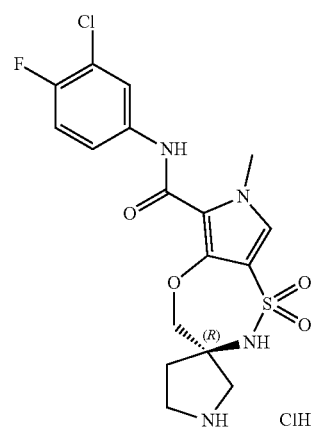

Prepared similarly as described for compound D2 starting from D7 and 3-chloro-4-fluoroaniline (001682, Fluorochem, CAS: 367-21-5) in Step 1 instead of 3,4-difluoroaniline. Method 1: Rt=1.42 min; m/z=429.23 (M+H)+.

Description D12: (S)—N-(3-chloro-4-fluorophenyl)-7'-methyl-2'H,4'H,7'H-spiro[pyrrolidine-3,3'-pyrrolo[3,4-b][1,4,5]oxathiazepine]-6'-carboxamide 1',1'-dioxide hydrochloride (D12)

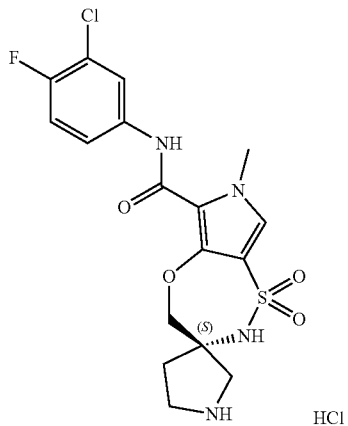

Prepared similarly as described for compound D2 starting from D8 and 3-chloro-4-fluoroaniline (001682, Fluorochem, CAS: 367-21-5) in Step 1 instead of 3,4-difluoroaniline.

Description D13: N-(3-chloro-4-fluorophenyl)-7'-methyl-2'H,4'H,7'H-spiro[piperidine-4,3'-pyrrolo[3,4-b][1,4,5]oxathiazepine]-6'-carboxamide 1',1'-dioxide hydrochloride (D13)

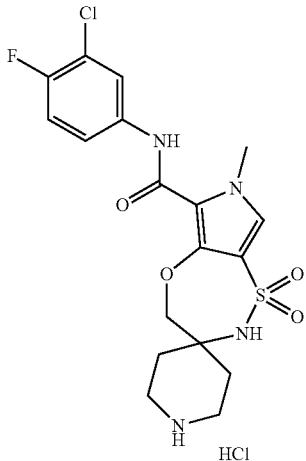 [SMILES: Cn1cc2c(c1C(=O)Nc1ccc(F)c(Cl)c1)OCC1(CCNCC1)NS2(=O)=O ; Cl]

Prepared similarly as described for compound D2 starting from D9 and 3-chloro-4-fluoroaniline (001682, Fluorochem, CAS: 367-21-5) in Step 1 instead of 3,4-difluoroaniline. Method 1: Rt=1.44 min; m/z=443.3 (M+H)+.

Description D14: N-(3-chloro-4-fluorophenyl)-7'-methyl-2'H,4'H,7'H-spiro[azetidine-3,3'-pyrrolo[3,4-b][1,4,5]oxathiazepine]-6'-carboxamide 1',1'-dioxide hydrochloride (D14)

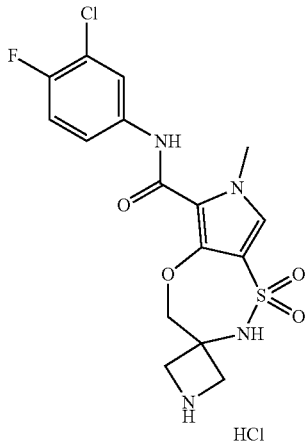 [SMILES: Cn1cc2c(c1C(=O)Nc1ccc(F)c(Cl)c1)OCC1(CNC1)NS2(=O)=O ; Cl]

Prepared similarly as described for compound D2 starting from D10 and 3-chloro-4-fluoroaniline (001682, Fluorochem, CAS: 367-21-5) in Step 1 instead of 3,4-difluoroaniline. Method 1: Rt=1.40 min; m/z=415.3 (M+H)+.

Description D15: (R)—N-(3-(difluoromethyl)-4-fluorophenyl)-7'-methyl-2'H,4'H,7'H-spiro[pyrrolidine-3,3'-pyrrolo[3,4-b][1,4,5]oxathiazepine]-6'-carboxamide 1',1'-dioxide hydrochloride (D15)

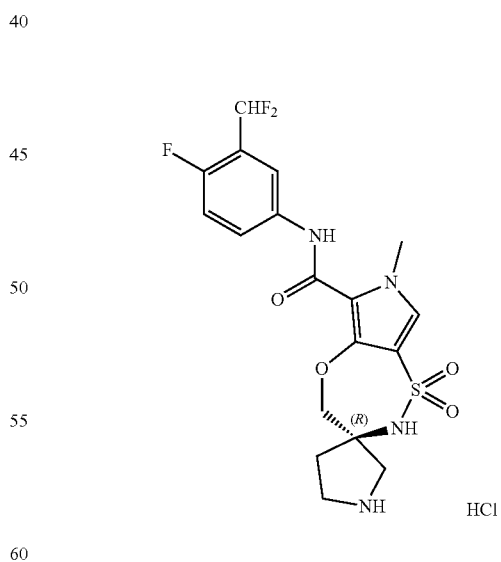

Prepared similarly as described for compound D2 starting from D7 and 3-(difluoromethyl)-4-fluoroaniline (101786, Fluorochem, CAS: 445303-96-8) in Step 1 instead of 3,4-difluoroaniline. Method 1: Rt=1.37 min; m/z=445.16 (M+H)+.

Description D16: (S)—N-(3-(difluoromethyl)-4-fluorophenyl)-7'-methyl-2'H,4'H,7'H-spiro[pyrrolidine-3,3'-pyrrolo[3,4-b][1,4,5]oxathiazepine]-6'-carboxamide 1',1'-dioxide hydrochloride (D16)

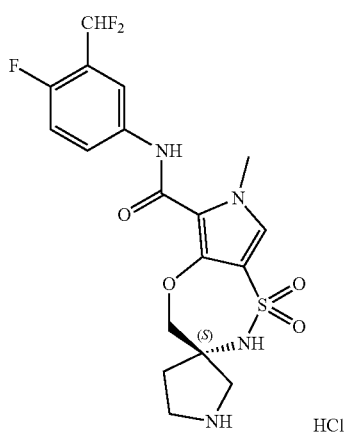

Prepared similarly as described for compound D2 starting from D8 and 3-(Difluoromethyl)-4-fluoroaniline (101786, Fluorochem, CAS: 445303-96-8) in Step 1 instead of 3,4-difluoroaniline. Method 1: Rt=1.37 min; m/z=445.16 (M+H)$^+$.

Description D17: N-(3-(difluoromethyl)-4-fluorophenyl)-7'-methyl-2'H,4'H,7'H-spiro[piperidine-4,3'-pyrrolo[3,4-b][1,4,5]oxathiazepine]-6'-carboxamide 1',1'-dioxide hydrochloride (D17)

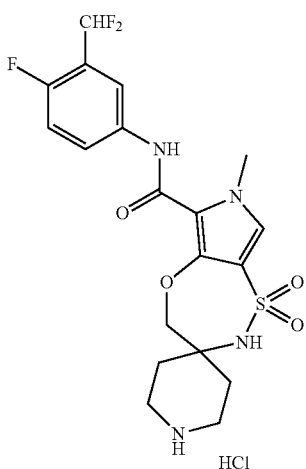 [SMILES: Cn1cc2c(c1C(=O)Nc1ccc(F)c(C(F)F)c1)OCC1(CCNCC1)NS2(=O)=O ; Cl]

Prepared similarly as described for compound D2 starting from D9 and 3-(Difluoromethyl)-4-fluoroaniline (101786, Fluorochem, CAS: 445303-96-8) to afford D17. Method 1: Rt=1.39 min; m/z=459.3 (M+H)$^+$.

Description D18: N-(3-(difluoromethyl)-4-fluorophenyl)-7'-methyl-2'H,4'H,7'H-spiro[azetidine-3,3'-pyrrolo[3,4-b][1,4,5]oxathiazepine]-6'-carboxamide 1',1'-dioxide hydrochloride (D18)

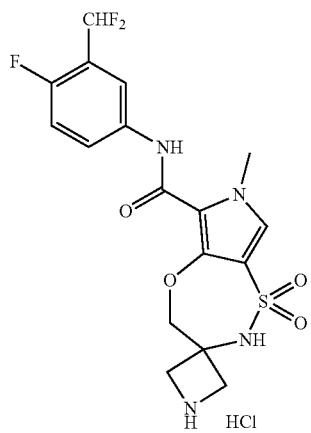 [SMILES: Cn1cc2c(c1C(=O)Nc1ccc(F)c(C(F)F)c1)OCC1(CNC1)NS2(=O)=O ; Cl]

Prepared similarly as described for compound D2 starting from D10 and 3-(difluoromethyl)-4-fluoroaniline (101786, Fluorochem, CAS: 445303-96-8) in Step 1 instead of 3,4-difluoroaniline. Method 1: Rt=1.35 min; m/z=431.25 (M+H)$^+$.

Description D19: ethyl (S)-2-oxo-2-((1,1,1-trifluoropropan-2-yl)amino)acetate (D19)

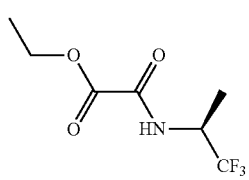

Prepared similarly as described for compound D3, starting from ethyl 2-chloro-2-oxoacetate and using (2S)-1,1,1-trifluoro-2-propanamine hydrochloride instead of (2R)-1,1,1-trifluoro-2-propanamine hydrochloride to afford D19 as colourless oil. Method 2; Rt=2.84 min. m/z=214.34 (M+H)$^+$.

Description D20: sodium (S)-2-oxo-2-((1,1,1-trifluoropropan-2-yl)amino)acetate (D20)

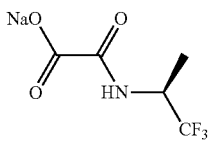

Prepared similarly as described for compound D4 starting from D19. Method 6; Rt=1.34 min. m/z=186.3 (M+H)$^+$.

Description D21: ethyl 2-oxo-2-((2,2,2-trifluoroethyl)amino)acetate (D21)

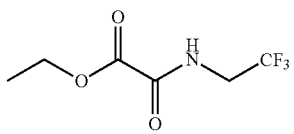

Prepared similarly as described for compound D3, starting from ethyl 2-chloro-2-oxoacetate and using 2,2,2-trifluoroethylamine hydrochloride instead of (2R)-1,1,1-trifluoro-2-propanamine hydrochloride to afford D21 as a white solid, that was used in the next synthetic step as such. $^1$H NMR (300 MHz, DMSO-d6) δ ppm 1.29 (t, J=7.11 Hz, 3H) 3.83-4.08 (m, 2H) 4.27 (q, J=7.12 Hz, 2H) 9.35-9.70 (m, 1H). Method 6; Rt=2.32 min. m/z=200.2 (M+H)$^+$.

Description D22: sodium 2-oxo-2-((2,2,2-trifluoroethyl)amino)acetate (D22)

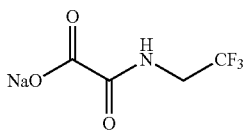

Prepared similarly as described for compound D4 starting from D21. Method 6; Rt=1.22 min. m/z=172.1 (M+H)$^+$.

Description D23: ethyl 2-oxo-2-((1,1,1-trifluoro-2-methylpropan-2-yl)amino)acetate (D23)

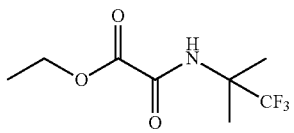

Prepared similarly as described for compound D3, starting from ethyl 2-chloro-2-oxoacetate and using 2,2,2-trifluoro-1,1-dimethyl-ethylamine hydrochloride instead of (2R)-1,1,1-trifluoro-2-propanamine hydrochloride to afford D23 as colourless oil, that was used in the next synthetic step as such. Method 6; Rt=3.54 min. m/z=228.13 (M+H)$^+$.

Description D24: sodium 2-oxo-2-((1,1,1-trifluoro-2-methylpropan-2-yl)amino)acetate (D24)

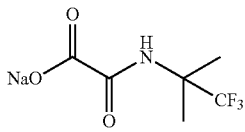

Prepared similarly as described for compound D4 starting from D23. Method 6; Rt=1.07 min. m/z=200.15 (M+H)$^+$.

Description D25: ethyl 2-(3,3-difluoroazetidin-1-yl)-2-oxoacetate (D25)

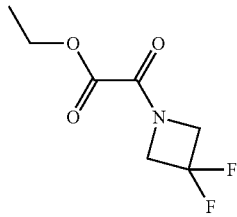

Prepared similarly as described for compound D3, starting from ethyl 2-chloro-2-oxoacetate and using 3,3-difluoroazetidine hydrochloride instead of (2R)-1,1,1-trifluoro-2-propanamine hydrochloride to afford D25 as a light orange solid, that was used in the next synthetic step as such. Method 2; Rt=2.40. m/z=194.12 (M+H)$^+$.

Description D26: Sodium 2-(3,3-difluoroazetidin-1-yl)-2-oxoacetate (D26)

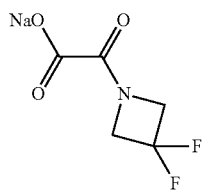

Prepared similarly as described for compound D4 starting from D25. Method 6; Rt=0.92 min. m/z=166 (M+H)$^+$.

Description D27: methyl 2-(cyclopropylamino)-2-oxoacetate (D27)

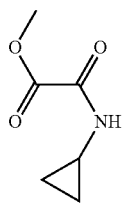

Prepared similarly as described for compound D3, using 3,3-difluoroazetidine hydrochloride instead of (2R)-1,1,1-trifluoro-2-propanamine hydrochloride to afford D27 (1.869 g, yield=73%). $^1$H NMR (300 MHz, DMSO-d6) δ 0.56-0.69 (m, 3H), 2.74 (br d, J=3.94 Hz, 1H), 3.76 (s, 3H), 8.95 (br s, 1H). Method 1: Rt=0.66 min, m/z=143.96 (M+H)$^+$.

Description D28: Sodium 2-(cyclopropylamino)-2-oxoacetate (D28)

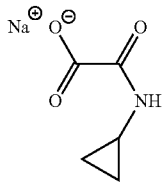

Prepared similarly as described for compound D4 starting from D27 to afford D28 (984 mg, 6.51 mmol) as a white powder. Method 13: Rt=0.78 min; m/z=130.11 (M+H)⁺.

Example E1: N-(3,4-difluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide (E1)

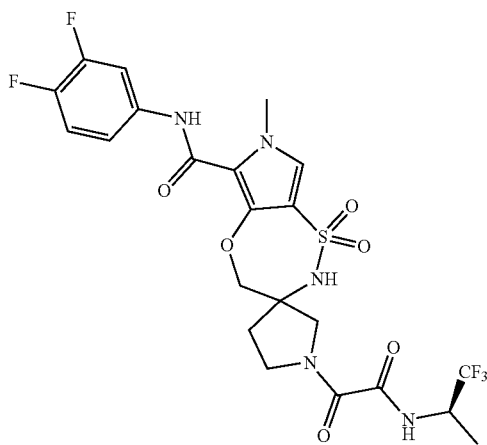 [SMILES: C[C@@H](NC(=O)C(=O)N1CCC2(COc3c(cn(C)c3C(=O)Nc3ccc(F)c(F)c3)S(=O)(=O)N2)C1)C(F)(F)F]

To a solution of D2 (30 mg, 0.070 mmol), benzotriazol-1-yloxytris(dimethylamino)phosphonium hexafluorophosphate (29.56 mg, 0.070 mmol) and sodium (R)-2-oxo-2-((1,1,1-trifluoropropan-2-yl)amino)acetate D4 (13.84 mg, 0.070 mmol) in DMF (1 mL, 0.013 mol), DIPEA (47 uL, 0.270 mmol) was added dropwise at room temperature. The reaction mixture was stirred at the same conditions for 30 min; then was diluted with EtOAc and was washed with 1N NaOH (aq). The organic layer was separated, dried over Na₂SO₄, filtered and concentrated under reduced pressure. The crude was purified by Fraction-Lynx (H₂O/CH₃CN+ 1‰ TFA) to afford E1 in approximately 40% yield. NMR: $^1$H NMR (300 MHz, DMSO-d₆+TFA) δ ppm 1.22-1.39 (m, 3H) 1.92-2.40 (m, 2H) 3.44-4.18 (m, 7H) 4.40-4.72 (m, 3H) 7.30-7.57 (m, 3H) 7.75-7.92 (m, 1H) 8.29 (m, 1H) 9.21-9.37 (m, 1H) 9.44 (br dd, J=8.16, 2.84 Hz, 1H). Method 3: Rt=3.54 min; m/z=580.32 (M+H)⁺.

Example E2: N-(3,4-difluorophenyl)-7'-methyl-1-(5-methyl-1,3,4-oxadiazole-2-carbonyl)-2'H,4'H,7'H-spiro[pyrrolidine-3,3'-pyrrolo[3,4-b][1,4,5]oxathiazepine]-6'-carboxamide 1',1'-dioxide (E2)

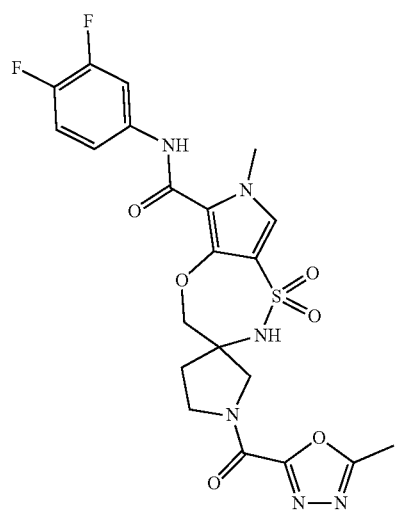 [SMILES: Cc1nnc(C(=O)N2CCC3(COc4c(cn(C)c4C(=O)Nc4ccc(F)c(F)c4)S(=O)(=O)N3)C2)o1]

D2 (8.96 mg, 0.02 mmol) was suspended in MeCN (1 mL) and treated with a single portion of TEA (8 μL, 0.06 mmol), giving a white suspension. To this mixture, 5-methyl-1,3,4-oxadiazole-2-carbonyl chloride (1.17 M in MeCN, 30 uL) (Org.Proc.Res.Develop. 2011, 15, 73-83) was added in a single portion at 0° C. The reaction was stirred at room temperature for 15 min. The reaction was quenched by MeOH, the solvent was removed, then was dissolved in DCM and washed with brine and aq 5% citric acid. The organic layer was concentrated under reduced pressure; the residue dissolved in MeOH (15 mL) and was slowly concentrated. This procedure was repeated for 5 times to give a crude product, this was purified by preparative HPLC (H₂O, CH₃CN 0.1% HCOOH) to yield E2 in approximately 40% yield. $^1$H NMR (300 MHz, DMSO-d₆) δ ppm 2.04-2.45 (m, 2H) 2.60 (s, 3H) 3.82 (d, J=4.68 Hz, 5H) 3.98-4.40 (m, 2H) 4.45-4.70 (m, 2H) 7.28-7.57 (m, 3H) 7.73-7.93 (m, 1H) 8.20-8.63 (m, 1H) 9.37-9.62 (m, 1H). Method 3: Rt=3.08 min; m/z=523.25 (M+H)⁺.

Example E3: 8'-chloro-N-(3,4-difluorophenyl)-7'-methyl-1-(2-oxo-2-(((R)-1,1,1-trifluoropropan-2-yl)amino)acetyl)-2'H,4'H,7'H-spiro[pyrrolo-3,3'-pyrrolo[3,4-b][1,4,5]oxathiazepine]-6'-carboxamide 1',1'-dioxide (E3)

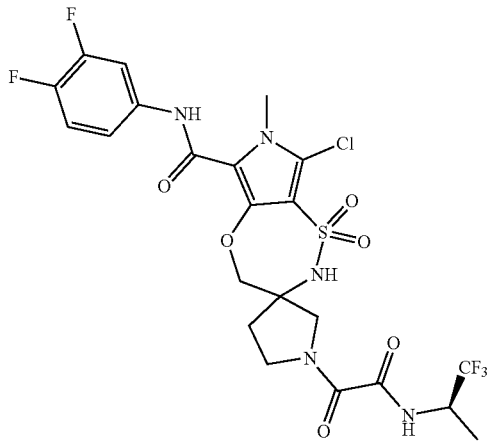 [SMILES: C[C@@H](NC(=O)C(=O)N1CCC2(COc3c(c(Cl)n(C)c3C(=O)Nc3ccc(F)c(F)c3)S(=O)(=O)N2)C1)C(F)(F)F]

To a stirred solution of E1 (13.45 mg, 0.020 mmol) in DCM (1 mL) was added sulfuryl dichloride (2 uL; 0.020 mmol) (used 200 uL from previously prepared stock solution of 20 uL SO$_2$Cl$_2$ in 2 mL of DCM) at 0° C. The reaction was stirred at 0° C. for 30 min and a second eq of SO$_2$Cl$_2$ was added. The reaction was stirred for 1 hr; then was stopped by addition of NaHCO$_3$ ss, diluted with DCM; the organic phase was separated by Phase separator and was concentrated under reduced pressure. The crude was purified by preparative HPLC (H$_2$O, CH$_3$CN 0.1% TFA) to yield E3 in approximately 20% yield. $^1$H NMR (300 MHz, DMSO-d6+TFA) δ ppm 1.25-1.40 (m, 3H) 1.89-2.38 (m, 2H) 3.38-4.18 (m, 7H) 4.37-4.80 (m, 3H) 7.25-7.55 (m, 2H) 7.66-7.95 (m, 1H) 8.48-8.67 (m, 1H) 9.14-9.40 (m, 1H) 9.64 (t, J=3.94 Hz, 1H). Method 3: Rt=3.74 min; m/z=614.22 (M+H)$^+$.

Example E4: (R)—N-(3-chloro-4-fluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide (E4)

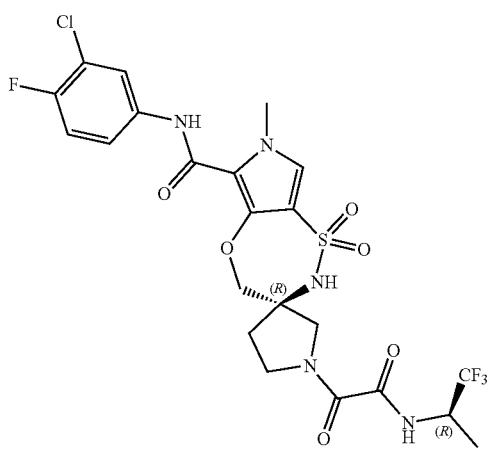

To a stirred solution of D11 (35 mg, 0.08 mmol) and D3 (24.05 mg, 0.11 mmol) in ethanol (1.1572 mL, 0.020 mol), DBU (22.9 mg, 0.150 mmol) was added in a single portion. The reaction mixture was stirred at room temperature overnight. The reaction was diluted with MeCN and purified by preparative HPLC (H$_2$O, CH$_3$CN 0.1% TFA) to yield E4 (31.3 mg, 0.052 mmol, y=70%) as white solid. $^1$H NMR (300 MHz, DMSO-d$_6$) δ ppm 1.31 (t, J=6.88 Hz, 3H) 1.96-2.38 (m, 2H) 3.48-3.67 (m, 2H) 3.75-4.12 (m, 5H) 4.39-4.74 (m, 3H) 7.41 (t, J=9.08 Hz, 1H) 7.51 (d, J=2.93 Hz, 1H) 7.61-7.69 (m, 1H) 7.96 (dt, J=6.79, 2.57 Hz, 1H) 8.30 (d, J=10.18 Hz, 1H) 9.30 (dd, J=13.94, 9.08 Hz, 1H) 9.42 (d, J=4.68 Hz, 1H). Method 3: Rt=3.69 min; m/z=596.2 (M+H)$^+$.

Example E5: (S)—N-(3-chloro-4-fluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide (E5)

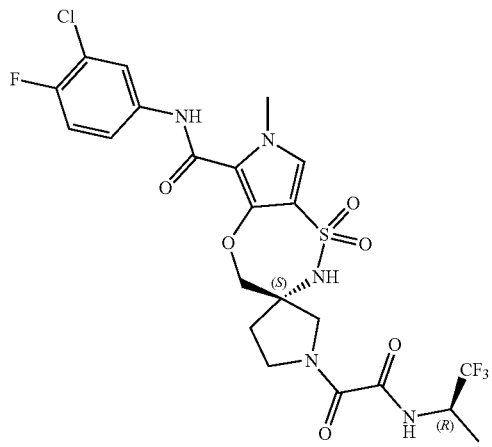

Prepared similarly as described for compound E4 starting from D12 instead of D11 to afford E5 (23.54 mg, 0.039 mmol, y=61%). $^1$H NMR (300 MHz, DMSO-d$_6$+TFA) δ ppm 1.30 (dd, J=7.01, 2.15 Hz, 3H) 1.99-2.39 (m, 2H) 3.83 (s, 7H) 4.44-4.72 (m, 3H) 7.39 (t, J=9.12 Hz, 1H) 7.46-7.55 (m, 1H) 7.58-7.72 (m, 1H) 7.96 (dd, J=6.79, 2.48 Hz, 1H) 8.28 (d, J=6.05 Hz, 1H) 9.30 (t, J=9.26 Hz, 1H) 9.41 (d, J=11.65 Hz, 1H). Method 3: Rt=3.69 min; m/z=596.1 (M+H)$^+$.

Example E6: (R)—N-(3-(difluoromethyl)-4-fluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide (E6)

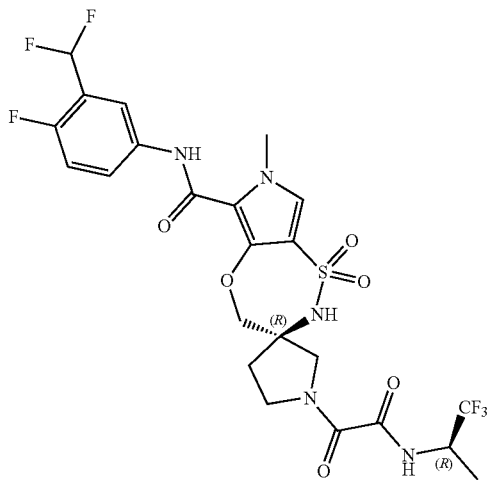

Prepared similarly as described for compound E4 starting from D15 instead of D11 to afford E6 (20.62 mg, 0.034 mmol, y=65%). $^1$H NMR (300 MHz, DMSO-d$_6$) δ ppm 1.31 (t, J=6.79 Hz, 3H) 2.04-2.37 (m, 2H) 3.20-4.16 (m, 7H) 4.42-4.74 (m, 3H) 7.02-7.45 (m, 2H) 7.51 (d, J=3.03 Hz, 1H) 7.81 (br dd, J=8.25, 3.85 Hz, 1H) 8.02 (br d, J=5.14 Hz, 1H) 8.30 (d, J=9.81 Hz, 1H) 9.30 (dd, J=14.21, 9.08 Hz, 1H) 9.49 (d, J=4.31 Hz, 1H). Method 3: Rt=3.54 min; m/z=612.28 (M+H)$^+$.

Example E7: (R)—N-(3-chloro-4-fluorophenyl)-7'-methyl-1-(2-oxo-2-((1,1,1-trifluoropropan-2-yl)amino)acetyl)-2'H,4'H,7'H-spiro[piperidine-4,3'-pyrrolo[3,4-b][1,4,5]oxathiazepine]-6'-carboxamide 1',1'-dioxide (E7)

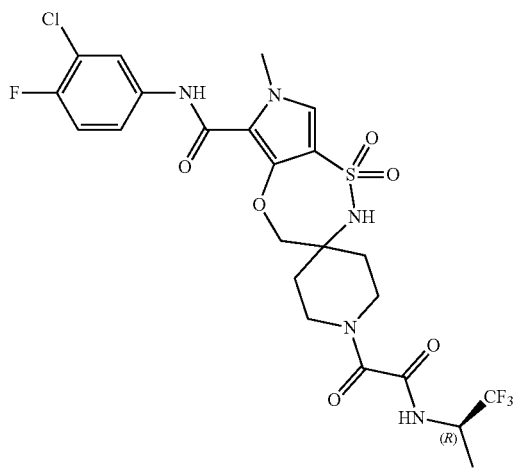

Prepared similarly as described for compound E4 starting from D13 instead of D11 to afford E7 (19.45 mg, 0.032 mmol, y=61%). $^1$H NMR (300 MHz, DMSO-d$_6$) δ ppm 1.21-1.38 (m, 3H) 1.44-1.72 (m, 2H) 2.00-2.20 (m, 2H) 2.99-3.20 (m, 1H) 3.27-4.19 (m, 6H) 4.36-4.48 (m, 2H) 4.57-4.75 (m, 1H) 7.41 (t, J=9.08 Hz, 1H) 7.51 (s, 1H) 7.59-7.68 (m, 1H) 7.88-7.92 (m, 1H) 7.96 (dd, J=6.79, 2.57 Hz, 1H) 9.33 (dd, J=8.80, 4.77 Hz, 1H) 9.40 (s, 1H). Method 3: Rt=3.61 min; m/z=610.25 (M+H)$^+$.

Example E8: (R)—N-(3-(difluoromethyl)-4-fluorophenyl)-7'-methyl-1-(2-oxo-2-((1,1,1-trifluoropropan-2-yl)amino)acetyl)-2'H,4'H,7'H-spiro[piperidine-4,3'-pyrrolo[3,4-b][1,4,5]oxathiazepine]-6'-carboxamide 1',1'-dioxide (E8)

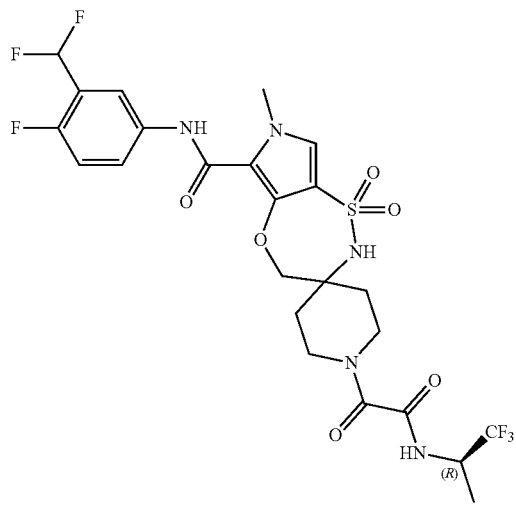

Prepared similarly as described for compound E4 starting from D17 instead of D11 to afford E8 (17.64 mg, 0.028 mmol, y=58%). $^1$H NMR (300 MHz, DMSO-d$_6$) δ ppm 1.29 (dd, J=6.97, 3.48 Hz, 3H) 1.45-1.71 (m, 2H) 2.10 (br d, J=13.11 Hz, 2H) 3.10 (br s, 1H) 3.47-3.56 (m, 2H) 3.83 (s, 3H) 4.02-4.16 (m, 1H) 4.35-4.49 (m, 2H) 4.55-4.77 (m, 1H) 6.98-7.44 (m, 2H) 7.51 (s, 1H) 7.81 (br dd, J=8.57, 3.53 Hz, 1H) 7.90 (s, 1H) 8.01 (dd, J=6.24, 2.38 Hz, 1H) 9.33 (dd, J=8.80, 4.58 Hz, 1H) 9.45 (s, 1H). Method 3: Rt=3.46 min; m/z=626.3 (M+H)$^+$.

Example E9: (R)—N-(3-chloro-4-fluorophenyl)-7'-methyl-1-(2-oxo-2-((1,1,1-trifluoropropan-2-yl)amino)acetyl)-2'H,4'H,7'H-spiro[azetidine-3,3'-pyrrolo[3,4-b][1,4,5]oxathiazepine]-6'-carboxamide 1',1'-dioxide (E9)

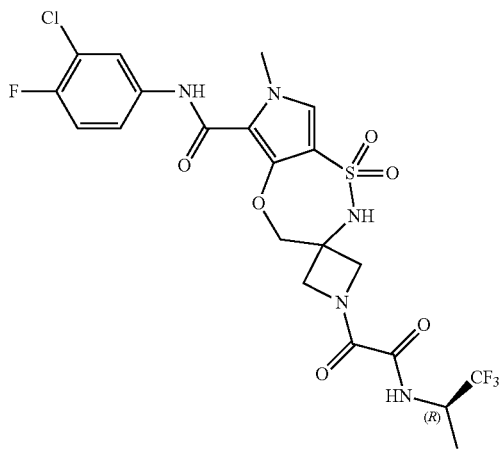

Prepared similarly as described for compound E4 starting from D14 instead of D11 to afford E9 (11.49 mg, 0.02 mmol, y=41%). $^1$H NMR (300 MHz, DMSO-d$_6$) δ ppm 1.33 (dd, J=7.01, 1.97 Hz, 3H) 3.75-3.91 (m, 3H) 4.01-4.20 (m, 2H) 4.45-4.77 (m, 5H) 7.41 (t, J=9.12 Hz, 1H) 7.53 (s, 1H) 7.63-7.76 (m, 1H) 7.91-8.05 (m, 1H) 8.63 (d, J=5.41 Hz, 1H) 9.30 (t, J=9.17 Hz, 1H) 9.44 (d, J=4.22 Hz, 1H). Method 3: Rt=3.71 min; m/z=582.23 (M+H)$^+$.

Example E10: (R)—N-(3-(difluoromethyl)-4-fluorophenyl)-7'-methyl-1-(2-oxo-2-((1,1,1-trifluoropropan-2-yl)amino)acetyl)-2'H,4'H,7'H-spiro[azetidine-3,3'-pyrrolo[3,4-b][1,4,5]oxathiazepine]-6'-carboxamide 1',1'-dioxide (E10)

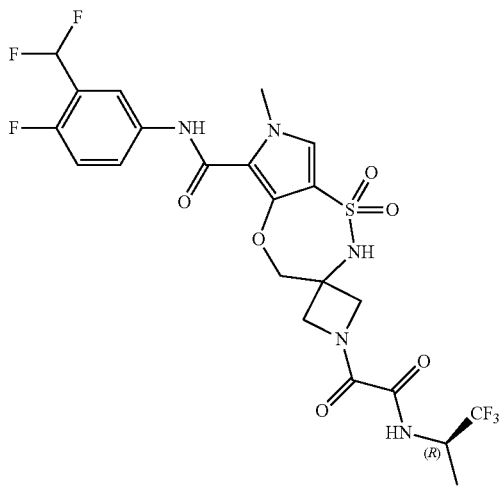

Prepared similarly as described for compound E4 starting from D18 instead of D11 to afford E10 (17.04 mg, 0.028 mmol, y=61%). $^1$H NMR (300 MHz, DMSO-d$_6$) δ ppm 1.32 (dd, J=7.01, 2.25 Hz, 3H) 3.84 (s, 3H) 4.07-4.16 (m, 2H) 4.46-4.77 (m, 5H) 6.97-7.46 (m, 2H) 7.53 (s, 1H) 7.79-7.90 (m, 1H) 8.04 (br d, J=6.14 Hz, 1H) 8.62 (d, J=5.41 Hz, 1H) 9.30 (t, J=8.89 Hz, 1H) 9.51 (d, J=4.13 Hz, 1H). Method 3: Rt=3.56 min; m/z=598.16 (M+H)$^+$.

Example E11: (S)—N-(3-(difluoromethyl)-4-fluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide (E11)

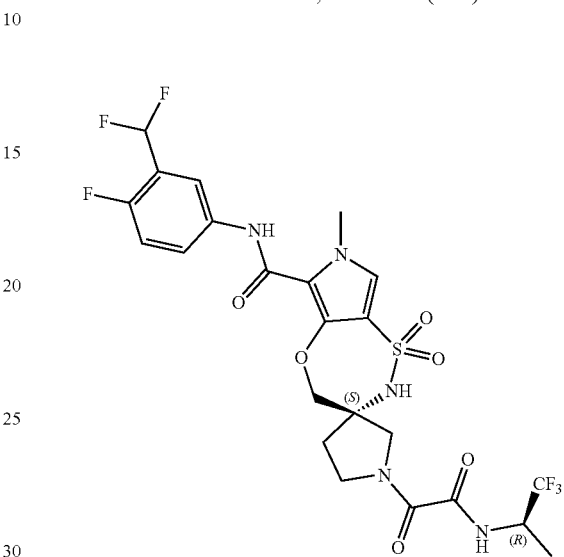

Prepared similarly as described for compound E4 starting from D16 instead of D11 to afford E11 (22.24 mg, 0.036 mmol, y=50%). $^1$H NMR (300 MHz, DMSO-d$_6$+T$_F$A) δ ppm 1.24-1.38 (m, 3H) 2.02-2.39 (m, 2H) 3.53-4.10 (m, 7H) 4.40-4.77 (m, 3H) 6.94-7.42 (m, 2H) 7.49 (d, J=2.48 Hz, 1H) 7.71-7.87 (m, 1H) 7.98-8.07 (m, 1H) 8.27 (d, J=6.97 Hz, 1H) 9.30 (t, J=9.17 Hz, 1H) 9.48 (d, J=11.28 Hz, 1H). Method 3: Rt=3.54 min; m/z=612.34 (M+H)$^+$.

Example E12: (S)—N-(3-chloro-4-fluorophenyl)-7'-methyl-1-(2-oxo-2-((1,1,1-trifluoropropan-2-yl)amino)acetyl)-2'H,4'H,7'H-spiro[piperidine-4,3'-pyrrolo[3,4-b][1,4,5]oxathiazepine]-6'-carboxamide 1',1'-dioxide (E12)

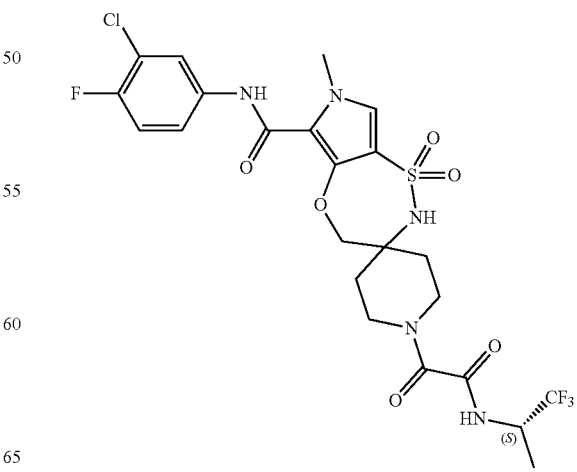

A solution of D13 (10 mg, 0.020 mmol) and D20 (6.48 mg, 0.030 mmol) in DMF (0.5 mL) was treated with N,N-Diisopropylethylamine (0.01 mL, 0.060 mmol) at room temperature; then benzotriazol-1-yloxy)tris(dimethylamino) phosphonium hexafluorophosphate (9.28 mg, 0.02 mmol) was added in a single portion. The reaction was stirred overnight at room temperature then directly purified by preparative HPLC (H$_2$O, CH$_3$CN 0.1% TFA) to yield E12 (4.44 mg, 0.007 mmol, y=35%) as white solid. $^1$H NMR (300 MHz, DMSO-d$_6$) δ ppm 1.29 (dd, J=6.97, 3.21 Hz, 3H) 1.43-1.72 (m, 2H) 2.02-2.19 (m, 2H) 2.99-3.20 (m, 1H) 3.47-3.59 (m, 2H) 3.73-3.91 (m, 3H) 4.09 (br dd, J=12.98, 3.26 Hz, 1H) 4.43 (br d, J=2.29 Hz, 2H) 4.56-4.77 (m, 1H) 7.41 (t, J=9.08 Hz, 1H) 7.51 (s, 1H) 7.64 (ddd, J=9.03, 4.26, 2.66 Hz, 1H) 7.90 (s, 1H) 7.96 (dd, J=6.88, 2.57 Hz, 1H) 9.33 (dd, J=8.80, 4.86 Hz, 1H) 9.39 (s, 1H). Method 3: Rt=3.61 min; m/z=610.25 (M+H)$^+$.

Example E13: N-(3-chloro-4-fluorophenyl)-7'-methyl-1-(2-oxo-2-((2,2,2-trifluoroethyl)amino)acetyl)-2'H,4'H,7'H-spiro[piperidine-4,3'-pyrrolo[3,4-b][1,4,5]oxathiazepine]-6'-carboxamide 1',1'-dioxide (E13)

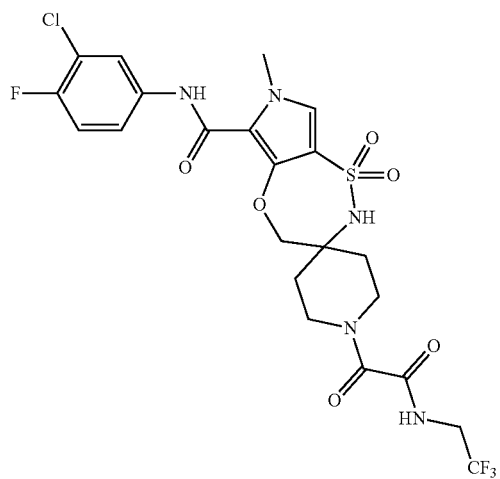 [SMILES: Cn1cc2c(c1C(=O)Nc1ccc(F)c(Cl)c1)OCC1(CCN(C(=O)C(=O)NCC(F)(F)F)CC1)NS2(=O)=O]

Prepared similarly as described for compound E12 starting from D13 and using D22 instead of D20 to afford E13 (4.08 mg, 0.007 mmol, y=32%). $^1$H NMR (300 MHz, DMSO-d$_6$) δ ppm 1.44-1.73 (m, 2H) 2.09 (br d, J=13.57 Hz, 2H) 3.11 (br s, 1H) 3.33-3.44 (m, 1H) 3.53-3.55 (m, 1H) 3.83 (s, 3H) 3.92-4.18 (m, 3H) 4.43 (s, 2H) 7.41 (t, J=9.08 Hz, 1H) 7.51 (s, 1H) 7.64 (ddd, J=9.08, 4.26, 2.61 Hz, 1H) 7.88-7.92 (m, 1H) 7.96 (dd, J=6.79, 2.57 Hz, 1H) 9.31-9.48 (m, 2H). Method 3: Rt=3.52 min; m/z=596.14 (M+H)$^+$.

Example E14: (S)—N-(3-(difluoromethyl)-4-fluorophenyl)-7'-methyl-1-(2-oxo-2-((1,1,1-trifluoropropan-2-yl)amino)acetyl)-2'H,4'H,7'H-spiro[piperidine-4,3'-pyrrolo[3,4-b][1,4,5]oxathiazepine]-6'-carboxamide 1',1'-dioxide (E14)

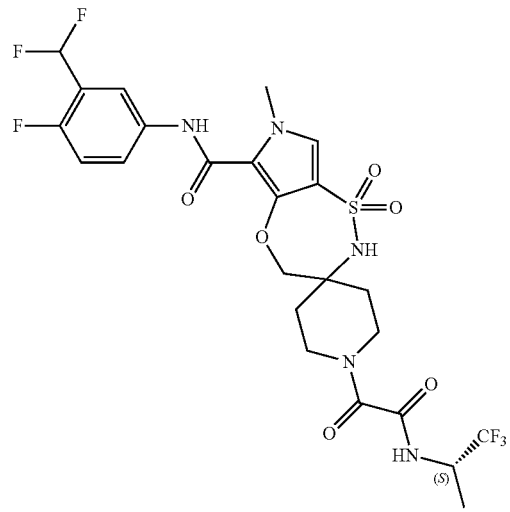

Prepared similarly as described for compound E12 starting from D17 and D20 to afford E14 (6.25 mg, 0.01 mmol, y=43%). $^1$H NMR (300 MHz, DMSO-d6+TFA) δ ppm 1.28 (br s, 3H) 1.45-1.69 (m, 2H) 2.10 (br d, J=7.34 Hz, 2H) 3.01-3.22 (m, 1H) 3.30-3.64 (m, 2H) 3.83 (br d, J=9.26 Hz, 3H) 4.02-4.22 (m, 1H) 4.42 (br d, J=6.97 Hz, 2H) 4.52-4.78 (m, 1H) 6.91-7.56 (m, 3H) 7.66-8.17 (m, 3H) 9.23-9.37 (m, 1H) 9.37-9.49 (m, 1H). Method 3: Rt=3.46 min; m/z=626.32 (M+H)$^+$.

Example E15: N-(3-(difluoromethyl)-4-fluorophenyl)-7'-methyl-1-(2-oxo-2-((1,1,1-trifluoro-2-methylpropan-2-yl)amino)acetyl)-2'H,4'H,7'H-spiro[piperidine-4,3'-pyrrolo[3,4-b][1,4,5]oxathiazepine]-6'-carboxamide 1',1'-dioxide (E15)

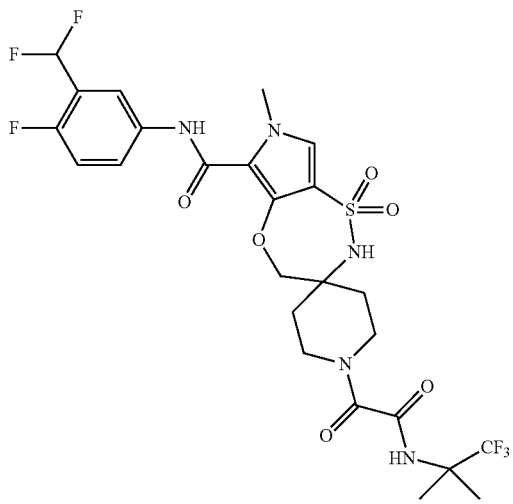 [SMILES: Cn1cc2c(c1C(=O)Nc1ccc(F)c(C(F)F)c1)OCC1(CCN(C(=O)C(=O)NC(C)(C)C(F)(F)F)CC1)NS2(=O)=O]

Prepared similarly as described for compound E12 starting from D17 and using D24 instead of D20 to afford E15 (4.67 mg, 0.007 mmol, y=31%). $^1$H NMR (300 MHz, DMSO-d$_6$) δ ppm 1.44-1.70 (m, 8H) 2.10 (brd, J=13.30 Hz, 2H) 2.97-3.16 (m, 1H) 3.43 (brs, 2H) 3.79-3.88 (m, 3 H) 4.06 (br d, J=13.20 Hz, 1H) 4.41 (s, 2H) 7.00-7.45 (m, 2H) 7.47-7.57 (m, 1H) 7.74-7.85 (m, 1H) 7.85-7.93 (m, 1H) 8.01 (dd, J=6.10, 2.15 Hz, 1H) 8.65-8.90 (m, 1H) 9.32-9.56 (m, 1H). Method 3: Rt=3.57 min; m/z=640.36 (M+H)$^+$.

Example E16: (S)—N-(3-chloro-4-fluorophenyl)-7'-methyl-1-(2-oxo-2-((1,1,1-trifluoropropan-2-yl)amino)acetyl)-2'H,4'H,7'H-spiro[azetidine-3,3'-pyrrolo[3,4-b][1,4,5]oxathiazepine]-6'-carboxamide 1',1'-dioxide (E16)

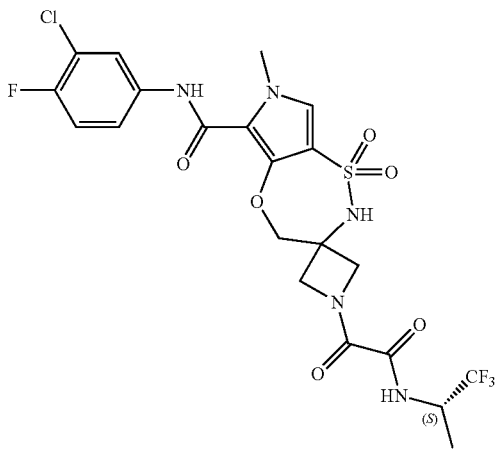

Prepared similarly as described for compound E12 starting from D14 to afford E16 (3.11 mg, 0.005 mmol, y=25%). $^1$H NMR (300 MHz, DMSO-d$_6$) δ ppm 1.33 (dd, J=7.06, 2.02 Hz, 3H) 3.75-3.91 (m, 3H) 4.01-4.20 (m, 2H) 4.46-4.79 (m, 5H) 7.41 (t, J=9.12 Hz, 1H) 7.53 (s, 1H) 7.69 (ddt, J=9.09, 4.44, 2.45, 2.45 Hz, 1H) 7.98 (dt, J=6.79, 2.34 Hz, 1H) 8.63 (d, J=5.41 Hz, 1H) 9.30 (t, J=9.22 Hz, 1H) 9.44 (d, J=4.13 Hz, 1H). Method 3: Rt=3.71 min; m/z=582.23 (M+H)$^+$.

Example E17: N-(3-chloro-4-fluorophenyl)-1-(2-(3,3-difluoroazetidin-1-yl)-2-oxoacetyl)-7'-methyl-2'H,4'H,7'H-spiro[azetidine-3,3'-pyrrolo[3,4-b][1,4,5]oxathiazepine]-6'-carboxamide 1',1'-dioxide (E17)

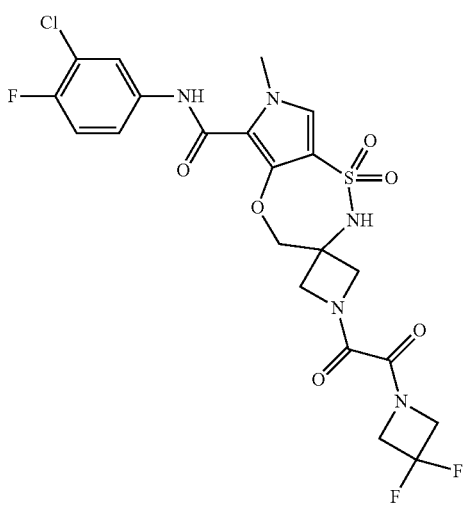 [SMILES: Cn1cc2c(c1C(=O)Nc1ccc(F)c(Cl)c1)OCC1(CN(C(=O)C(=O)N3CC(F)(F)C3)C1)NS2(=O)=O]

Prepared similarly as described for compound E12 starting from D14 and using D26 instead of D20 to afford E17 (1.05 mg, 0.002 mmol, y=9%). $^1$H NMR (300 MHz, DMSO-d$_6$) δ ppm 3.82 (br d, J=7.43 Hz, 3H) 3.94-4.17 (m, 2H) 4.29-4.46 (m, 2H) 4.52 (br d, J=6.88 Hz, 2H) 4.66 (br d, J=6.33 Hz, 2H) 4.80 (br s, 2H) 7.24-7.42 (m, 1H) 7.44-7.56 (m, 1H) 7.59-7.78 (m, 1H) 7.85-8.10 (m, 1H) 8.48-8.71 (m, 1H) 9.33-9.53 (m, 1H). Method 3: Rt=3.52 min; m/z=562.11 (M+H)$^+$.

Example E18: (S)—N-(3-(difluoromethyl)-4-fluorophenyl)-7'-methyl-1-(2-oxo-2-((1,1,1-trifluoropropan-2-yl)amino)acetyl)-2'H,4'H,7'H-spiro[azetidine-3,3'-pyrrolo[3,4-b][1,4,5]oxathiazepine]-6'-carboxamide 1',1'-dioxide (E18)

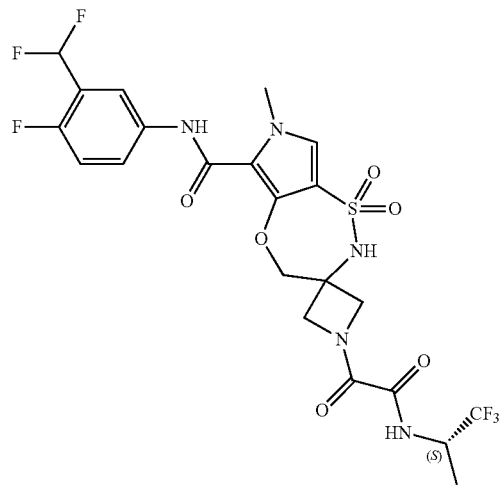

Prepared similarly as described for compound E12 starting from D18 to afford E18 (3.69 mg, 0.006 mmol, y=31%). $^1$H NMR (300 MHz, DMSO-d$_6$) δ ppm 1.28-1.37 (m, 3H) 3.72-3.95 (m, 3H) 3.99-4.23 (m, 2H) 4.39-4.82 (m, 5H) 6.98-7.44 (m, 2H) 7.49-7.57 (m, 1H) 7.77-7.91 (m, 1H) 7.99-8.10 (m, 1H) 8.62 (d, J=5.32 Hz, 1H) 9.24-9.36 (m, 1H) 9.51 (d, J=4.22 Hz, 1H). Method 3: Rt=3.57 min; m/z=598.23 (M+H)$^+$.

Example E19: 1-(2-(cyclopropylamino)-2-oxoacetyl)-N-(3-(difluoromethyl)-4-fluorophenyl)-7'-methyl-2'H,4'H,7'H-spiro[azetidine-3,3'-pyrrolo[3,4-b][1,4,5]oxathiazepine]-6'-carboxamide 1',1'-dioxide (E19)

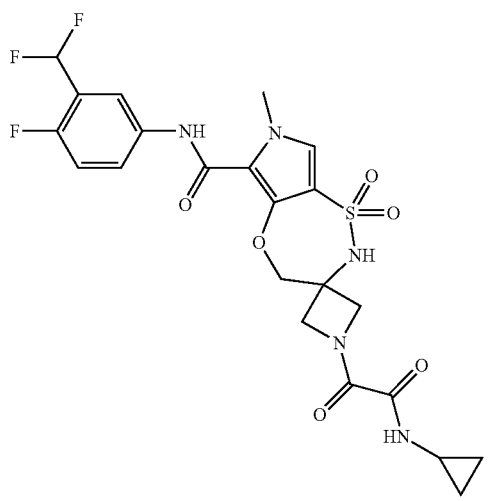 [SMILES: Cn1cc2c(c1C(=O)Nc1ccc(F)c(C(F)F)c1)OCC1(CN(C(=O)C(=O)NC3CC3)C1)NS2(=O)=O]

Prepared similarly as described for compound E12 starting from D18 and using D28 instead of D20 to afford E19 (2.6 mg, 0.005 mmol, y=21%). $^1$H NMR (300 MHz, DMSO-$d_6$) δ ppm 0.51-0.74 (m, 4H) 2.72-2.77 (m, 1H) 3.77-3.91 (m, 3H) 3.95-4.17 (m, 2H) 4.45-4.74 (m, 4H) 6.94-7.46 (m, 2H) 7.48-7.57 (m, 1H) 7.77-7.92 (m, 1H) 7.99-8.12 (m, 1H) 8.55-8.65 (m, 1H) 8.76 (d, J=5.32 Hz, 1H) 9.50 (s, 1H). Method 3: Rt=3.22 min; m/z=542.26 (M+H)$^+$. 0.05 Example E20: (R)—N-(3-chloro-4-fluorophenyl)-7'-methyl-1-(2-oxo-2-((2,2,2-trifluoroethyl)amino)acetyl)-2'H,4'H,7'H-spiro[pyrrolidine-3,3'-pyrrolo[3,4-b][1,4,5]oxathiazepine]-6'-carboxamide 1',1'-dioxide (E20)

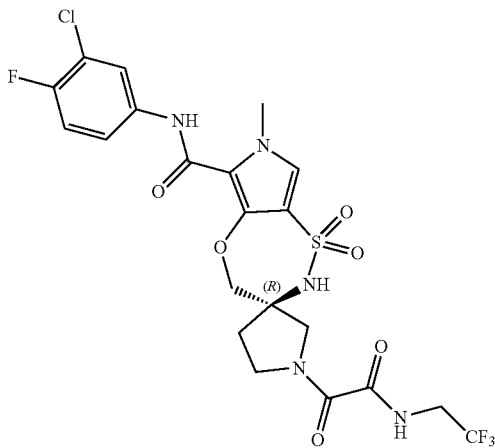

Prepared similarly as described for compound E12 starting from D11 and using D22 instead of D20 to afford E20 (5.87 mg, 0.01 mmol, y=13%). $^1$H NMR (300 MHz, DMSO-$d_6$) δ ppm 1.94-2.41 (m, 2H) 3.47-4.26 (m, 9H) 4.38-4.73 (m, 2H) 7.38 (t, J=9.08 Hz, 1H) 7.50 (d, J=4.13 Hz, 1H) 7.57-7.71 (m, 1H) 7.89-8.04 (m, 1H) 8.29 (s, 1H) 9.26-9.46 (m, 2H). Method 3: Rt=3.59 min; m/z=582.16 (M+H)$^+$.

Example E21: (R)—N-(3-chloro-4-fluorophenyl)-7'-methyl-1-(2-oxo-2-((1,1,1-trifluoro-2-methylpropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide (E21)

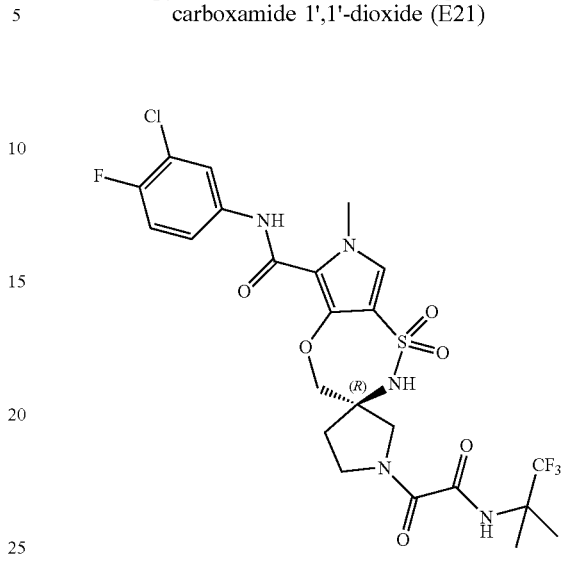

Prepared similarly as described for compound E12 starting from D11 and using D24 instead of D20 to afford E21 (4.95 mg, 0.008 mmol, y=25%). $^1$H NMR (300 MHz, DMSO-$d_6$) δ ppm 1.44-1.62 (m, 6H) 1.99-2.37 (m, 2H) 3.45-4.02 (m, 7H) 4.34-4.72 (m, 2H) 7.38 (t, J=9.08 Hz, 1H) 7.50 (s, 1H) 7.65 (dtd, J=8.85, 4.29, 4.29, 2.75 Hz, 1H) 7.96 (dd, J=6.79, 2.57 Hz, 1H) 8.29 (d, J=2.48 Hz, 1H) 8.55 (d, J=26.00 Hz, 1H) 9.40 (d, J=17.15 Hz, 1H). Method 3: Rt=3.85 min; m/z=610.25 (M+H)$^+$.

Example E22: (R)—N-(3-chloro-4-fluorophenyl)-7'-methyl-1-(2-oxo-2-(((S)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide (E22)

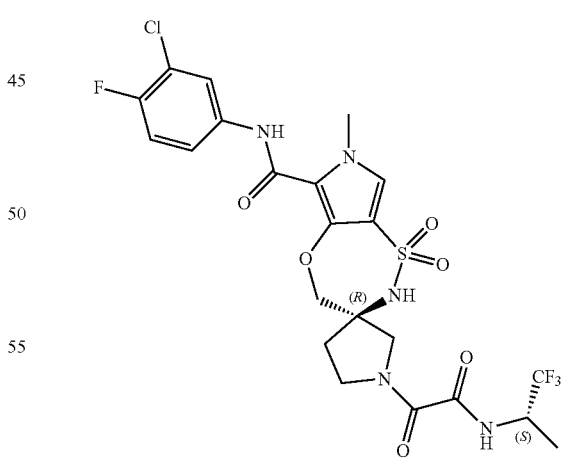

Prepared similarly as described for compound E12 starting from D11 to afford E22 (5.79 mg, 0.01 mmol, y=45%). $^1$H NMR (300 MHz, DMSO-$d_6$) δ ppm 1.31 (dd, J=7.01, 2.52 Hz, 3H) 2.08-2.30 (m, 2H) 3.53-4.13 (m, 7H) 4.44-4.72 (m, 3H) 7.41 (t, J=9.08 Hz, 1H) 7.51 (d, J=2.38 Hz, 1H) 7.61-7.69 (m, 1H) 7.96 (dd, J=6.79, 2.48 Hz, 1H) 8.28 (d, J=6.14 Hz, 1H) 9.32 (t, J=9.35 Hz, 1H) 9.42 (d, J=11.74 Hz, 1H). Method 3: Rt=3.69 min; m/z=596.21 (M+H)$^+$.

Example E23: (R)—N-(3-(difluoromethyl)-4-fluorophenyl)-7'-methyl-1-(2-oxo-2-(((S)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide (E23)

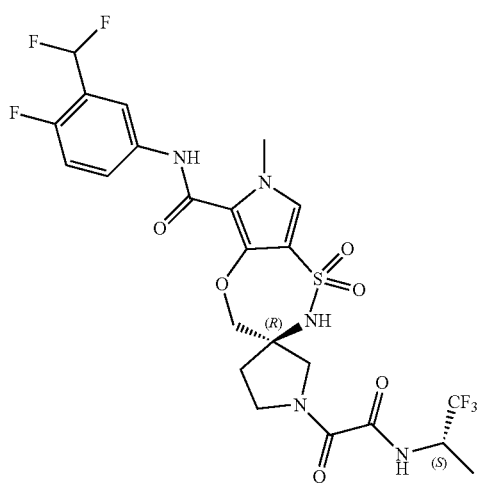

Prepared similarly as described for compound E12 starting from D15 to afford E23 (7.04 mg, 0.011 mmol, y=36%). 1H NMR (300 MHz, DMSO-$d_6$) δ ppm 1.31 (dd, J=7.01, 2.43 Hz, 3H) 2.01-2.38 (m, 2H) 3.45-4.18 (m, 7H) 4.37-4.80 (m, 3H) 7.00-7.45 (m, 2H) 7.51 (d, J=2.66 Hz, 1H) 7.72-7.87 (m, 1H) 7.95-8.09 (m, 1H) 8.27 (d, J=7.15 Hz, 1H) 9.32 (t, J=9.26 Hz, 1H) 9.49 (d, J=11.28 Hz, 1H). Method 3: Rt=3.55 min; m/z=612.21 (M+H)+.

Example E24: (R)—N-(3-(difluoromethyl)-4-fluorophenyl)-7'-methyl-1-(2-oxo-2-((1,1,1-trifluoro-2-methylpropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide (E24)

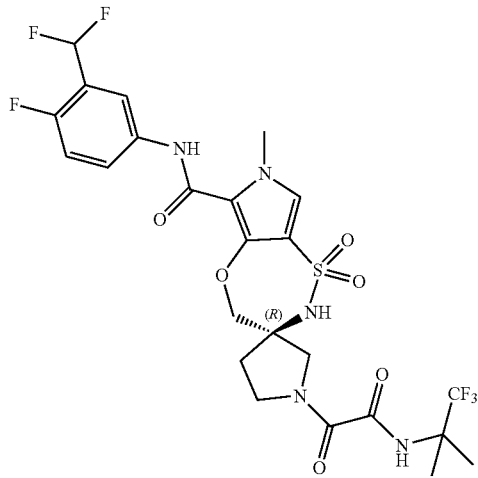

Prepared similarly as described for compound E12 starting from D15 and using D24 instead of D20 to afford E24 (6.4 mg, 0.01 mmol, y=33%). 1H NMR (300 MHz, DMSO-$d_6$) δ ppm 1.44-1.62 (m, 6H) 2.05-2.34 (m, 2H) 3.24-4.12 (m, 7H) 4.36-4.70 (m, 2H) 6.95-7.44 (m, 2H) 7.51 (s, 1H) 7.71-7.87 (m, 1H) 7.95-8.10 (m, 1H) 8.28 (s, 1H) 8.57 (d, J=29.00 Hz, 1H) 9.49 (d, J=16.41 Hz, 1H). Method 3: Rt=3.69 min; m/z=626.32 (M+H)+.

Example E25: (S)—N-(3-chloro-4-fluorophenyl)-7'-methyl-1-(2-oxo-2-((2,2,2-trifluoroethyl)amino)acetyl)-2'H,4'H,7'H-spiro[pyrrolidine-3,3'-pyrrolo[3,4-b][1,4,5]oxathiazepine]-6'-carboxamide 1',1'-dioxide (E25)

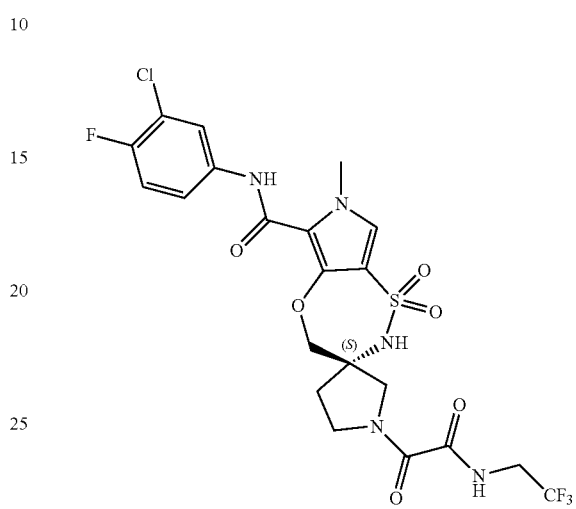

Prepared similarly as described for compound E12 starting from D12 and using D22 instead of D20 to afford E25 (9 mg, 0.015 mmol, y=42%). $^1$H NMR (300 MHz, DMSO-$d_6$+TFA) δ ppm 1.94-2.41 (m, 2H) 3.47-4.26 (m, 9H) 4.38-4.73 (m, 2H) 7.38 (t, J=9.08 Hz, 1H) 7.50 (d, J=4.13 Hz, 1H) 7.57-7.71 (m, 1H) 7.89-8.04 (m, 1H) 8.29 (s, 1H) 9.26-9.46 (m, 2H). Method 3: Rt=3.58 min; m/z=582.30 (M+H)+.

Example E26: (S)—N-(3-chloro-4-fluorophenyl)-7'-methyl-1-(2-oxo-2-((1,1,1-trifluoro-2-methylpropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide (E26)

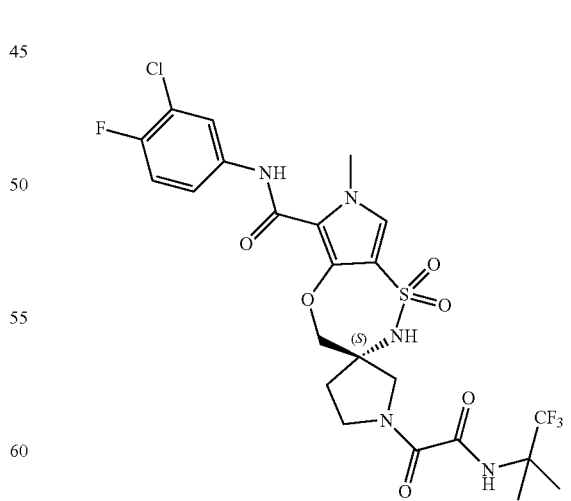

Prepared similarly as described for compound E12 starting from D12 and using D24 instead of D20 to afford E26 (6 mg, 0.01 mmol, y=27%). $^1$H NMR (300 MHz, DMSO-$d_6$+TFA) δ ppm 1.44-1.62 (m, 6H) 1.99-2.37 (m, 2H) 3.45-4.02 (m, 7H) 4.34-4.72 (m, 2H) 7.38 (t, J=9.08 Hz, 1H)

7.50 (s, 1H) 7.65 (dtd, J=8.85, 4.29, 4.29, 2.75 Hz, 1H) 7.96 (dd, J=6.79, 2.57 Hz, 1H) 8.29 (d, J=2.48 Hz, 1H) 8.55 (d, J=26.00 Hz, 1H) 9.40 (d, J=17.15 Hz, 1H). Method 3: Rt=3.84 min; m/z=610.32 (M+H)$^+$.

Example E27: (S)—N-(3-(difluoromethyl)-4-fluorophenyl)-7'-methyl-1-(2-oxo-2-((2,2,2-trifluoroethyl)amino)acetyl)-2'H,4'H,7'H-spiro[pyrrolidine-3,3'-pyrrolo[3,4-b][1,4,5]oxathiazepine]-6'-carboxamide 1',1'-dioxide (E27)

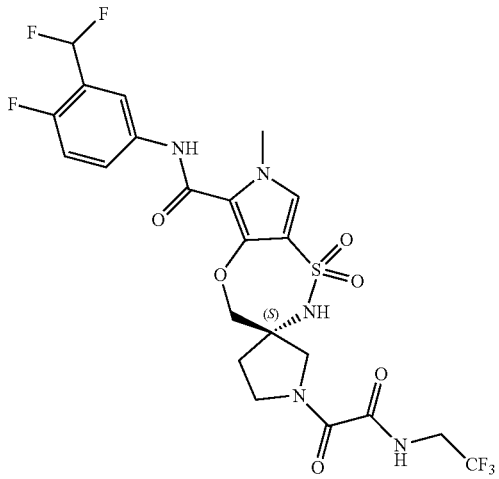

Prepared similarly as described for compound E12 starting from D16 and using D22 instead of D20 to afford E27 (10 mg, 0.017 mmol, y=39%). $^1$H NMR (300 MHz, DMSO-d$_6$) δ ppm 1.99-2.36 (m, 2H) 3.43-4.28 (m, 9H) 4.43-4.72 (m, 2H) 6.97-7.43 (m, 2H) 7.49 (d, J=4.03 Hz, 1H) 7.72-7.86 (m, 1H) 8.02 (br d, J=5.78 Hz, 1H) 8.28 (s, 1H) 9.26-9.41 (m, 1H) 9.48 (s, 1H). Method 3. Rt=3.43 min; m/z=598.30 (M+H)$^+$.

Example E28: (S)—N-(3-(difluoromethyl)-4-fluorophenyl)-7'-methyl-1-(2-oxo-2-((1,1,1-trifluoro-2-methylpropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide (E28)

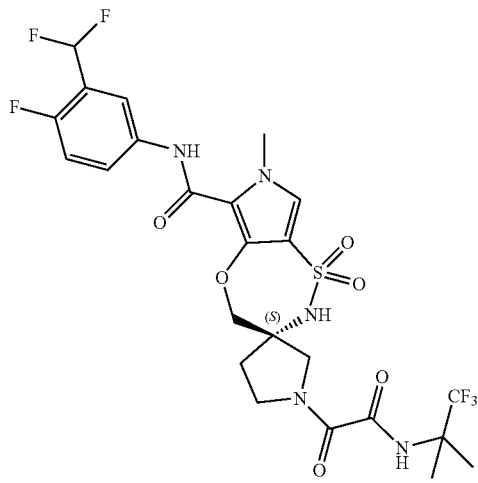

Prepared similarly as described for compound E12 starting from D16 and using D24 instead of D20 to afford E28 (8.36 mg, 0.013 mmol, y=31%). $^1$H NMR (300 MHz, DMSO-d$_6$+TFA) δ ppm 1.46-1.59 (m, 6H) 1.98-2.38 (m, 2H) 3.42-4.11 (m, 7H) 4.35-4.70 (m, 2H) 6.90-7.42 (m, 2H) 7.43-7.56 (m, 1H) 7.70-7.90 (m, 1H) 7.92-8.11 (m, 1H) 8.28 (s, 1H) 8.39-8.69 (m, 1H) 9.47 (d, J=16.05 Hz, 1H). Method 3: Rt=3.69 min; m/z=626.32 (M+H)$^+$.

Example E29: (S)-8'-chloro-N-(3-(difluoromethyl)-4-fluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide (E29)

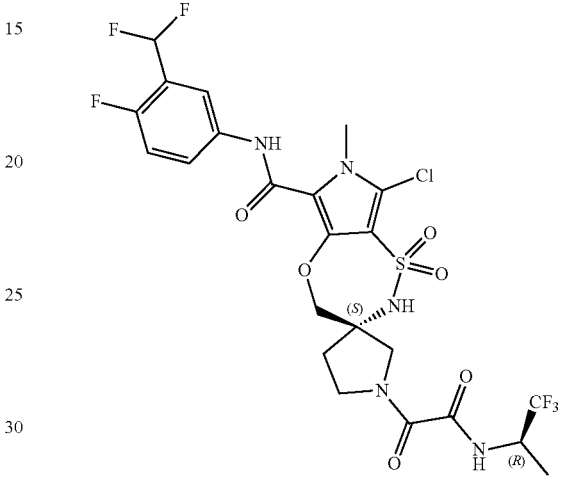

Prepared similarly as described for compound E3 starting from E11 to afford E29 (1.07 mg, 0.002 mmol, y=6%). $^1$H NMR (300 MHz, DMSO-d$_6$) δ ppm 1.30 (d, J=6.97 Hz, 3H) 1.99-2.38 (m, 2H) 3.39-4.23 (m, 7H) 4.39-4.77 (m, 3H) 6.96-7.48 (m, 2H) 7.81 (br dd, J=8.30, 3.90 Hz, 1H) 7.91-8.08 (m, 1H) 8.58 (d, J=5.78 Hz, 1H) 9.32 (t, J=9.17 Hz, 1H) 9.70 (d, J=7.61 Hz, 1H). Method 3: Rt=3.73 min; m/z=646.24 (M+H)$^+$.

Example E30: (R)-8'-chloro-N-(3-chloro-4-fluorophenyl)-7'-methyl-1-(2-oxo-2-((1,1,1-trifluoropropan-2-yl)amino)acetyl)-2'H,4'H,7'H-spiro[piperidine-4,3'-pyrrolo[3,4-b][1,4,5]oxathiazepine]-6'-carboxamide 1',1'-dioxide (E30)

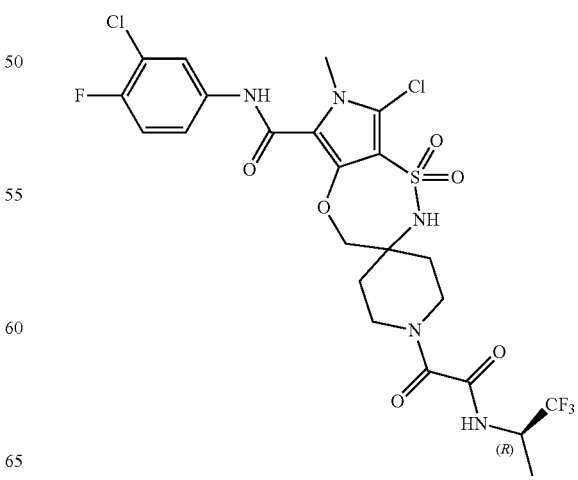

Prepared similarly as described for compound E3 starting from E7 to afford E30 (1.52 mg, 0.002 mmol, y=9%). $^1$H NMR (300 MHz, DMSO-d$_6$+TFA) δ ppm 1.25-1.33 (m, 3H) 1.44-1.73 (m, 3H) 1.99-2.19 (m, 2H) 3.00-3.23 (m, 1H) 3.28-3.45 (m, 1H) 3.45-3.62 (m, 1H) 3.81 (s, 3H) 4.01-4.17 (m, 1H) 4.43 (s, 2H) 4.55-4.74 (m, 1H) 7.39 (t, J=9.03 Hz, 1H) 7.56-7.69 (m, 1H) 7.94 (dd, J=6.79, 2.57 Hz, 1H) 8.21 (s, 1H) 9.32 (dd, J=8.85, 4.54 Hz, 1H) 9.57 (s, 1H). Method 3: Rt=3.80 min; m/z=644.28 (M+H)$^+$.

Example E31: (R)-8'-chloro-N-(3-chloro-4-fluorophenyl)-7'-methyl-1-(2-oxo-2-((1,1,1-trifluoropropan-2-yl)amino)acetyl)-2'H,4'H,7'H-spiro[azetidine-3,3'-pyrrolo[3,4-b][1,4,5]oxathiazepine]-6'-carboxamide 1',1'-dioxide (E31)

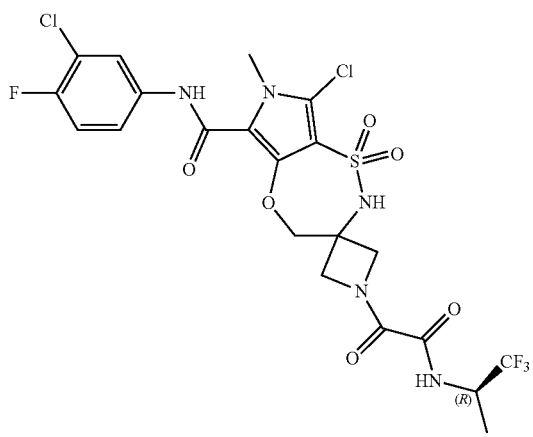

Prepared similarly as described for compound E3 starting from E9 to afford E31 (0.6 mg, 0.001 mmol, y=6%). $^1$H NMR (300 MHz, DMSO-d$_6$) δ ppm 1.31 (dd, J=6.97, 2.38 Hz, 3H) 3.82 (d, J=1.47 Hz, 3H) 4.01-4.24 (m, 2H) 4.45-4.82 (m, 5H) 7.38 (t, J=9.08 Hz, 1H) 7.62-7.74 (m, 1H) 7.91-8.01 (m, 1H) 9.01 (d, J=5.04 Hz, 1H) 9.27 (t, J=9.26 Hz, 1H) 9.59 (d, J=5.23 Hz, 1H). Method 3: Rt=3.90 min; m/z=616.19 (M+H)$^+$.

Example E32: (R)-8'-chloro-N-(3-(difluoromethyl)-4-fluorophenyl)-7'-methyl-1-(2-oxo-2-((1,1,1-trifluoropropan-2-yl)amino)acetyl)-2'H,4'H,7'H-spiro[azetidine-3,3'-pyrrolo[3,4-b][1,4,5]oxathiazepine]-6'-carboxamide 1',1'-dioxide (E32)

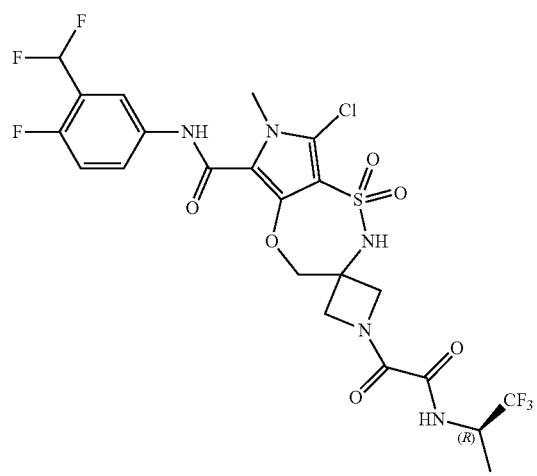

Prepared similarly as described for compound E3 starting from E10 to afford E32 (0.47 mg, 0.001 mmol, y=3%). $^1$H NMR (300 MHz, DMSO-d6+TFA) δ ppm 1.31 (dd, J=7.01, 2.61 Hz, 3H) 3.77-3.87 (m, 3H) 4.01-4.23 (m, 2H) 4.46-4.80 (m, 5H) 6.97-7.43 (m, 2H) 7.76-7.91 (m, 1H) 8.02 (br d, J=4.95 Hz, 1H) 9.01 (d, J=5.04 Hz, 1H) 9.27 (t, J=8.94 Hz, 1H) 9.67 (d, J=5.13 Hz, 1H). Method 3: Rt=3.74 min; m/z=632.5 (M+H)$^+$.

Example E33: (R)-8'-chloro-N-(3-chloro-4-fluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide (E33)

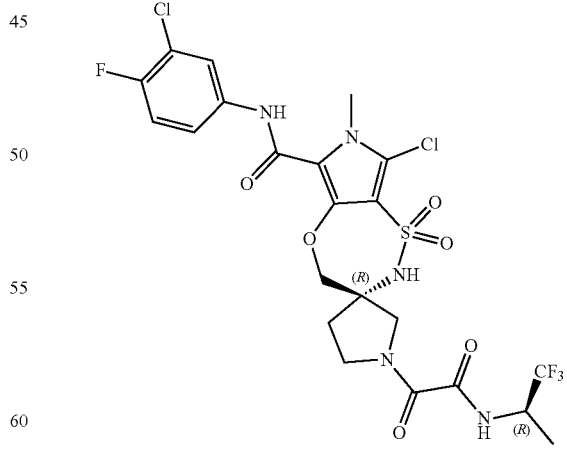

Prepared similarly as described for compound E3 starting from E4 to afford E33 (4 mg, 0.006 mmol, y=14%). $^1$H NMR (300 MHz, DMSO-d$_6$+TFA) δ ppm 1.31 (dd, J=6.83, 5.27 Hz, 3H) 1.97-2.38 (m, 2H) 3.42-4.16 (m, 7H) 4.44-4.75 (m, 3H) 7.41 (t, J=9.12 Hz, 1H) 7.64 (ddd, J=9.06, 4.29, 2.61

Hz, 1H) 7.95 (dt, J=6.79, 2.48 Hz, 1H) 8.61 (d, J=12.20 Hz, 1H) 9.30 (dd, J=13.57, 8.99 Hz, 1H) 9.62 (s, 1H). Method 3: Rt=3.88 min; m/z=630.2 (M+H)⁺.

Example E34: (R)-8'-chloro-N-(3-(difluoromethyl)-4-fluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide (E34)

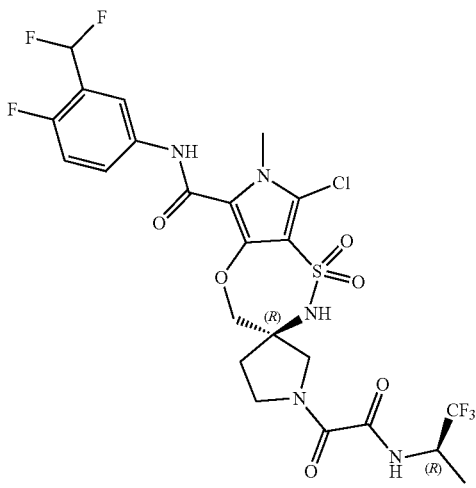

Prepared similarly as described for compound E3 starting from E6 to afford E34 (2.75 mg, 0.001 mmol, y=16%). ¹H NMR (300 MHz, DMSO-d6+TFA) δ ppm 1.30 (dd, J=6.74, 5.36 Hz, 3H) 2.07-2.35 (m, 2H) 3.39-4.18 (m, 7H) 4.33-4.83 (m, 3H) 6.91-7.48 (m, 2H) 7.72-7.88 (m, 1H) 8.00 (br d, J=6.14 Hz, 1H) 8.60 (d, J=12.01 Hz, 1H) 9.29 (dd, J=14.08, 9.03 Hz, 1H) 9.69 (s, 1H). Method 3: Rt=3.73 min; m/z=646.3 (M+H)⁺.

Example E35: (R)-8'-chloro-N-(3-(difluoromethyl)-4-fluorophenyl)-7'-methyl-1-(2-oxo-2-((1,1,1-trifluoropropan-2-yl)amino)acetyl)-2'H,4'H,7'H-spiro[piperidine-4,3'-pyrrolo[3,4-b][1,4,5]oxathiazepine]-6'-carboxamide 1',1'-dioxide (E35)

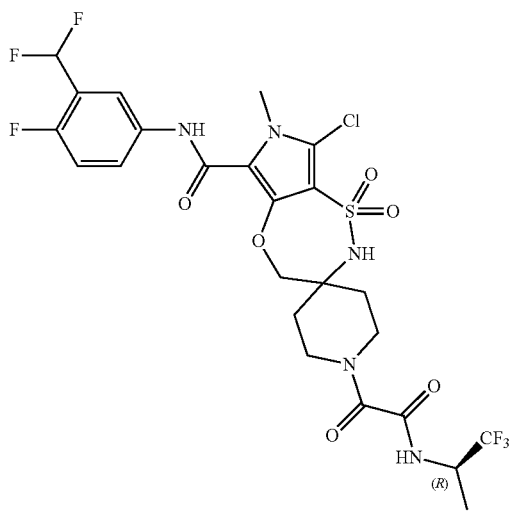

Prepared similarly as described for compound E3 starting from E8 to afford E35 (1.6 mg, 0.002 mmol, y=11%). ¹H NMR (300 MHz, DMSO-d₆+TFA) δ ppm 1.25-1.35 (m, 3H) 1.43-1.73 (m, 2H) 1.99-2.17 (m, 2H) 2.99-3.19 (m, 1H) 3.28-3.45 (m, 1H) 3.45-3.61 (m, 1H) 3.81 (s, 3H) 3.99-4.20 (m, 1H) 4.42 (s, 2H) 4.55-4.75 (m, 1H) 7.22 (t, J=54.00 Hz, 1H) 7.32-7.38 (m, 1H) 7.74-7.87 (m, 1H) 7.99 (dd, J=6.24, 2.29 Hz, 1H) 8.21 (s, 1H) 9.32 (dd, J=8.89, 4.49 Hz, 1H) 9.64 (s, 1H). Method 3: Rt=3.65 min; m/z=660.41 (M+H)⁺.

Example E36: N-(3,4-difluorophenyl)-7'-methyl-1-(2-oxo-2-(((S)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide (E36)

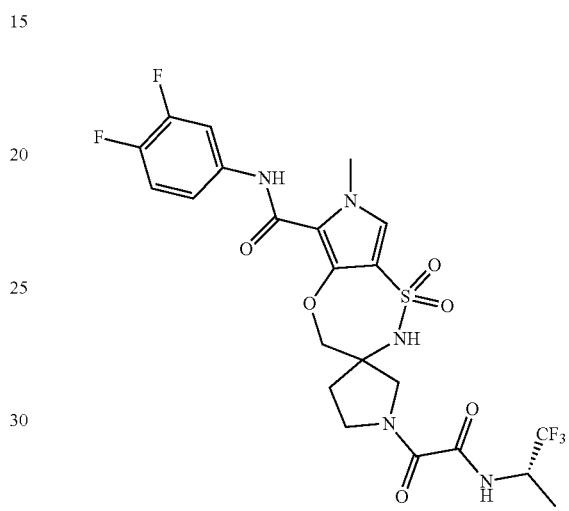

The compound was prepared from D2 as described for the synthesis of E1, using D20 instead of D4. NMR: ¹H NMR (300 MHz, DMSO-d₆+TFA) δ ppm 1.22-1.39 (m, 3H) 1.92-2.40 (m, 2H) 3.44-4.18 (m, 7H) 4.40-4.72 (m, 3H) 7.30-7.57 (m, 3H) 7.75-7.92 (m, 1H) 8.29 (m, 1H) 9.21-9.37 (m, 1H) 9.44 (br dd, J=8.16, 2.84 Hz, 1H). Method 3: Rt=3.54 min; m/z=580.32 (M+H)⁺.

Example E37: 8'-chloro-N-(3,4-difluorophenyl)-7'-methyl-1-(2-oxo-2-(((S)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide (E37)

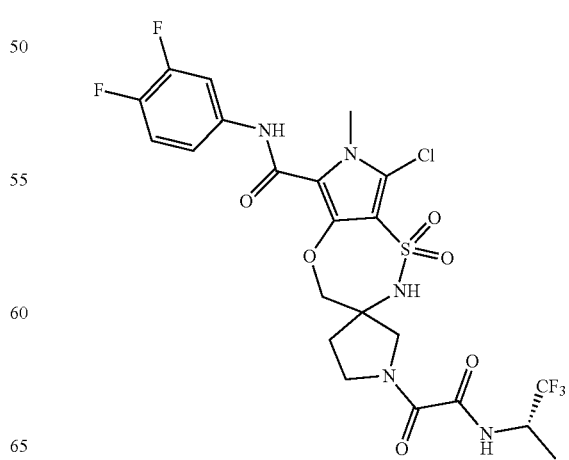

The compound was prepared from E36 using the same procedure described for the synthesis of E3. $^1$H NMR (300 MHz, DMSO-d6+TFA) δ ppm 1.25-1.40 (m, 3H) 1.89-2.38 (m, 2H) 3.38-4.18 (m, 7H) 4.37-4.80 (m, 3H) 7.25-7.55 (m, 2H) 7.66-7.95 (m, 1H) 8.48-8.67 (m, 1H) 9.14-9.40 (m, 1H) 9.64 (t, J=3.94 Hz, 1H). Method 3: Rt=3.74 min; m/z=614.22 (M+H)$^+$.

Biology

Assay

Cells and Culture Conditions

HepAD38 cell line (Ladner et al., Antimicrob Agents Chemother, 1997, 41, 1715-20) was used for HBV inhibition assays. HepAD38 is a subclone, derived from hepatoblastoma cell line HepG2 (ATCC® Number: HB-8065™), that expresses HBV genome under the transcriptional control of a tetracycline-responsive promoter in a TET-OFF system: addition of doxycycline, an antibiotic belonging to the class of tetracycline, suppresses HBV replication, while its removal switches on the process allowing HBV viral particles release in the cell supernatant. HepAD38 cell line is maintained in DMEM/F12, supplemented with 10% of fetal bovine serum, 1% of glutamine, 1% of penicillin/streptomycin, 0.4 mg/ml G418 and 0.3 ug/ml tetracycline. For the HBV inhibition assay, doxycycline-free medium is used in order to allow virion production.

Anti-HBV activity in vitro HBV inhibition activity in vitro was performed in 96 multiwell plates. During the initial (primary) screening, compounds were first tested in triplicates at concentrations of 0.02 μM, 0.1 μM, 0.5 μM and 1 μM. For selected compounds, an 8-point dose-response curve was obtained using 1:2 serial dilutions (starting from 0.01 μM, 0.1 μM, 0.4 μM or 5 μM, depending on the degree of inhibition observed during the primary screening). From the dose-response curves, half maximal effective concentration ($EC_{50}$) could be calculated (see also below).

In more detail, compounds—typically dissolved in DMSO stock solutions—were diluted to 2× the final desired concentration in 100 μl of the above medium (without doxycycline) and plated in three replicates in the 96-well plates.

Simultaneously, HepAD38 cells—extensively pre-washed in doxycycline-free medium in order to induce HBV production—were suspended at $2*10^4$ cells in 100 μl of doxycycline-free medium and added to each well of the plate, to yield a final assay volume of 200 μl DMSO—used for stock solutions and compounds dilutions—which was always present in the assays at a final concentration of 0.5%.

Plates were then incubated 96 hours at 37° C. and then subjected to cell viability assays and extracellular HBV quantification, in order to evaluate both the cytotoxic potential and the anti-viral activity of compounds. Cytotoxicity was assessed by a commercial fluorescence assay that measures the metabolic activity of cells, directly related to cell viability (Cell Titer Blue, Promega). Anti-HBV activity was evaluated by quantification of extracellular HBV DNA with direct qPCR. In particular, supernatant was collected and centrifuged for cell debris clarification, viral DNA was extracted from virions by addition of lysis buffer (1 mM 1,4-dithiothreitol, 0.2% sodium dodecyl sulphate) and incubated at 95° C. for 10 min. Samples were then diluted 1:40 and real time PCR amplification was performed with SYBR green assay (Power SYBR™ Green PCR Master Mix-Thermo Fisher Scientific) and specific HBV primer (HBV-DF:5'-ATTTGTTCAGTGGTTCGTAGGG-3' (SEQ ID No. 1), HBV-DR:5'-CGGTAAAAAGGGACTCAAGATG-3' (SEQ ID No. 2)).

Antiviral activity data for each compound are reported as $EC_5M$ value (see Table 1 legend). Excel and Graphpad Prism programs are typically used for data elaboration and $EC_{50}$ calculation.

Results

The exemplified compounds described herein were tested in the assays described above. All the compounds displayed no significant cytotoxicity at all concentrations of the dose-response curve (maximum tested dose of 0.01 μM, 0.1 μM, 0.4 μM or 5 μM, depending on the compound potency).

Results for HBV inhibition are reported in the following Table 1.

TABLE 1

HBV inhibition for compounds of the invention

| Example | Compound Name | HBV inh $EC_{50}$ (μM) |
|---|---|---|
| E1 | N-(3,4-difluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide | <0.5 |
| E2 | N-(3,4-difluorophenyl)-7'-methyl-1-(5-methyl-1,3,4-oxadiazole-2-carbonyl)-2'H,4'H,7'H-spiro[pyrrolidine-3,3'-pyrrolo[3,4-b][1,4,5]oxathiazepine]-6'-carboxamide 1',1'-dioxide | <0.5 |
| E3 | 8'-chloro-N-(3,4-difluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide | <0.5 |
| E4 | (R)-N-(3-chloro-4-fluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide | <0.5 |
| E5 | (S)-N-(3-chloro-4-fluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide | <0.5 |
| E6 | (R)-N-(3-(difluoromethyl)-4-fluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide | <0.5 |
| E7 | (R)-N-(3-chloro-4-fluorophenyl)-7'-methyl-1-(2-oxo-2-((1,1,1-trifluoropropan-2-yl)amino)acetyl)-2'H,4'H,7'H-spiro[piperidine-4,3'-pyrrolo[3,4-b][1,4,5]oxathiazepine]-6'-carboxamide 1',1'-dioxide | <0.5 |
| E8 | (R)-N-(3-(difluoromethyl)-4-fluorophenyl)-7'-methyl-1-(2-oxo-2-((1,1,1-trifluoropropan-2-yl)amino)acetyl)-2'H,4'H,7'H-spiro[piperidine-4,3'-pyrrolo[3,4-b][1,4,5]oxathiazepine]-6'-carboxamide 1',1'-dioxide | <0.5 |

TABLE 1-continued

HBV inhibition for compounds of the invention

| Example | Compound Name | HBV inh EC$_{50}$ (μM) |
|---|---|---|
| E9 | (R)-N-(3-chloro-4-fluorophenyl)-7'-methyl-1-(2-oxo-2-((1,1,1-trifluoropropan-2-yl)amino)acetyl)-2'H,4'H,7'H-spiro[azetidine-3,3'-pyrrolo[3,4-b][1,4,5]oxathiazepine]-6'-carboxamide 1',1'-dioxide | <0.5 |
| E10 | (R)-N-(3-(difluoromethyl)-4-fluorophenyl)-7'-methyl-1-(2-oxo-2-((1,1,1-trifluoropropan-2-yl)amino)acetyl)-2'H,4'H,7'H-spiro[azetidine-3,3'-pyrrolo[3,4-b][1,4,5]oxathiazepine]-6'-carboxamide 1',1'-dioxide | <0.5 |
| E11 | (S)-N-(3-(difluoromethyl)-4-fluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide | <0.5 |
| E12 | (S)-N-(3-chloro-4-fluorophenyl)-7'-methyl-1-(2-oxo-2-((1,1,1-trifluoropropan-2-yl)amino)acetyl)-2'H,4'H,7'H-spiro[piperidine-4,3'-pyrrolo[3,4-b][1,4,5]oxathiazepine]-6'-carboxamide 1',1'-dioxide | <0.5 |
| E13 | N-(3-chloro-4-fluorophenyl)-7'-methyl-1-(2-oxo-2-((2,2,2-trifluoroethyl)amino)acetyl)-2'H,4'H,7'H-spiro[piperidine-4,3'-pyrrolo[3,4-b][1,4,5]oxathiazepine]-6'-carboxamide 1',1'-dioxide | <0.5 |
| E14 | (S)-N-(3-(difluoromethyl)-4-fluorophenyl)-7'-methyl-1-(2-oxo-2-((1,1,1-trifluoropropan-2-yl)amino)acetyl)-2'H,4'H,7'H-spiro[piperidine-4,3'-pyrrolo[3,4-b][1,4,5]oxathiazepine]-6'-carboxamide 1',1'-dioxide | <0.5 |
| E15 | N-(3-(difluoromethyl)-4-fluorophenyl)-7'-methyl-1-(2-oxo-2-((1,1,1-trifluoro-2-methylpropan-2-yl)amino)acetyl)-2'H,4'H,7'H-spiro[piperidine-4,3'-pyrrolo[3,4-b][1,4,5]oxathiazepine]-6'-carboxamide 1',1'-dioxide | <0.5 |
| E16 | (S)-N-(3-chloro-4-fluorophenyl)-7'-methyl-1-(2-oxo-2-((1,1,1-trifluoropropan-2-yl)amino)acetyl)-2'H,4'H,7'H-spiro[azetidine-3,3'-pyrrolo[3,4-b][1,4,5]oxathiazepine]-6'-carboxamide 1',1'-dioxide | <0.5 |
| E17 | N-(3-chloro-4-fluorophenyl)-1-(2-(3,3-difluoroazetidin-1-yl)-2-oxoacetyl)-7'-methyl-2'H,4'H,7'H-spiro[azetidine-3,3'-pyrrolo[3,4-b][1,4,5]oxathiazepine]-6'-carboxamide 1',1'-dioxide | <0.5 |
| E18 | (S)-N-(3-(difluoromethyl)-4-fluorophenyl)-7'-methyl-1-(2-oxo-2-((1,1,1-trifluoropropan-2-yl)amino)acetyl)-2'H,4'H,7'H-spiro[azetidine-3,3'-pyrrolo[3,4-b][1,4,5]oxathiazepine]-6'-carboxamide 1',1'-dioxide | <0.5 |
| E19 | 1-(2-(cyclopropylamino)-2-oxoacetyl)-N-(3-(difluoromethyl)-4-fluorophenyl)-7'-methyl-2'H,4'H,7'H-spiro[azetidine-3,3'-pyrrolo[3,4-b][1,4,5]oxathiazepine]-6'-carboxamide 1',1'-dioxide | <0.5 |
| E20 | (R)-N-(3-chloro-4-fluorophenyl)-7'-methyl-1-(2-oxo-2-((2,2,2-trifluoroethyl)amino)acetyl)-2'H,4'H,7'H-spiro[pyrrolidine-3,3'-pyrrolo[3,4-b][1,4,5]oxathiazepine]-6'-carboxamide 1',1'-dioxide | <0.5 |
| E21 | (R)-N-(3-chloro-4-fluorophenyl)-7'-methyl-1-(2-oxo-2-((1,1,1-trifluoro-2-methylpropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide | <0.5 |
| E22 | (R)-N-(3-chloro-4-fluorophenyl)-7'-methyl-1-(2-oxo-2-(((S)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide | <0.5 |
| E23 | (R)-N-(3-(difluoromethyl)-4-fluorophenyl)-7'-methyl-1-(2-oxo-2-(((S)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide | <0.5 |
| E24 | (R)-N-(3-(difluoromethyl)-4-fluorophenyl)-7'-methyl-1-(2-oxo-2-((1,1,1-trifluoro-2-methylpropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide | <0.5 |
| E25 | (S)-N-(3-chloro-4-fluorophenyl)-7'-methyl-1-(2-oxo-2-((2,2,2-trifluoroethyl)amino)acetyl)-2'H,4'H,7'H-spiro[pyrrolidine-3,3'-pyrrolo[3,4-b][1,4,5]oxathiazepine]-6'-carboxamide 1',1'-dioxide | <0.5 |
| E26 | (S)-N-(3-chloro-4-fluorophenyl)-7'-methyl-1-(2-oxo-2-((1,1,1-trifluoro-2-methylpropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide | <0.5 |
| E27 | (S)-N-(3-(difluoromethyl)-4-fluorophenyl)-7'-methyl-1-(2-oxo-2-((2,2,2-trifluoroethyl)amino)acetyl)-2'H,4'H,7'H-spiro[pyrrolidine-3,3'-pyrrolo[3,4-b][1,4,5]oxathiazepine]-6'-carboxamide 1',1'-dioxide | <0.5 |
| E28 | (S)-N-(3-(difluoromethyl)-4-fluorophenyl)-7'-methyl-1-(2-oxo-2-((1,1,1-trifluoro-2-methylpropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide | <0.5 |
| E29 | (S)-8'-chloro-N-(3-(difluoromethyl)-4-fluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide | <0.5 |
| E30 | (R)-8'-chloro-N-(3-chloro-4-fluorophenyl)-7'-methyl-1-(2-oxo-2-((1,1,1-trifluoropropan-2-yl)amino)acetyl)-2'H,4'H,7'H-spiro[piperidine-4,3'-pyrrolo[3,4-b][1,4,5]oxathiazepine]-6'-carboxamide 1',1'-dioxide | <0.5 |
| E31 | (R)-8'-chloro-N-(3-chloro-4-fluorophenyl)-7'-methyl-1-(2-oxo-2-((1,1,1-trifluoropropan-2-yl)amino)acetyl)-2'H,4'H,7'H-spiro[azetidine-3,3'-pyrrolo[3,4-b][1,4,5]oxathiazepine]-6'-carboxamide 1',1'-dioxide | <0.5 |
| E32 | (R)-8'-chloro-N-(3-(difluoromethyl)-4-fluorophenyl)-7'-methyl-1-(2-oxo-2-((1,1,1-trifluoropropan-2-yl)amino)acetyl)-2'H,4'H,7'H-spiro[azetidine-3,3'-pyrrolo[3,4-b][1,4,5]oxathiazepine]-6'-carboxamide 1',1'-dioxide | <0.5 |
| E33 | (R)-8'-chloro-N-(3-chloro-4-fluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide | <0.5 |

TABLE 1-continued

HBV inhibition for compounds of the invention

| Example | Compound Name | HBV inh EC$_{50}$ (µM) |
|---|---|---|
| E34 | (R)-8'-chloro-N-(3-(difluoromethyl)-4-fluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide | <0.5 |
| E35 | (R)-8'-chloro-N-(3-(difluoromethyl)-4-fluorophenyl)-7'-methyl-1-(2-oxo-2-((1,1,1-trifluoropropan-2-yl)amino)acetyl)-2'H,4'H,7'H-spiro[piperidine-4,3'-pyrrolo[3,4-b][1,4,5]oxathiazepine]-6'-carboxamide 1',1'-dioxide | <0.5 |
| E36 | N-(3,4-difluorophenyl)-7'-methyl-1-(2-oxo-2-(((S)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide | <0.5 |
| E37 | 8'-chloro-N-(3,4-difluorophenyl)-7'-methyl-1-(2-oxo-2-(((S)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide | <0.5 |

The invention claimed is:

1. A compound of general formula (I):

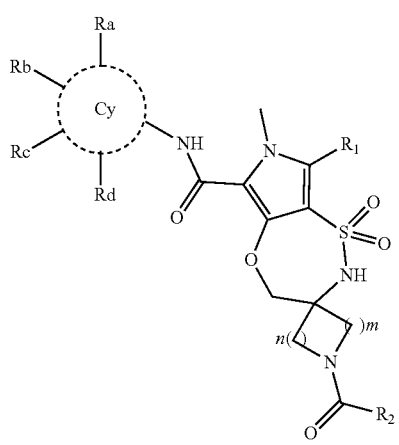

wherein:
Cy is aryl or heteroaryl;
each of m and n is independently 1 or 2;
$R_1$ is H, F, Br, Cl or $CH_3$;
$R_2$ is selected from the group consisting of:
  5 or 6 membered heteroaryl ring optionally substituted with one or more substituents each independently selected from the group consisting of: OH, halogen, CN, $C_{1-6}$alkyl, hydroxy$C_{1-6}$alkyl, halo$C_{1-6}$alkyl, halo$C_{1-6}$alkoxy, $C_{1-6}$alkoxy and $NH_2$;
  halo$C_{1-4}$alkyl; and
  $C(=O)NR_3R_4$;
each of $R_3$ and $R_4$ is independently selected from the group consisting of:
  hydrogen;
  $C_{1-3}$alkyl;
  halo$C_{1-4}$alkyl; and
  $C_{3-5}$-cycloalkyl optionally substituted with one or more substituents each independently selected from the group consisting of: methyl, F, Cl, $CHF_2$ and $CF_3$;
or $R_3$ and $R_4$ form together with the nitrogen atom to which they are attached a cyclic amine selected from the group consisting of: aziridine, azetidine, pyrrolidine, piperidine, morpholine and thiomorpholine each of said cyclic amine being optionally substituted with one or more substituents each independently selected from the group consisting of: methyl, fluorine, CHF$_2$ and CF$_3$;

Ra, Rb, Rc and Rd are each independently selected from the group consisting of: hydrogen, halogen, methyl, CN, CHF$_2$ and CF$_3$;

or a pharmaceutically acceptable salt, solvate or stereoisomer thereof.

2. The compound according to claim 1, wherein R$_2$ is:

5 membered heteroaryl ring optionally substituted with one or more substituents each independently selected from the group consisting of: OH, halogen, CN, methyl and trifluoromethyl; or C(=O)NR$_3$R$_4$ wherein R$_3$ is H and R$_4$ is selected from the group consisting of: C$_{1-3}$alkyl, haloC$_{1-4}$alkyl and C$_{3-5}$-cycloalkyl optionally substituted with one or more substituents each independently selected from the group consisting of: methyl, fluorine and CF$_3$;

or R$_3$ and R$_4$ form together with the nitrogen atom to which they are attached a cyclic amine selected from the group consisting of: aziridine, azetidine, pyrrolidine and piperidine, each of said cyclic amine being optionally substituted with one or more substituents each independently selected from the group consisting of: methyl, fluorine and CF$_3$;

or a pharmaceutically acceptable salt, solvate or stereoisomer thereof.

3. The compound according to claim 1, wherein Ra, Rb, Rc and Rd are each independently selected from the group consisting of: hydrogen, Cl, F, methyl and CHF$_2$ or a pharmaceutically acceptable salt, solvate or stereoisomer thereof.

4. The compound according to claim 1, wherein:

m is 1 and n is 2; or m is 2 and n is 2; or m is 1 and n is 1; or

R$_1$ is H or Cl;

or a pharmaceutically acceptable salt, solvate or stereoisomer thereof.

5. The compound according to claim 1, wherein:

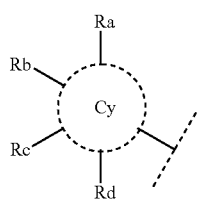

represents

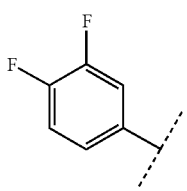 or 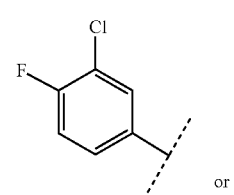 or

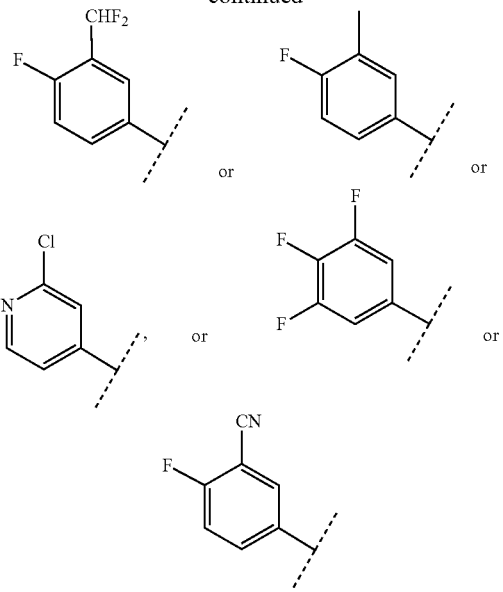

or a pharmaceutically acceptable salt, solvate or stereoisomer thereof.

6. The compound according to claim 1, wherein R$_2$ is:

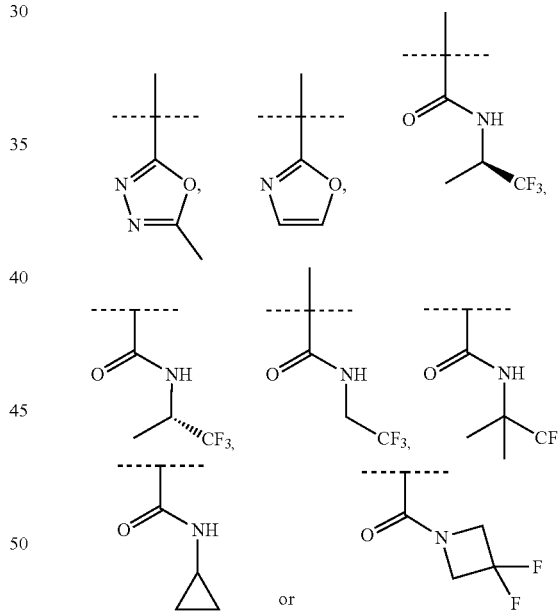

or a pharmaceutically acceptable salt, solvate or stereoisomer thereof.

7. The compound according to claim 1 being selected from the following list:

N-(3,4-difluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide;

N-(3,4-difluorophenyl)-7'-methyl-1-(5-methyl-1,3,4-oxadiazole-2-carbonyl)-2'H,4'H,7'H-spiro[pyrrolidine-3,3'-pyrrolo[3,4-b][1,4,5]oxathiazepine]-6'-carboxamide 1',1'-dioxide;

8'-chloro-N-(3,4-difluorophenyl)-7'-methyl-1-(2-oxo-2-(((R)-1,1,1-trifluoropropan-2-yl)amino)acetyl)-2'H, 4'H,7'H-spiro[pyrrolidine-3,3'-pyrrolo[3,4-b][1,4,5]oxathiazepine]-6'-carboxamide 1',1'-dioxide;

(R)—N-(3-chloro-4-fluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide;

(S)—N-(3-chloro-4-fluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide;

(R)—N-(3-(difluoromethyl)-4-fluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide;

(R)—N-(3-chloro-4-fluorophenyl)-7'-methyl-1-(2-oxo-2-((1,1,1-trifluoropropan-2-yl)amino)acetyl)-2'H,4'H,7'H-spiro[piperidine-4,3'-pyrrolo[3,4-b][1,4,5]oxathiazepine]-6'-carboxamide 1',1'-dioxide;

(R)—N-(3-(difluoromethyl)-4-fluorophenyl)-7'-methyl-1-(2-oxo-2-((1,1,1-trifluoropropan-2-yl)amino)acetyl)-2'H,4'H,7'H-spiro[piperidine-4,3'-pyrrolo[3,4-b][1,4,5]oxathiazepine]-6'-carboxamide 1',1'-dioxide;

(R)—N-(3-chloro-4-fluorophenyl)-7'-methyl-1-(2-oxo-2-((1,1,1-trifluoropropan-2-yl)amino)acetyl)-2'H,4'H,7'H-spiro[azetidine-3,3'-pyrrolo[3,4-b][1,4,5]oxathiazepine]-6'-carboxamide 1',1'-dioxide;

(R)—N-(3-(difluoromethyl)-4-fluorophenyl)-7'-methyl-1-(2-oxo-2-((1,1,1-trifluoropropan-2-yl)amino)acetyl)-2'H,4'H,7'H-spiro[azetidine-3,3'-pyrrolo[3,4-b][1,4,5]oxathiazepine]-6'-carboxamide 1',1'-dioxide;

(S)—N-(3-(difluoromethyl)-4-fluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide;

(S)—N-(3-chloro-4-fluorophenyl)-7'-methyl-1-(2-oxo-2-((1,1,1-trifluoropropan-2-yl)amino)acetyl)-2'H,4'H,7'H-spiro[piperidine-4,3'-pyrrolo[3,4-b][1,4,5]oxathiazepine]-6'-carboxamide 1',1'-dioxide;

N-(3-chloro-4-fluorophenyl)-7'-methyl-1-(2-oxo-2-((2,2,2-trifluoroethyl)amino)acetyl)-2'H,4'H,7'H-spiro[piperidine-4,3'-pyrrolo[3,4-b][1,4,5]oxathiazepine]-6'-carboxamide 1',1'-dioxide;

(S)—N-(3-(difluoromethyl)-4-fluorophenyl)-7'-methyl-1-(2-oxo-2-((1,1,1-trifluoropropan-2-yl)amino)acetyl)-2'H,4'H,7'H-spiro[piperidine-4,3'-pyrrolo[3,4-b][1,4,5]oxathiazepine]-6'-carboxamide 1',1'-dioxide;

N-(3-(difluoromethyl)-4-fluorophenyl)-7'-methyl-1-(2-oxo-2-((1,1,1-trifluoro-2-methylpropan-2-yl)amino)acetyl)-2'H,4'H,7'H-spiro[piperidine-4,3'-pyrrolo[3,4-b][1,4,5]oxathiazepine]-6'-carboxamide 1',1'-dioxide;

(S)—N-(3-chloro-4-fluorophenyl)-7'-methyl-1-(2-oxo-2-((1,1,1-trifluoropropan-2-yl)amino)acetyl)-2'H,4'H,7'H-spiro[azetidine-3,3'-pyrrolo[3,4-b][1,4,5]oxathiazepine]-6'-carboxamide 1',1'-dioxide;

N-(3-chloro-4-fluorophenyl)-1-(2-(3,3-difluoroazetidin-1-yl)-2-oxoacetyl)-7'-methyl-2'H,4'H,7'H-spiro[azetidine-3,3'-pyrrolo[3,4-b][1,4,5]oxathiazepine]-6'-carboxamide 1',1'-dioxide;

(S)—N-(3-(difluoromethyl)-4-fluorophenyl)-7'-methyl-1-(2-oxo-2-((1,1,1-trifluoropropan-2-yl)amino)acetyl)-2'H,4'H,7'H-spiro[azetidine-3,3'-pyrrolo[3,4-b][1,4,5]oxathiazepine]-6'-carboxamide 1',1'-dioxide;

1-(2-(cyclopropylamino)-2-oxoacetyl)-N-(3-(difluoromethyl)-4-fluorophenyl)-7'-methyl-2'H,4'H,7'H-spiro[azetidine-3,3'-pyrrolo[3,4-b][1,4,5]oxathiazepine]-6'-carboxamide 1',1'-dioxide;

(R)—N-(3-chloro-4-fluorophenyl)-7'-methyl-1-(2-oxo-2-((2,2,2-trifluoroethyl)amino)acetyl)-2'H,4'H,7'H-spiro[pyrrolidine-3,3'-pyrrolo[3,4-b][1,4,5]oxathiazepine]-6'-carboxamide 1',1'-dioxide;

(R)—N-(3-chloro-4-fluorophenyl)-7'-methyl-1-(2-oxo-2-((1,1,1-trifluoro-2-methylpropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide;

(R)—N-(3-chloro-4-fluorophenyl)-7'-methyl-1-(2-oxo-2-(((S)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide;

(R)—N-(3-(difluoromethyl)-4-fluorophenyl)-7'-methyl-1-(2-oxo-2-(((S)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide;

(R)—N-(3-(difluoromethyl)-4-fluorophenyl)-7'-methyl-1-(2-oxo-2-((1,1,1-trifluoro-2-methylpropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide;

(S)—N-(3-chloro-4-fluorophenyl)-7'-methyl-1-(2-oxo-2-((2,2,2-trifluoroethyl)amino)acetyl)-2'H,4'H,7'H-spiro[pyrrolidine-3,3'-pyrrolo[3,4-b][1,4,5]oxathiazepine]-6'-carboxamide 1',1'-dioxide;

(S)—N-(3-chloro-4-fluorophenyl)-7'-methyl-1-(2-oxo-2-((1,1,1-trifluoro-2-methylpropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide;

(S)—N-(3-(difluoromethyl)-4-fluorophenyl)-7'-methyl-1-(2-oxo-2-((2,2,2-trifluoroethyl)amino)acetyl)-2'H,4'H,7'H-spiro[pyrrolidine-3,3'-pyrrolo[3,4-b][1,4,5]oxathiazepine]-6'-carboxamide 1',1'-dioxide;

(S)—N-(3-(difluoromethyl)-4-fluorophenyl)-7'-methyl-1-(2-oxo-2-((1,1,1-trifluoro-2-methylpropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide;

(S)-8'-chloro-N-(3-(difluoromethyl)-4-fluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide;

(R)-8'-chloro-N-(3-chloro-4-fluorophenyl)-7'-methyl-1-(2-oxo-2-((1,1,1-trifluoropropan-2-yl)amino)acetyl)-2'H,4'H,7'H-spiro[piperidine-4,3'-pyrrolo[3,4-b][1,4,5]oxathiazepine]-6'-carboxamide 1',1'-dioxide;

(R)-8'-chloro-N-(3-chloro-4-fluorophenyl)-7'-methyl-1-(2-oxo-2-((1,1,1-trifluoropropan-2-yl)amino)acetyl)-2'H,4'H,7'H-spiro[azetidine-3,3'-pyrrolo[3,4-b][1,4,5]oxathiazepine]-6'-carboxamide 1',1'-dioxide;

(R)-8'-chloro-N-(3-(difluoromethyl)-4-fluorophenyl)-7'-methyl-1-(2-oxo-2-((1,1,1-trifluoropropan-2-yl)amino)acetyl)-2'H,4'H,7'H-spiro[azetidine-3,3'-pyrrolo[3,4-b][1,4,5]oxathiazepine]-6'-carboxamide 1',1'-dioxide;

(R)-8'-chloro-N-(3-chloro-4-fluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide;

(R)-8'-chloro-N-(3-(difluoromethyl)-4-fluorophenyl)-7'-methyl-1-(2-oxo-2-(((R)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide;

(R)-8'-chloro-N-(3-(difluoromethyl)-4-fluorophenyl)-7'-methyl-1-(2-oxo-2-((1,1,1-trifluoropropan-2-yl)amino)

acetyl)-2'H,4'H,7'H-spiro[piperidine-4,3'-pyrrolo[3,4-b][1,4,5]oxathiazepine]-6'-carboxamide 1',1'-dioxide;

N-(3,4-difluorophenyl)-7'-methyl-1-(2-oxo-2-(((S)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide; and 8'-chloro-N-(3,4-difluorophenyl)-7'-methyl-1-(2-oxo-2-(((S)-1,1,1-trifluoropropan-2-yl)amino)acetyl)-2'H,4'H,7'H-spiro[pyrrolidine-3,3'-pyrrolo[3,4-b][1,4,5]oxathiazepine]-6'-carboxamide 1',1'-dioxide or a pharmaceutically acceptable salt, solvate or stereoisomer thereof.

8. A method for the treatment and/or prevention of an HBV infection and/or a condition related to an HBV infection, comprising administering an effective amount of a compound of claim 1 to a subject in need thereof.

9. A method for treating, eradicating, reducing, slowing or inhibiting an HBV infection in an individual in need thereof, and/or in reducing the viral load associated with an HBV infection in an individual in need thereof, and/or in reducing reoccurrence of an HBV infection in an individual in need thereof, and/or in inducing remission of hepatic injury from an HBV infection in an individual in need thereof, and/or in prophylactically treating an HBV infection in an individual afflicted with a latent HBV infection, comprising administering an effective amount of a compound of claim 1 to a subject in need thereof.

10. The method of claim 9, further comprising administering at least one further therapeutic agent.

11. A pharmaceutical composition comprising the compound, pharmaceutically acceptable salt, solvate or stereoisomer of claim 1, alone or in combination with at least one further therapeutic agent, and at least one pharmaceutically acceptable excipient.

12. A process for the synthesis of the compound, pharmaceutically acceptable salt, solvate or stereoisomer of claim 1, comprising at least one of the following steps:

(6)

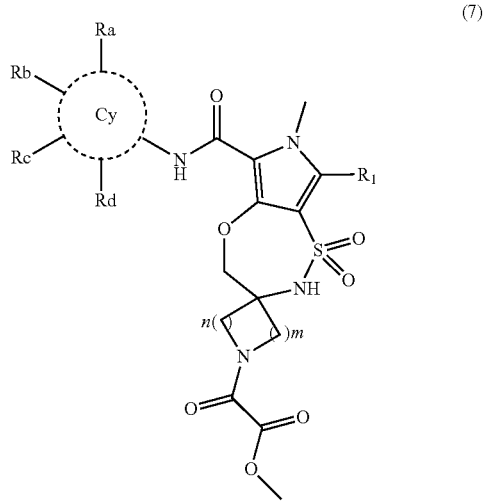

(9)

reacting a compound of formula (6) with an agent selected from the group consisting of: a compound of formula (9), an acid of formula $R_2COOH$ and an acyl chloride of formula $R_2COCl$;

(7)

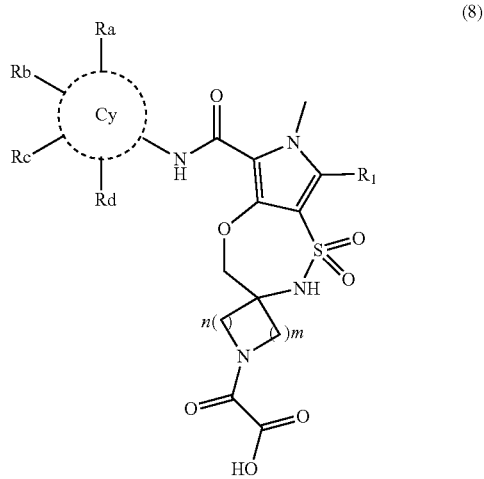

(8)

reacting a compound of formula (7) or (8) with an amine of formula $NHR_3R_4$;

said process optionally further comprising at least one of the following steps:
reacting a compound of formula (6) with methyl 2-chloro-2-oxoacetate to obtain a compound of formula (7);
hydrolyzing a compound of formula (7) in the presence of a base to obtain a compound of formula (8).

13. The compound of claim 1, wherein m is 1 and n is 2 and R1 is H or Cl.

14. The compound of claim 1, wherein m is 2 and n is 2 and R1 is H or Cl.

15. The compound of claim 1, wherein m is 1 and n is 1 and R1 is H or Cl.

16. The method of claim 10, wherein the at least one further therapeutic agent is selected from the group consisting of a therapeutic vaccine, an RNA interference therapeutic/antisense oligonucleotide; and immunomodulator, a STING agonist, a RIG-I modulator, a NKT modulator, an IL agonist; an interleukin; an immune acting protein; a therapeutic and prophylactic vaccine; an immune checkpoint modulator/inhibitor; an HBV entry inhibitor; a cccDNA modulator; an inhibitor of HBV protein expression; an agent targeting HBV RNA; a capsid assembly inhibitor/modulator; a core or X protein targeting agent; a nucleotide analogue; a nucleoside analogue; an interferon or a modified interferon; an HBV antiviral of distinct or unknown mechanism; a cyclophilin inhibitor; a sAg release inhibitor; a HBV polymerase inhibitor; a dinucleotide; a SMAC inhibitor; a HDV targeting agent; a viral maturation inhibitor; a reverse transcriptase inhibitor; an HBV RNA destabilizer; and a small-molecule inhibitor of HBV protein expression; or combinations thereof.

17. The pharmaceutical composition of claim 11, wherein the at least one further therapeutic agent is selected from the group consisting of a therapeutic vaccine; an RNA interference therapeutic/antisense oligonucleotide; an immunomodulator; a STING agonist; a RIG-I modulator; a NKT modulator; an IL agonist; an interleukin, an immune acting protein; a therapeutic and prophylactic vaccine; an immune checkpoint modulator/inhibitor; an HBV entry inhibitor; a cccDNA modulator; an inhibitor of HBV protein expression; an agent targeting HBV RNA; a capsid assembly inhibitor/modulator; a core or X protein targeting agent; a nucleotide analogue; a nucleoside analogue; an interferon, a modified interferon; an HBV antiviral of distinct or unknown mechanism; a cyclophilin inhibitor; a sAg release inhibitor; a HBV polymerase inhibitor; a dinucleotide; a SMAC inhibitor; a HDV targeting agent; a viral maturation inhibitor; a reverse transcriptase inhibitor and an HBV RNA destabilizer or another small-molecule inhibitor of HBV protein expression; or combinations thereof.

* * * * *

SEQUENCE LISTING

<160> NUMBER OF SEQ ID NOS: 2

<210> SEQ ID NO 1
<211> LENGTH: 22
<212> TYPE: DNA
<213> ORGANISM: Artificial Sequence
<220> FEATURE:
<223> OTHER INFORMATION: Synthetic primer

<400> SEQUENCE: 1
atttgttcag tggttcgtag gg                                          22

<210> SEQ ID NO 2
<211> LENGTH: 22
<212> TYPE: DNA
<213> ORGANISM: Artificial Sequence
<220> FEATURE:
<223> OTHER INFORMATION: Synthetic primer

<400> SEQUENCE: 2
cggtaaaaag ggactcaaga tg                                          22